US011717826B2

(12) United States Patent
Park et al.

(10) Patent No.: US 11,717,826 B2
(45) Date of Patent: Aug. 8, 2023

(54) NUCLEIC ACID ANALYSIS APPARATUS USING CARTRIDGE

(71) Applicant: SK Telecom Co., Ltd., Seoul (KR)

(72) Inventors: Chin Sung Park, Seoul (KR); Jin Seok Kang, Seoul (KR); Jong Sun Kim, Seoul (KR); Jun Hong Min, Seoul (KR); Jeong Jin Choi, Seoul (KR)

(73) Assignee: SK Telecom Co., Ltd., Seoul (KR)

( * ) Notice: Subject to any disclaimer, the term of this patent is extended or adjusted under 35 U.S.C. 154(b) by 697 days.

(21) Appl. No.: 16/683,654

(22) Filed: Nov. 14, 2019

(65) Prior Publication Data

US 2020/0078787 A1  Mar. 12, 2020

Related U.S. Application Data

(63) Continuation of application No. PCT/KR2018/005282, filed on May 8, 2018.

(30) Foreign Application Priority Data

May 16, 2017 (KR) .................. 10-2017-0060609
May 16, 2017 (KR) .................. 10-2017-0060610
May 16, 2017 (KR) .................. 10-2017-0060611

(51) Int. Cl.
*B01L 3/00* (2006.01)
*C12N 13/00* (2006.01)
(Continued)

(52) U.S. Cl.
CPC ..... *B01L 3/502738* (2013.01); *B01L 3/50273* (2013.01); *B01L 3/502715* (2013.01);
(Continued)

(58) Field of Classification Search
CPC . B01L 3/502715; B01L 3/502738; B01L 7/52
See application file for complete search history.

(56) References Cited

U.S. PATENT DOCUMENTS 6,919,175 B1 * 7/2005 Bienhaus ........... C12N 15/1013
435/270
9,574,225 B2 * 2/2017 Himmelreich ..... C12N 15/1013
(Continued)

FOREIGN PATENT DOCUMENTS

CN    101147070 A    3/2008
JP    2008-508876 A    3/2008
(Continued)

OTHER PUBLICATIONS

Extended European Search Report, European Application No. 18802686.8, dated May 15, 2020, 13 pages.
(Continued)

*Primary Examiner* — Jonathan M Hurst
(74) *Attorney, Agent, or Firm* — WTA Patents

(57) ABSTRACT

The present disclosure relates to a nucleic acid analysis apparatus using a cartridge which can simplify the nucleic acid extraction and applicable to a molecular diagnostic POCT equipment. The nucleic acid analysis device includes a stage on which a cartridge is mountable, a nucleic acid extraction unit, and a control unit. The nucleic acid extraction unit performs a nucleic acid extraction through crushing of the sample, the cell disruption, and the nucleic acid purification as well as a nucleic acid amplification. The control unit controls the stage and the nucleic acid extraction unit so that the nucleic acid extraction through the crushing of the sample, the cell disruption, and the nucleic acid purification as well as the nucleic acid amplification are collectively performed.

13 Claims, 34 Drawing Sheets

(51) Int. Cl.
*C12N 15/10* (2006.01)
*G01N 1/28* (2006.01)
*G01N 1/34* (2006.01)
*B01L 7/00* (2006.01)
*C12Q 1/6844* (2018.01)
*G01N 21/64* (2006.01)

(52) U.S. Cl.
CPC .............. *B01L 7/52* (2013.01); *B01L 13/02* (2019.08); *C12N 13/00* (2013.01); *C12N 15/1013* (2013.01); *C12Q 1/6844* (2013.01); *G01N 1/286* (2013.01); *G01N 1/34* (2013.01); *G01N 21/6486* (2013.01); *B01L 2200/10* (2013.01); *B01L 2200/141* (2013.01); *B01L 2300/041* (2013.01); *B01L 2300/06* (2013.01); *B01L 2300/0627* (2013.01); *B01L 2300/0681* (2013.01); *B01L 2300/0861* (2013.01); *B01L 2300/123* (2013.01); *B01L 2300/14* (2013.01); *B01L 2300/1805* (2013.01); *B01L 2400/0487* (2013.01); *B01L 2400/06* (2013.01); *G01N 2001/2866* (2013.01)

(56) References Cited

U.S. PATENT DOCUMENTS

| | | | | |
|---|---|---|---|---|
| 2009/0035847 A1* | 2/2009 | Cho | ........................ | B01F 33/30 435/289.1 |
| 2010/0234237 A1 | 9/2010 | Yoo | | |
| 2012/0214168 A1* | 8/2012 | Young | .................. | C12Q 1/6806 435/6.12 |
| 2013/0210127 A1* | 8/2013 | Williams | ............ | B01L 3/50273 435/287.2 |
| 2013/0230906 A1* | 9/2013 | Martinelli | ......... | B01L 3/502738 435/283.1 |
| 2014/0227146 A1* | 8/2014 | Kusner | ................... | B01L 7/525 422/501 |
| 2014/0335527 A1* | 11/2014 | Goel | ................. | B01L 3/502738 435/6.12 |
| 2015/0151300 A1 | 6/2015 | Williams et al. | | |
| 2016/0108459 A1* | 4/2016 | Han | ...................... | C12Q 1/6806 435/287.2 |
| 2017/0022547 A1* | 1/2017 | Chan | .................... | C12Q 1/6816 |
| 2017/0128946 A1* | 5/2017 | Williams | ............. | B01L 3/50851 |
| 2018/0095100 A1* | 4/2018 | Nguyen | ........... | G01N 35/00732 |
| 2019/0344269 A1* | 11/2019 | Johnson | .................. | B01L 3/527 |
| 2019/0351409 A1* | 11/2019 | Schnell | ............. | B01L 3/502753 |
| 2019/0383841 A1* | 12/2019 | Feitsma | ............. | G01N 35/0098 |
| 2020/0078787 A1* | 3/2020 | Park | ........................ | B01L 13/02 |
| 2021/0031183 A1* | 2/2021 | Wernerehl | ........ | B01L 3/502738 |
| 2022/0162585 A1* | 5/2022 | Spangler | ............... | B01L 3/5021 |
| 2022/0168741 A1* | 6/2022 | Hama | ....................... | G01N 1/10 |

FOREIGN PATENT DOCUMENTS

| | | |
|---|---|---|
| JP | 2014-021052 A | 2/2014 |
| KR | 10-2007-0122195 A | 12/2007 |
| KR | 10-2014-0095342 A | 8/2014 |
| KR | 10-2014-0141879 A | 12/2014 |
| KR | 10-2017-0028796 A | 3/2017 |
| WO | WO 2016/126141 A1 | 8/2016 |

OTHER PUBLICATIONS

PCT International Search Report, PCT Application No. PCT/KR2018/005282, dated Apr. 3, 2019, 2 pages.

China National Intellectual Property Administration, Office Action, CN Patent Application No. 201880039608.1, dated Jan. 9, 2023, 22 pages.

* cited by examiner

NUCLEIC ACID ANALYSIS APPARATUS USING CARTRIDGE

CROSS-REFERENCE TO RELATED APPLICATIONS

This is a continuation of International Application No. PCT/KR2018/005282 filed on May 8, 2018, which claims priority to Republic of Korea Patent Application No. 10-2017-0060609 filed on May 16, 2017, Republic of Korea Patent Application No. 10-2017-0060610 filed on May 16, 2017, and Republic of Korea Patent Application No. 10-2017-0060611 filed on May 16, 2017, each of which are incorporated by reference in their entirety.

TECHNICAL FIELD

The present disclosure relates to a nucleic acid analysis apparatus and, more particularly, to a nucleic acid analysis apparatus using a cartridge to collectively perform crushing of a sample, nucleic acid extraction, nucleic acid amplification, and nucleic acid detection in a state that the sample is introduced into the cartridge.

BACKGROUND ART

As human life expectancy is prolonged and concerns with health are increasing, the importance of genetic analysis, in vitro diagnostics, gene sequencing, and the like are receiving attention, and demands for related products and services are gradually increasing.

Accordingly, platforms and systems capable of performing lots of inspections in a short time with a small amount of sample are being introduced in markets. For example, microfluidic device platforms using microfluidic technologies such as microfluidics chips and lab-on-a-chip devices are attracting attention. A microfluidic device includes a plurality of microchannels and microchambers designed to allow to control and handle extremely low fluid volumes. The use of the microfluidic device enables to minimize a reaction time of fluids and simultaneously perform the reaction of the fluids and the measurement of a reaction result. Such a microfluidic device can be manufactured by various methods, and various materials may be used according to the manufacturing method.

A determination of a presence of a specific nucleic acid or an amount of the nucleic acid in a sample in gene analysis requires a process of purifying and extracting the sample and then amplifying the nucleic acid to a measurable level. Polymerase chain reaction (PCR) may be one of the most widely used method among various gene amplification methods. Also, fluorescence detection is widely being used as a method for detecting nucleic acids amplified by the PCR.

In order to proceed with the PCR, a series of processes such as capturing cells from a biological sample, crushing the captured cells, extracting nucleic acids from crushed cells, and mixing extracted nucleic acids with PCR reagents are performed. Meanwhile, the sample contains various impurities in addition to the cells from which the nucleic acids are to be extracted, and thus a purification process of removing the impurities from the sample is required before extracting the nucleic acids from the sample.

Conventionally, however, since the processes of the purification of the sample, cell capture, cell destruction, nucleic acid extraction, and the nucleic acid amplification are performed sequentially, an overall process takes a long time to perform and has a problem of poor reproducibility.

Moreover, since an apparatus performing these processes requires a plurality of chambers to proceed with the plurality of unit processes, the apparatus has a complicated structure and may have a problem that the sample can be contaminated during the processes of handling the sample.

Meanwhile, the description in this section merely provides background information of embodiments of the present disclosure and is not intended to specify prior arts of the present disclosure.

SUMMARY

Technical Problem

Provided are a nucleic acid analysis apparatus using a cartridge which can simplify the nucleic acid extraction process through the pretreatment for the sample.

Provided are a nucleic acid analysis apparatus using a cartridge which can collectively perform the crushing of the sample, the cell disruption, and the purification.

Provided are a nucleic acid analysis apparatus using a cartridge which can collectively perform the pretreatment of the sample as well as the extraction, amplification, and detection of nucleic acids.

Additional aspects will be set forth in part in the description which follows and, in part, will be apparent from the description, or may be learned by practice of the presented exemplary embodiments.

Solution to Problem

According to an aspect of an exemplary embodiment, a nucleic acid analysis device includes: a stage, a nucleic acid extraction unit, and a control unit. On the stage, mountable is a cartridge including a plurality of chambers for extracting nucleic acids from a sample including a pretreatment chamber in which the sample is crushed and subject to homogenization, cell disruption, and purification. The nucleic acid extraction unit performs a nucleic acid extraction through crushing of the sample, the cell disruption, and the nucleic acid purification, and a nucleic acid amplification. The nucleic acid extraction unit includes: a magnetic field applying unit for applying a magnetic field to the cartridge so that the crushing and homogenization of the sample, the cell disruption, and the nucleic acid purification may be performed in the cartridge; and a pump driving unit for applying a pressure required for fluid movements between chambers of the cartridge. The control unit controls the stage and the nucleic acid extraction unit so that the nucleic acid extraction through the crushing of the sample, the cell disruption, and the nucleic acid purification, and the nucleic acid amplification are collectively performed.

The magnetic field applying unit may include: a first magnetic field applying unit installed outside the pretreatment chamber in the cartridge for intermittently applying the magnetic field to the pretreatment chamber to move a magnet block contained in the pretreatment chamber and facilitate the crushing and the cell disruption for the sample injected to the pretreatment chamber; and a second magnetic field applying unit installed outside a reaction chamber in the cartridge for applying the magnetic field to the reaction chamber to fix or release magnetic particles contained in the reaction chamber and facilitate cleaning and the nucleic acid extraction.

The nucleic acid extraction unit may include: a first heater installed outside a separation chamber in the cartridge for applying heat to the separation chamber to facilitate a thermal phase separation for a primarily purified liquid supplied from the pretreatment chamber in the cartridge; and a second heater installed outside a nucleic acid amplification chamber in the cartridge for applying heat to the nucleic acid amplification chamber to facilitate a nucleic acid amplification reaction.

The chamber may further include: a pump driven by the pump driving unit to apply air pressure to an air valve module.

The nucleic acid extraction unit may further include: a valve actuating unit comprising an air valve actuator for opening and closing valves in the air valve module, and a liquid valve actuator for opening and closing valves in the liquid valve module.

Each of the valves in the liquid valve module may include: a valve structure made of elastic material and connecting or disconnecting flow paths leading to respective chambers to be connected; and a metal plate installed below the valve structure to move the valve structure up and down according to the magnetic field applied through the liquid valve actuator so as to connect or disconnect the flow paths.

The valve structure may include: a tubular valve column; a valve body positioned at a center of the valve column in a radial direction being spaced apart from an inner wall of the valve column, having a valve dome for opening and closing a flow path in its upper portion and having metal plate attached to its bottom; and a diaphragm connecting the valve body to the inner wall of the valve column and allowing the valve body to move up and down elastically.

The nucleic acid analysis device may further include: a fluorescence detection unit optically detecting fluorescence of a plurality of wavelength bands after the nucleic acids are amplified on the cartridge. The control unit may control operations of the stage, the nucleic acid extraction unit, and the fluorescence detection unit so that the nucleic acid extraction through the crushing of the sample, the cell disruption, and the purification, and the nucleic acid amplification are collectively performed.

The fluorescence detection unit may include: a plurality of light emitters arranged to be parallel to the plurality of nucleic acid amplification chambers disposed in a horizontal direction on the cartridge to output lights of a plurality of color series to be emitted to the plurality of nucleic acid amplification chambers, respectively; a plurality of light receivers, each being arranged to form a pair with respective one of the plurality of light emitters including an optical sensor suitable for receiving the fluorescence emitted from a corresponding one of the plurality of nucleic acid amplification chambers to convert into a fluorescence signal; and a movable filter placed between an assembly of the plurality of light emitters and the plurality of light receivers and the plurality of nucleic acid amplification chambers and installed to be movable in a direction in which the plurality of nucleic acid amplification chambers 161a-161d are arranged to be capable of moving to face the plurality of nucleic acid amplification chambers, and comprising a plurality of filter modules which selectively passes lights of a specific wavelength from the lights of the plurality of color series incident from the plurality of light emitters to direct filtered lights to the plurality of nucleic acid amplification chambers 161a-161d and selectively passes the fluorescence of a specific wavelength out of the fluorescence emitted from the plurality of nucleic acid amplification chambers to direct filtered fluorescence to the plurality of light receivers.

The nucleic acid analysis device may further include: a stage transport unit for loading or unloading the stage to and from a work area in which the magnetic field applying unit, the pump driving unit, the heater, the valve actuating unit, and the fluorescence detection unit are installed.

The stage may be formed to have a through hole at a portion where the cartridge is mounted. The pump driving unit and the liquid valve actuator may be coupled to the cartridge mounted on the stage through the through hole.

The stage transfer unit may separate the stage from the work area when the cartridge is to be mounted or to be detached from the stage, and move the stage to the work area when the cartridge is mounted on the stage.

The magnetic field applying unit, the heater, the pump driving unit, the valve actuating unit, and the fluorescence detection unit may be separated from the work area before the stage is loaded into or unloaded from the work area, while being moved and coupled to the work area when the stage is loaded into the work area.

Advantageous Effects

The nucleic acid analysis apparatus according to the present disclosure can collectively perform the nucleic acid extraction through the crushing of the injected sample, the cell disruption, and the purification as well as the nucleic acid amplification using a cartridge.

Since the pretreatment chamber in the cartridge can collectively perform the crushing of the sample, the cell disruption, and the purification, the nucleic acid extraction process can be simplified through the pretreatment of the sample.

The nucleic acid analysis apparatus according to the present disclosure can integratively perform the nucleic acid test through the nucleic acid extraction and amplification using the cartridge. Since the fluorescence detector is installed before the nucleic acid amplification chamber in which nucleic acid amplification is performed after the nucleic acid extraction on the cartridge, the nucleic acids can be detected by optically detecting the fluorescence of a plurality of wavelength bands after the nucleic acid amplification is performed.

According to the fluorescence detection unit of the present disclosure, the fluorescence of a plurality of wavelength bands can be optically detected while the filter modules are moved with respect to the light emitter and the light receiver.

The fluorescence detection unit according to the present disclosure can optically detect the fluorescence of a plurality of wavelength bands emitting from each of the chambers while sequentially moving the filter modules along the plurality of nucleic acid amplification chambers arranged in a line.

Since only the filter modules move with respect to the light emitter unit and the light receiver which are fixed, the fluorescence detection unit according to the present disclosure can stably detect the fluorescence signal with minimized structure of moving components in the optical system.

That is, since only the filter modules move in the fluorescence detection unit, the optical system can be simplified and compact while being capable of stably detecting the fluorescence signal.

Further advantages and areas of applicability will become apparent from the description of exemplary embodiments provided herein.

DETAILED DESCRIPTION

Figure 1:
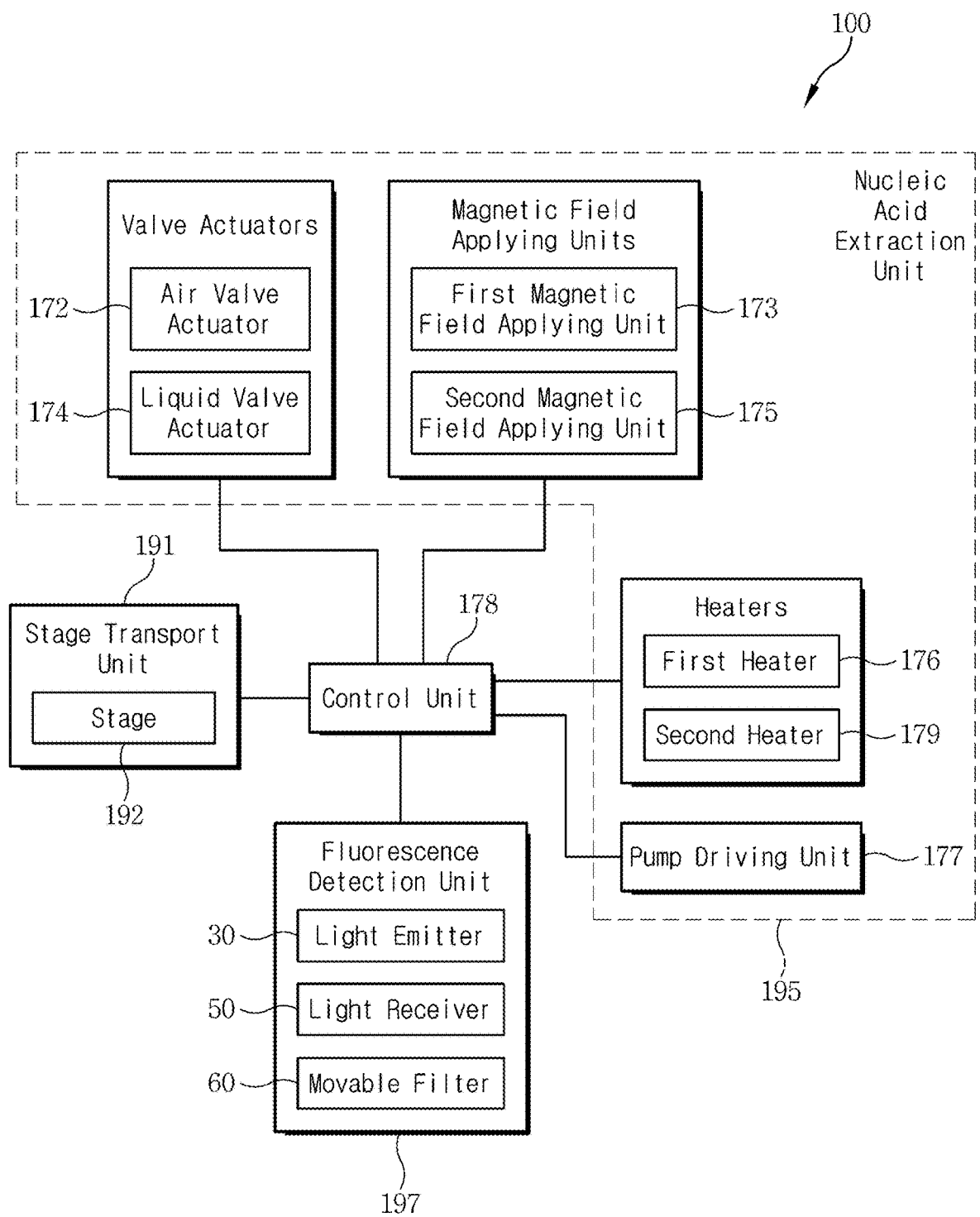
FIG. 1 is a block diagram of a nucleic acid analysis apparatus using a cartridge according to an exemplary embodiment of the present disclosure.

For a clearer understanding of the features and advantages of the present disclosure, exemplary embodiments of the present disclosure will be described in detail with reference to the accompanied drawings.

In the following description and the accompanied drawings, detailed descriptions of well-known functions or configuration that may obscure the subject matter of the present disclosure will be omitted for simplicity. Also, it is to be noted that the same components are designated by the same reference numerals throughout the drawings.

The terms and words used in the following description and appended claims are not necessarily to be construed in an ordinary sense or a dictionary meaning, and may be appropriately defined herein to be used as terms for describing the present disclosure in the best way possible. Such terms and words should be construed as meaning and concept consistent with the technical idea of the present disclosure. The embodiments described in this specification and the configurations shown in the drawings are merely preferred embodiments of the present disclosure and are not intended to limit the technical idea of the present disclosure. Therefore, it should be understood that there may exist various equivalents and modifications which may substitute the exemplary embodiments at the time of filing of the present application.

The terminologies including ordinals such as "first" and "second" designated for explaining various components in this specification are used to discriminate a component from the other ones but are not intended to be limiting to a specific component. For example, a second component may be referred to as a first component and, similarly, a first component may also be referred to as a second component without departing from the scope of the present disclosure.

When a component is referred to as being "connected" or "coupled" to another component, it means that the component is connected or may be connected logically or physically to the other component. In other words, it is to be understood that the component or may be connected or coupled to the other component indirectly through an object therebetween instead of being directly connected or coupled to the other component.

The terminologies are used herein for the purpose of describing particular embodiments only and are not intended to limit the disclosure. The singular forms include plural referents unless the context clearly dictates otherwise. Also, the expressions "~comprises," "~includes," "~constructed," "~configured" are used to refer a presence of a combination of enumerated features, numbers, processing steps, operations, elements, or components, but are not intended to exclude a possibility of a presence or addition of another feature, number, processing step, operation, element, or component.

Exemplary embodiments of the present disclosure will now be described in detail with reference to the accompanied drawings.

Figure 2:
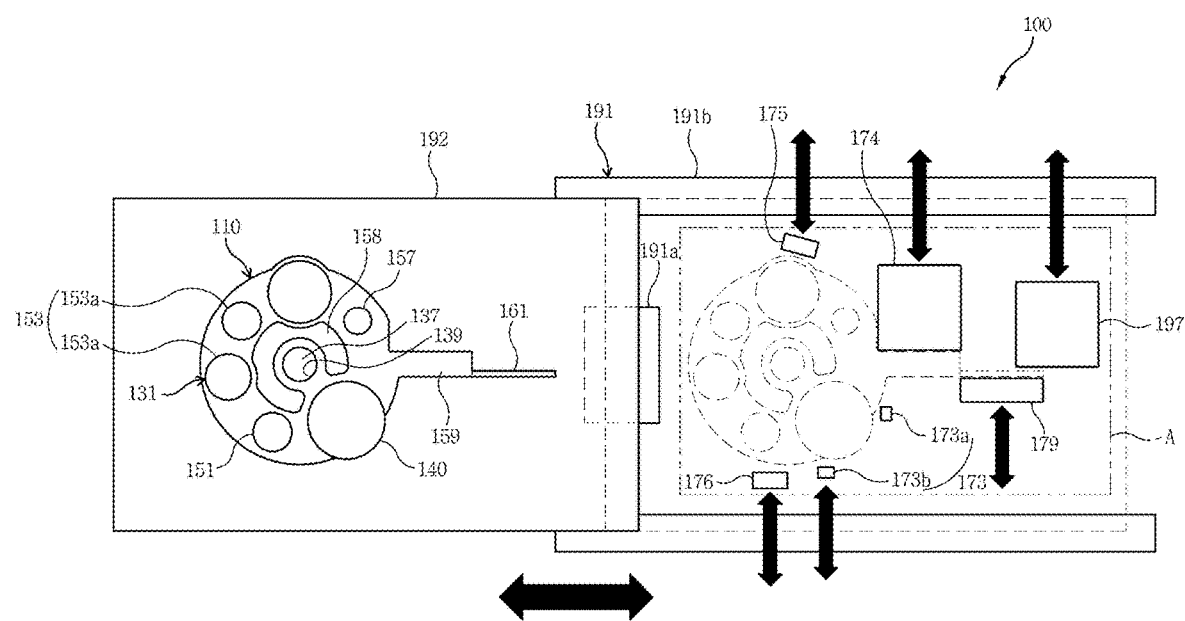
FIGS. 2 and 3 are schematic diagrams illustrating the nucleic acid analysis apparatus of FIG. 1.
Figure 3:
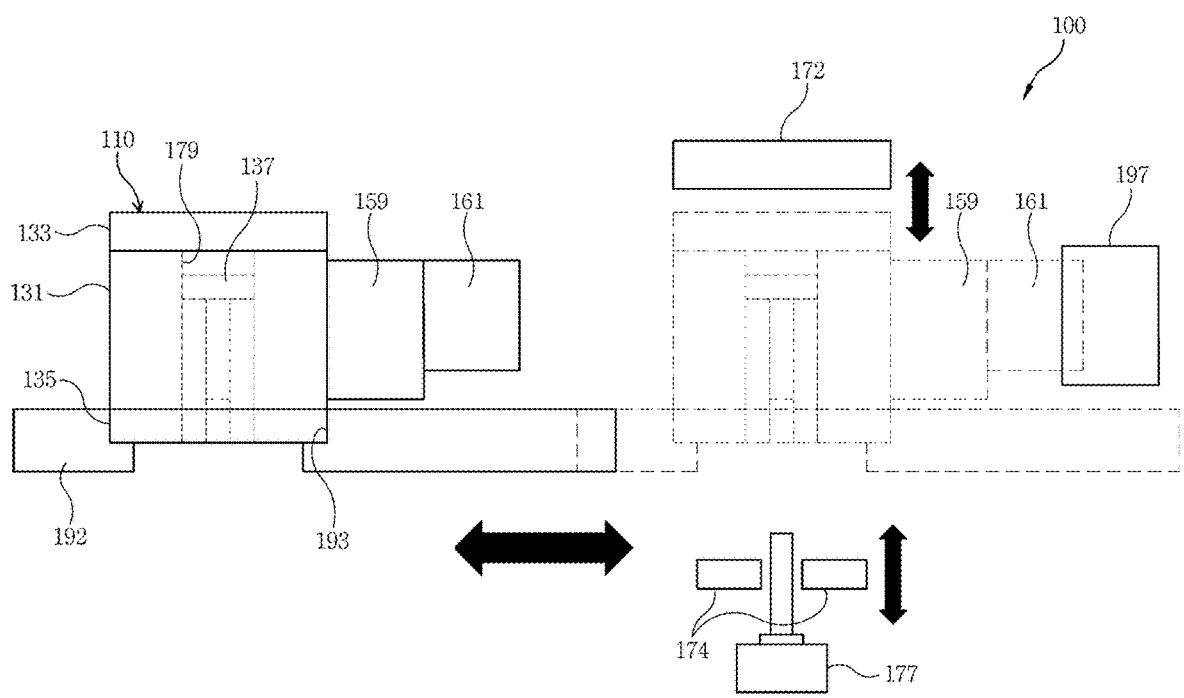
Figure 4:
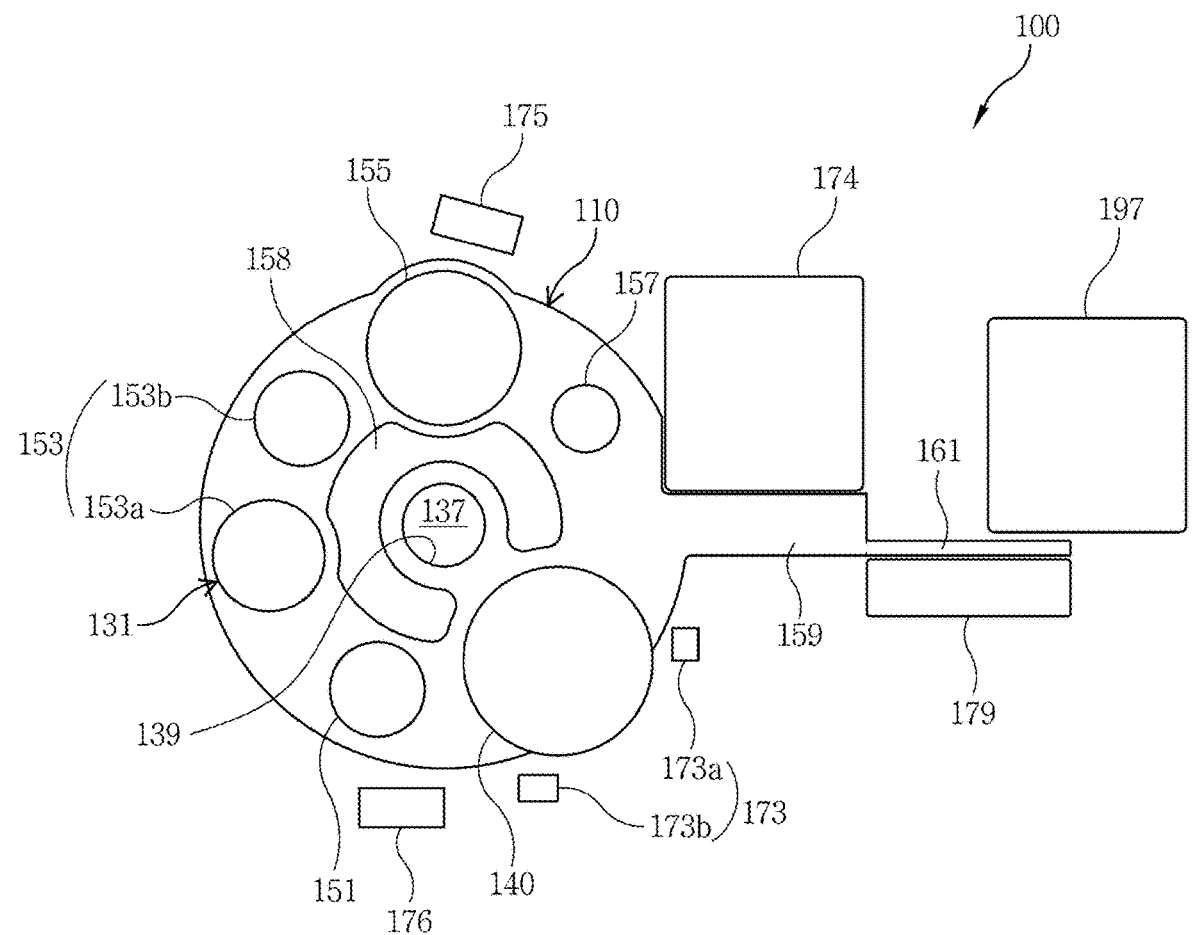
FIG. 4 is an enlarged schematic view of portion A in FIG. 2.
Figure 5:
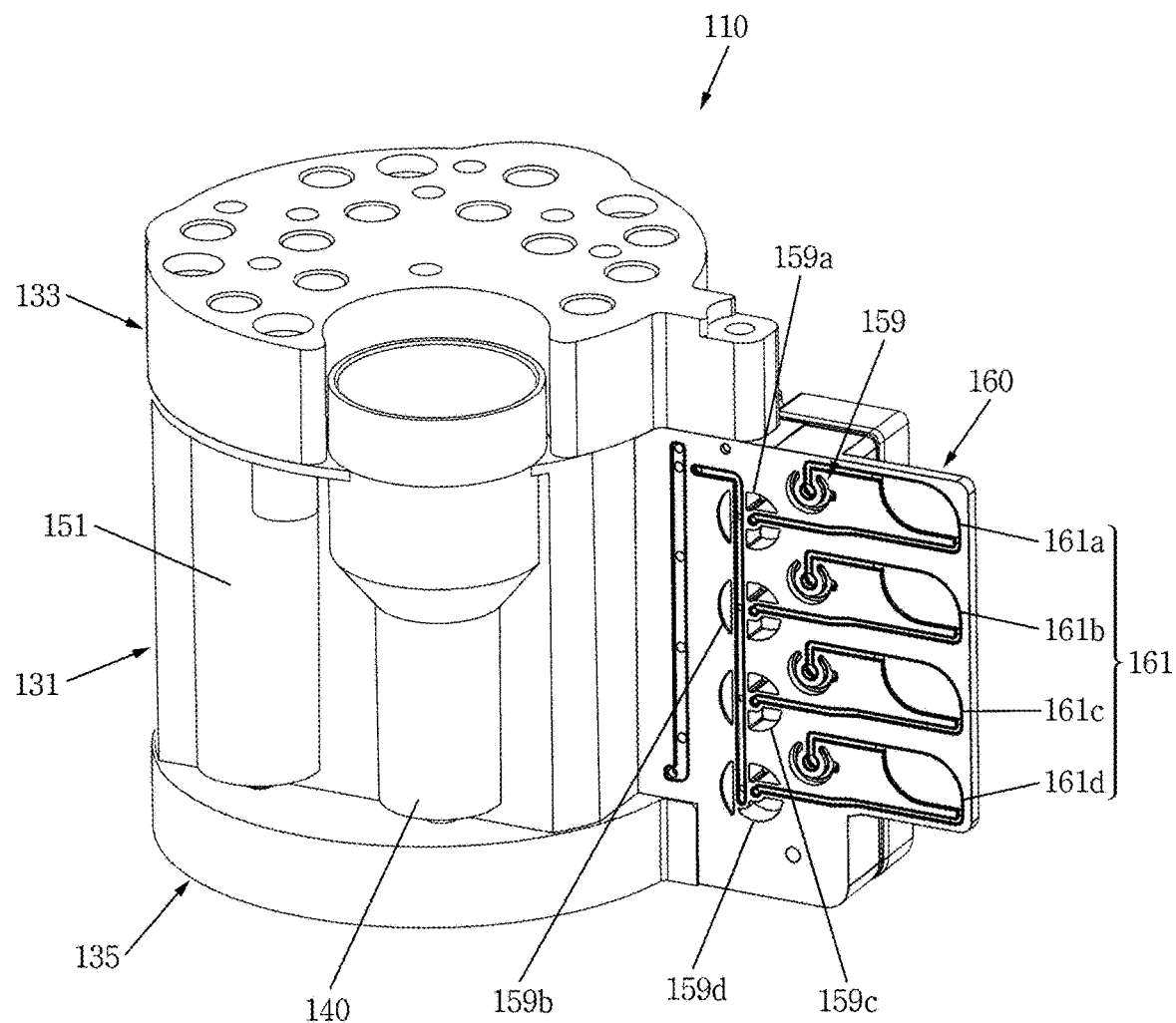
FIG. 5 is a perspective view of the nucleic acid extraction cartridge shown in FIG. 4.

FIG. 1 is a block diagram of a nucleic acid analysis apparatus using a cartridge according to an exemplary embodiment of the present disclosure. FIGS. 2 and 3 are schematic diagrams illustrating the nucleic acid analysis apparatus of FIG. 1. FIG. 4 is an enlarged schematic view of portion A in FIG. 2. FIG. 5 is a perspective view of a nucleic acid extraction cartridge shown in FIG. 4.

Referring to FIGS. 1-5, a nucleic acid analysis apparatus 100 according to an exemplary embodiment of the present embodiment is a point-of-care testing (POCT) apparatus using a nucleic acid extracting cartridge 110, and collectively performs a pretreatment of a sample injected into the cartridge 110, a nucleic acid extraction and purification, a nucleic acid amplification, and a fluorescence detection.

The nucleic acid analysis apparatus 100 according to the present embodiment includes a stage 192, a nucleic acid extraction unit 195, a fluorescence detection unit 197, and a control unit 178. A cartridge 110 is mounted on the stage 192. The cartridge 110 includes a plurality of chambers for extracting nucleic acids from the sample, including a pretreatment chamber 140 in which the injected sample is crushed and undergoes sample homogenization, cell disruption, and nucleic acid purification. The nucleic acid extraction unit 195 performs the nucleic acid extraction through the crushing of the injected sample, the sample homogenization, the cell disruption, and the nucleic acid purification, and performs the nucleic acid amplification. The fluorescence detection unit 197 optically detects fluorescence of a plurality of wavelengths for the nucleic acids amplified on the cartridge 110. The control unit 178 controls the operation of the stage 192, the nucleic acid extraction unit 195, and the fluorescence detection unit 197 such that the nucleic acid extraction through the crushing of the injected sample, the cell disruption, and the purification, as well as the nucleic acid amplification and the fluorescence detection are collectively performed.

The nucleic acid extraction unit 195 may include magnetic field applying units 173 and 175, a pump driving unit 177, heaters 176 and 179, and valve actuators 172 and 174. The heaters 176 and 179 may include a first heater 176 and a second heater 179. The valve actuators 172 and 174 may include an air valve actuator 172 and a liquid valve actuator 174.

The fluorescence detection unit 197 may include a plurality of light emitters 30, a plurality of light receivers 50, and a movable filter 60.

The nucleic acid analysis apparatus 100 according to the present embodiment may further include a stage transport unit 191.

The cartridge 110 may be mounted on the stage 192. In a state that the cartridge 110 is mounted on the stage 192, the pretreatment of the sample, the nucleic acid extraction, and the nucleic acid amplification may be performed collectively. A through hole 193 is formed in the stage 192 at a portion where the cartridge 110 is mounted. The pump driving unit 177 and the liquid valve actuator 174 can be coupled to the cartridge 110 mounted on the stage 192 through the through hole 193. That is, the pump driving unit 177 is coupled to the pump 137 of the cartridge 110 through the through hole 193. The liquid valve actuator 174 is coupled to the liquid valve module 135 of the cartridge 110 through the through hole 193.

The stage transport unit 191 loads or unloads the stage 192 to and from a work area in which the magnetic field applying units 173 and 175, the pump driving unit 177, the heaters 176 and 179, the valve actuators 172 and 174, and the fluorescence detection unit 197 are installed. When the cartridge 110 provided with the sample is mounted on the stage 192, the stage transport unit 191 transfers the stage 192 to the work area under the control of the control unit 178 to load the cartridge 110. Upon completion of the pretreatment the sample provided to the cartridge 110, the nucleic acid extraction, the nucleic acid amplification, and the fluorescence detection, the stage transport unit 191 transfers the stage 192 out of the work area to unload the cartridge 110. The stage transport unit 191 may include, for example, a stepping motor 191a suitable for transferring the stage 192 and a transport rail 191b suitable for guiding the transport of the stage 192 according to the driving of the stepping motor 191a.

The magnetic field applying units 173 and 175, the pump driving unit 177, the heaters 176 and 179, the valve actuators 172 and 174, and the fluorescence detection unit 197 are installed in the work area where the pretreatment, the nucleic acid extraction, the nucleic acid amplification, and fluorescence detection are performed for the sample provided to the cartridge 110 loaded by the stage transport unit 191. The magnetic field applying units 173 and 175, the pump driving unit 177, the heaters 176 and 179, the valve actuators 172 and 174, and the fluorescence detection unit 197 are movably installed. Also, the control unit 178 may be installed together in the work area.

The cartridge 110, in which the injected sample undergoes the cell disruption, the nucleic acid extraction, the nucleic acid amplification, and the fluorescence detection are collectively performed, is for single use only. The sample may be a biochemical one requiring the pretreatment, such as stool, tissue, sputum. Other examples of the sample may include blood, urine, saliva, semen, spinal fluid, mucus, and the like.

The cartridge 110 includes a chamber module 131, an air valve module 133, and a liquid valve module 135. The chamber module 131 includes a plurality of chambers for extracting the nucleic acids from the sample, including a pretreatment chamber 140 in which the crushing and homogenization of the ample, the cell disruption, and the nucleic acid purification are performed. The air valve module 133 is installed on the upper part of the chamber module 131 and controls a pressure required to move fluid between the chambers. The liquid valve module 135 is installed below the chamber module 131 and moves the fluid between the chambers.

The plurality of chambers in the chamber module 131 may include the pretreatment chamber 140, a separation chamber 151, a cleaning chamber 153, an elution chamber 157, a reaction chamber 155, a nucleic acid amplification reagent chamber 159, and a nucleic acid amplification chamber 161. The chamber module 131 may further include a waste chamber 158 in which used reagents and residue are discarded. The chamber module 131 may be provided with a pump 137, in its central portion, suitable for providing air pressure required to drive the air valve module 133. For example, the pretreatment chamber 140, the separation chamber 151, the cleaning chamber 153, the reaction chamber 155, and the elution chamber 157 may be disposed around the pump 137. The nucleic acid amplification reagent chamber 159 and the nucleic acid amplification chamber 161 may be disposed between the pretreatment chamber 140 and the elution chamber 157 and protrude outward with respect to the other chambers. The waste chamber 158 may be disposed between the pump 137 and the other chambers.

The pump 137 is installed in the central portion of the chamber module 131 and moves up and down by the pump driving unit 177 to provide the air pressure required by the plurality of chambers. The chamber module 131 has a pump hole 139 formed vertically in its central portion to allow the pump 137 to move up and down and provide the required pressure to the plurality of chambers. According to the present embodiment, the air pressure may be delivered to the plurality of chambers by a rise of the pump 137.

The magnetic field applying units 173 and 175 apply magnetic fields to the cartridge 110 so that the crushing and homogenization of the injected sample, the cell disruption, and the nucleic acid purification may be performed in the cartridge 110. The magnetic field applying units 173 and 175 include a first magnetic field applying unit 173 and a second magnetic field applying unit 175. The first magnetic field applying unit 173 is installed outside the pretreatment chamber 140 and intermittently applies the magnetic field to the pretreatment chamber 140 to move a magnet block contained in the pretreatment chamber 140 and facilitate the pretreatment process for the sample provided to the pretreatment chamber 140. The first magnetic field applying unit 173 may be divided into a plurality of segments installed at different positions to facilitate the movement of the magnet block contained in the pretreatment chamber 140. For example, the first magnetic field applying unit 173 may include a first magnetic field applying segment 173a and a second magnetic field applying segment 173b.

The second magnetic field applying unit 175 is installed outside the reaction chamber 155 and applies the magnetic field to the reaction chamber 155 to fix or release magnetic particles contained in the reaction chamber 155 and facilitate cleaning and nucleic acid elution processes.

The magnetic field applying units 173 and 175 are installed to be movable to the work area. That is, the magnetic field applying units 173 and 175 are located to be spaced apart from the cartridge 110 when the cartridge 110 is being loaded to the work area so as not to physically interfere with the cartridge 110. When the cartridge 110 is completely loaded to the work area, the magnetic field applying units 173 and 175 move closer to the pretreatment chamber 140 and the reaction chamber 155, respectively. After the nucleic acid extraction, the nucleic acid amplification, and the fluorescence detection using the cartridge 110 is completed, the magnetic field applying units 173 and 175 are separated from the pretreatment chamber 140 and the reaction chamber 155, respectively, so that the cartridge 110 can be unloaded from the work area.

The heaters 176 and 179 include the first heater 176 and the second heater 179.

The first heater 176 is installed outside the separation chamber 151 and applies heat to the separation chamber 151 to facilitate a separation process for a primarily purified liquid supplied from the pretreatment chamber 140.

The second heater 179 is installed outside the nucleic acid amplification chamber 161 and applies heat to the nucleic acid amplification chamber 161 to facilitate a nucleic acid amplification reaction.

The heaters 176 and 179 are installed to be movable to the work area. That is, the heaters 176 and 179 are located to be spaced apart from the cartridge 110 when the cartridge 110 is being loaded to the work area so as not to physically interfere with the cartridge 110. When the cartridge 110 is completely loaded to the work area, heaters 176 and 179 move closer to the separation chamber 151 and the nucleic acid amplification chamber 161, respectively. After the nucleic acid extraction, the nucleic acid amplification, and the fluorescence detection using the cartridge 110 is completed, the heaters 176 and 179 are separated from the separation chamber 151 and the nucleic acid amplification chamber 161, respectively, so that the cartridge 110 can be unloaded from the work area.

The pump driving unit 177 may generates a force required for fluid movement between the chambers of the cartridge 110. That is, the pump driving unit 177 drives the pump 137 so that the pump 137 applies the air pressure to the air valve module 133 of the cartridge 110. The pump driving unit 177 may be installed under the work area or may be installed to be movable to under the cartridge 110 having moved to the work area. For example, a stepping motor may be used as the pump driving unit 177.

The valve actuators 172 and 174 include the air valve actuator 172 and the liquid valve actuator 174.

The air valve actuator 172 opens and closes valves of the air valve module 133. The air valve actuator 172 is installed to be located above the work area and is coupled to the air valve module 133 of the cartridge 110 having moved to the work area. The air valve actuator 172 is installed to be movable to a space above the cartridge 110 having moved to the work area. For example, in the case that the valves of the air valve module 133 are opened and closed by a magnetic force, the air valve actuator 172 includes electromagnets of which number corresponds to a number of the valves of the air valve module 133.

The liquid valve actuator 174 opens and closes the valves of the liquid valve module 135. The liquid valve actuator 174 may be located under the work area and may be coupled to the liquid valve module 135 of the cartridge 110 through the through hole 193 of the stage 192 having moved to the work area. The liquid valve actuator 174 is installed to be movable to a space under the cartridge 110 having moved to the work area. For example, in the case that the valves of the liquid valve module 135 are opened and closed by a magnetic force, the liquid valve actuator 174 includes electromagnets of which number corresponds to a number of the valves of the liquid valve module 135. The opening and closing of the valves of the liquid valve module 135 by the electromagnets of the liquid valve actuator 174 will be described below.

The control unit 178 is a microprocessor that performs overall control of the operations of the nucleic acid analysis apparatus 100. When the cartridge 110 provided with the sample is mounted to the stage 192, the control unit 178 controls the stage transport unit 191, the nucleic acid extraction unit 195, and the fluorescence detection unit 197 such that the pretreatment of the sample, the nucleic acid extraction, the nucleic acid amplification, and the fluorescence detection are collectively performed.

For the nucleic acid extraction, the nucleic acid amplification, and the fluorescence detection, the nucleic acid analysis apparatus 100 according to the present embodiment is driven as follows.

First, the stage 192 is separated from the work area by the stage transport unit 191 so that the cartridge 110 provided with the sample can be mounted on the stage 192. At this time, the magnetic field applying units 173 and 175, the heaters 176 and 179, the pump driving unit 177, the valve actuators 172 and 174 and the fluorescence detection unit 197 are separated from the work area to prevent interference with the cartridge 110.

When the cartridge 110 provided with the sample is mounted in the through hole 193 of the stage 192, the stage transport unit 191 loads the cartridge 110 mounted on the stage 192 into the work area under the control of the control unit 178.

After the cartridge 110 is loaded into the work area, the magnetic field applying units 173 and 175, the heaters 176 and 179, the pump driving unit 177, the valve actuators 172 and 174, and the fluorescence detection unit 197 moves to the work area to be close to the loaded cartridge 110 under the control of the control unit 178. As a result, the first magnetic field applying unit 173 is located to be close to the pretreatment chamber 140 of the cartridge 110. The second magnetic field applying unit 175 is located to be close to the reaction chamber 155. The first heater 176 is located to be close to the separation chamber 151. The second heater 179 is located to be close to one side of the nucleic acid amplification chamber 161. The pump driving unit 177 is coupled to the pump 137 of the cartridge 110. The valve actuators 172 and 174 are coupled to the air valve module 133 and the liquid valve module 135, respectively. The fluorescence detection unit 197 is located to be close to the other side of the nucleic acid amplification chamber 161.

Then, the control unit 178 controls operations of the magnetic field applying units 173 and 175, the heaters 176 and 179, the pump driving unit 177, the valve actuators 172 and 174, and the fluorescence detection unit 197 so that the pretreatment, the nucleic acid extraction, the nucleic acid amplification, and the fluorescence detection are collectively performed for the sample provided to the cartridge 110. The pretreatment of the sample provided to the cartridge 110, the nucleic acid extraction, the nucleic acid amplification, and the fluorescence detection will be described below.

Upon completion of the fluorescence detection, the control unit 178 unloads the cartridge 110 from the work area. That is, the control unit 178 makes the magnetic field applying units 173 and 175, the heaters 176 and 179, the pump driving unit 177, the valve actuators 172 and 174, and the fluorescence detection unit 197 to be separated from the cartridge 110 and move out of the work area. Then, the control unit 178 controls the stage transport unit 191 to unload the cartridge 110 of the stage 192 out of the work area.

Since the nucleic acid analysis apparatus 100 according to the present embodiment includes the nucleic acid extraction unit 195 and the fluorescence detection unit 197, the nucleic acid analysis apparatus 100 can perform the fluorescence detection process also, after the nucleic acid amplification, for the nucleic acid in the nucleic acid amplification chamber 161 of the cartridge 110 on the stage 192. Consequently, the control unit 178 unloads the cartridge 110 from the work area after the nucleic acid extraction, the nucleic acid amplification, and the fluorescence detection are collectively performed.

Figure 6:
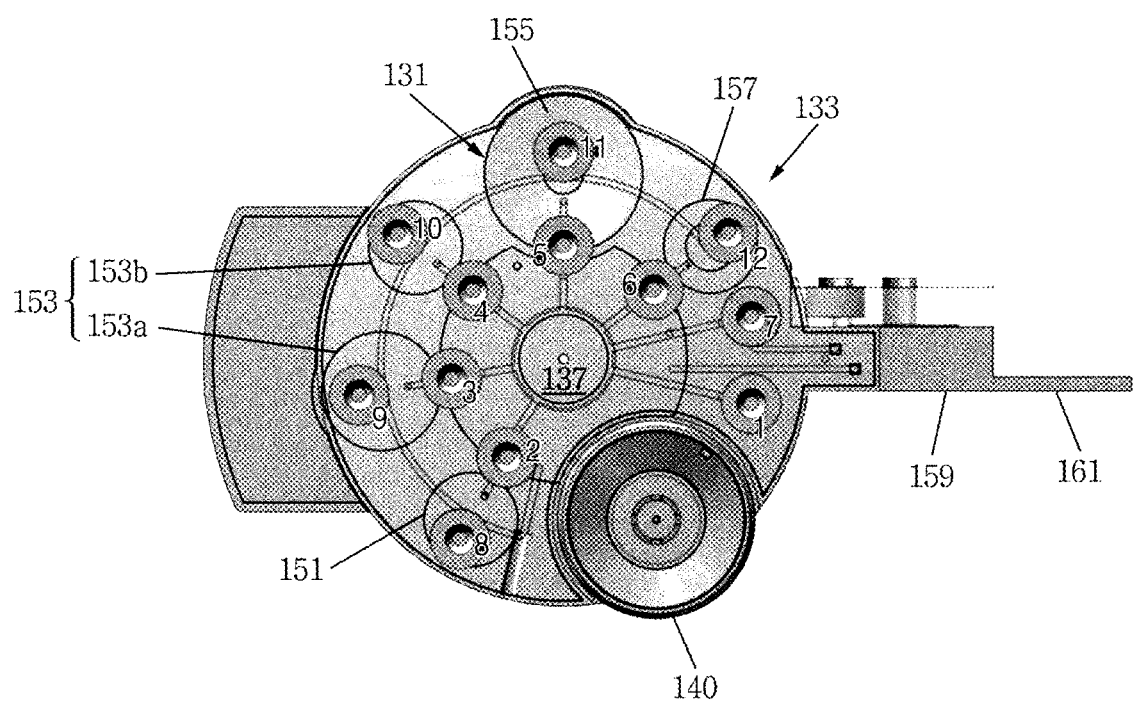
FIG. 6 is a planar view of an air valve module shown in FIG. 5.
Figure 7:
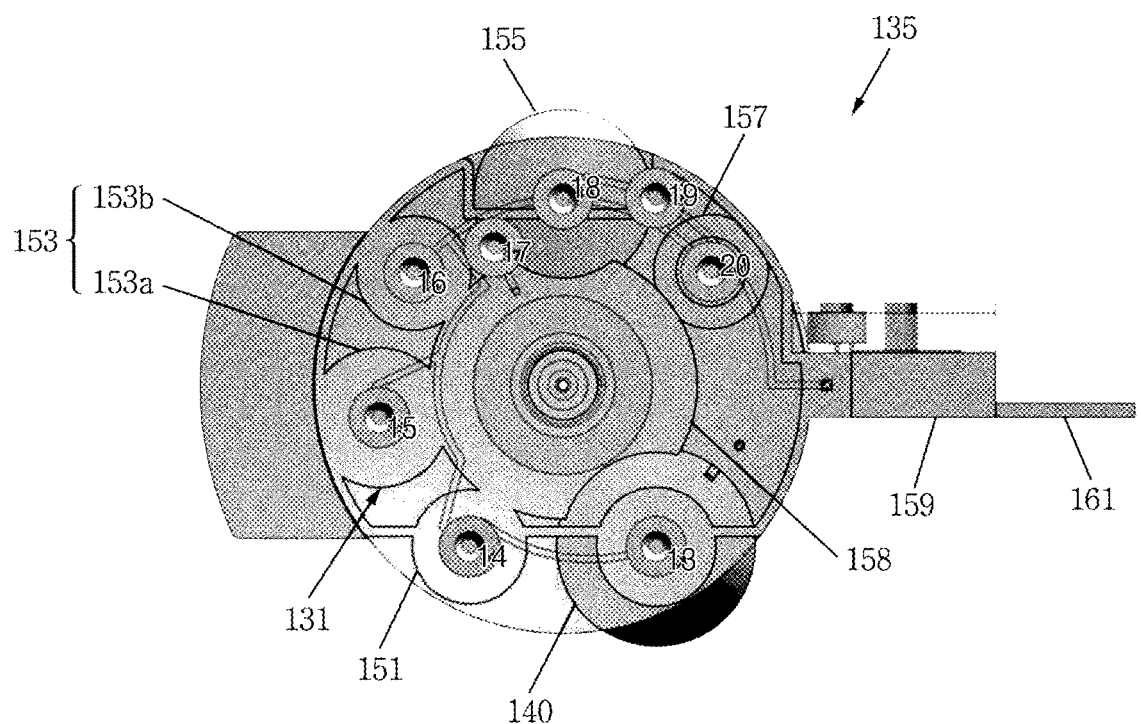
FIGS. 7 and 8 are planar views of a liquid valve module shown in FIG. 5.
Figure 8:
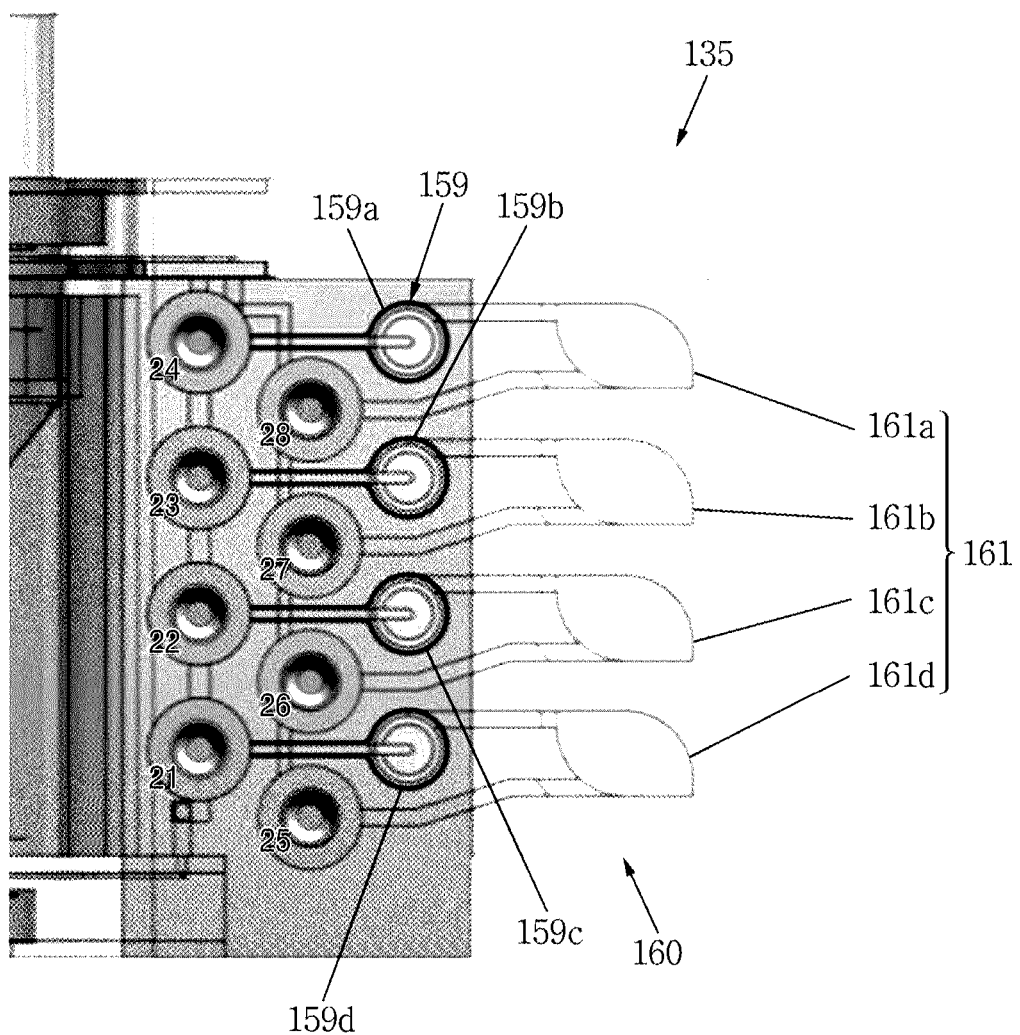
Figure 9:
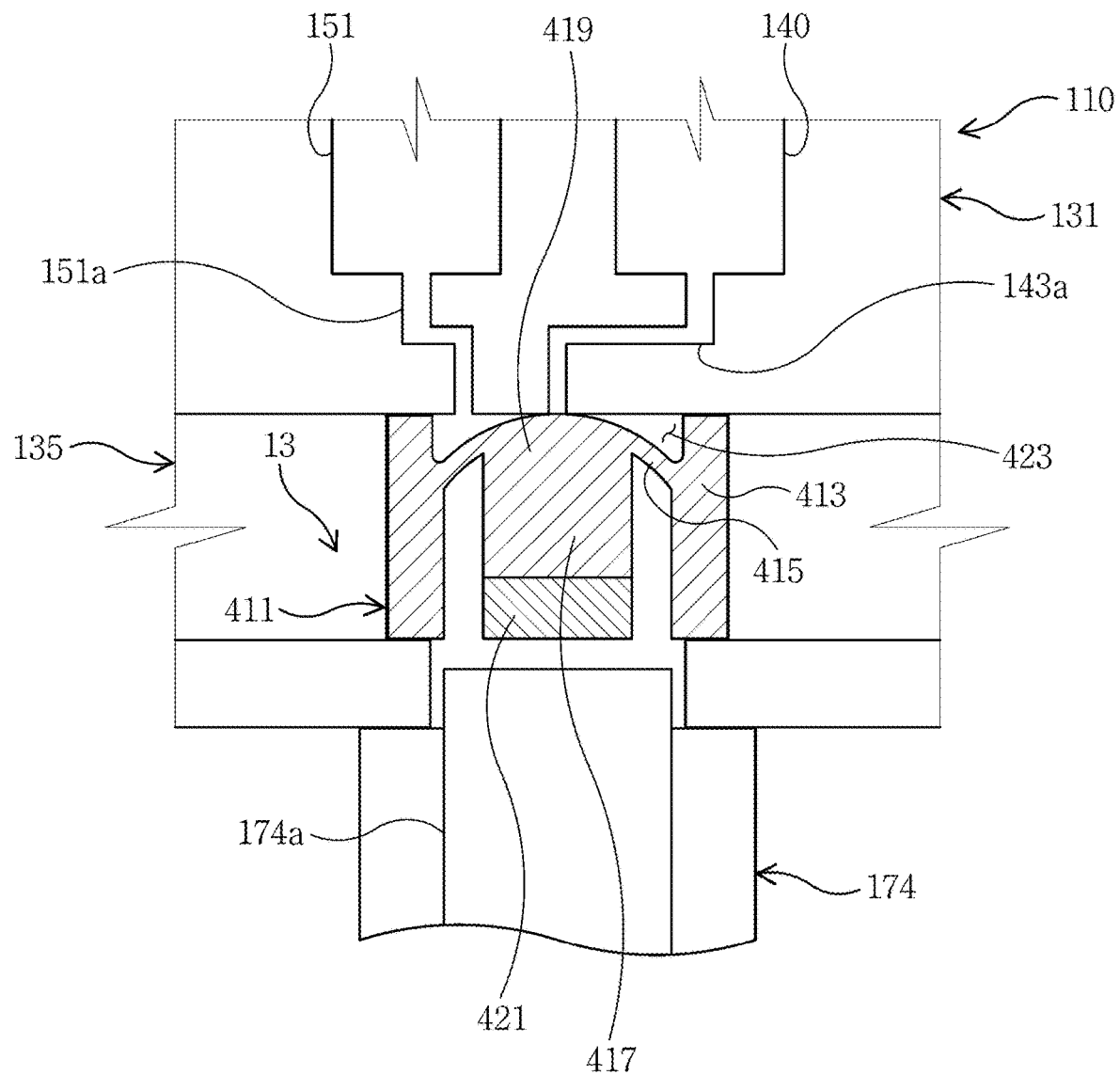
FIGS. 9 and 10 illustrate a state that an electromagnet of a liquid valve actuator is installed in a valve of the liquid valve module.
Figure 10:
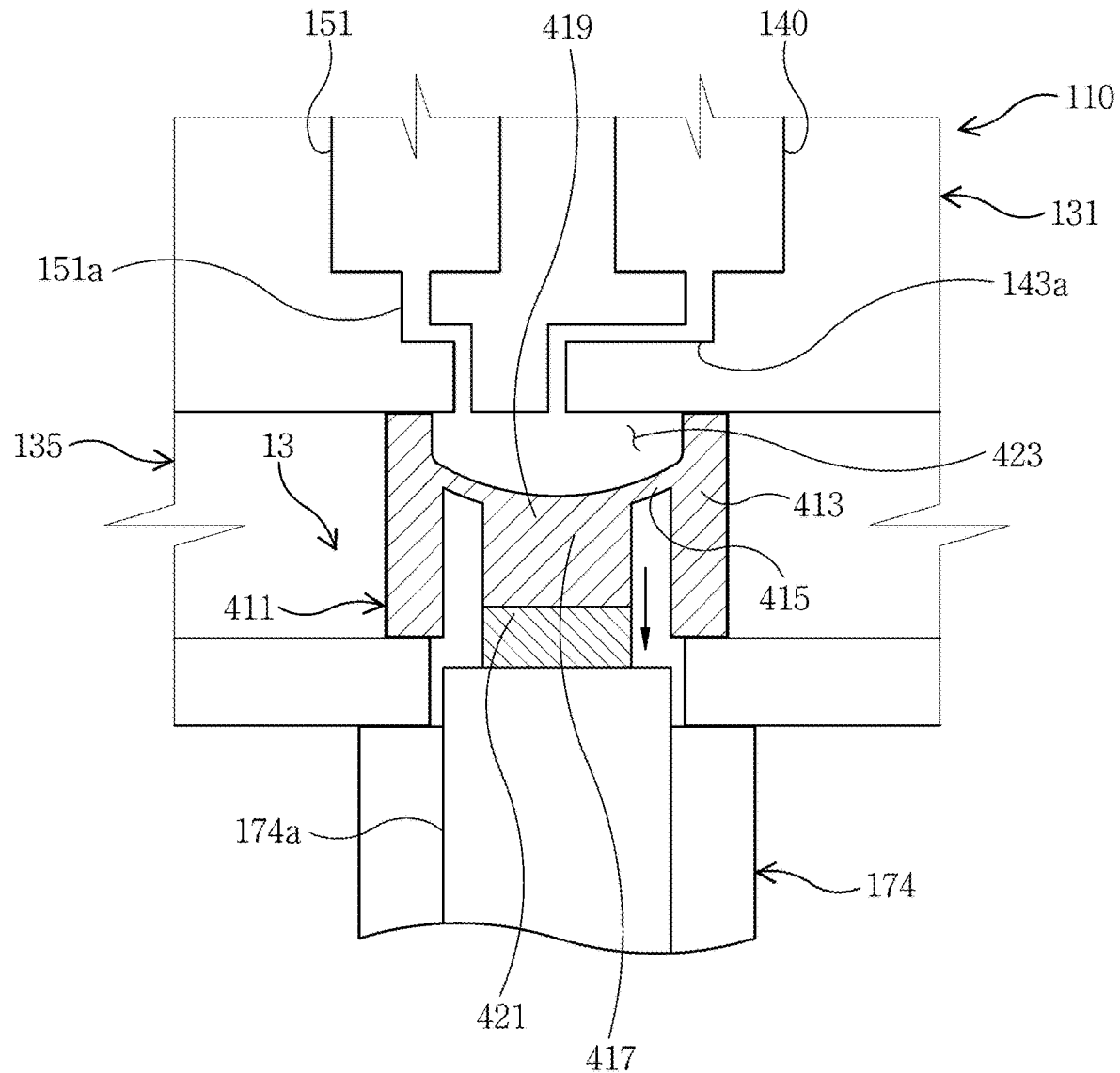
Figure 11:
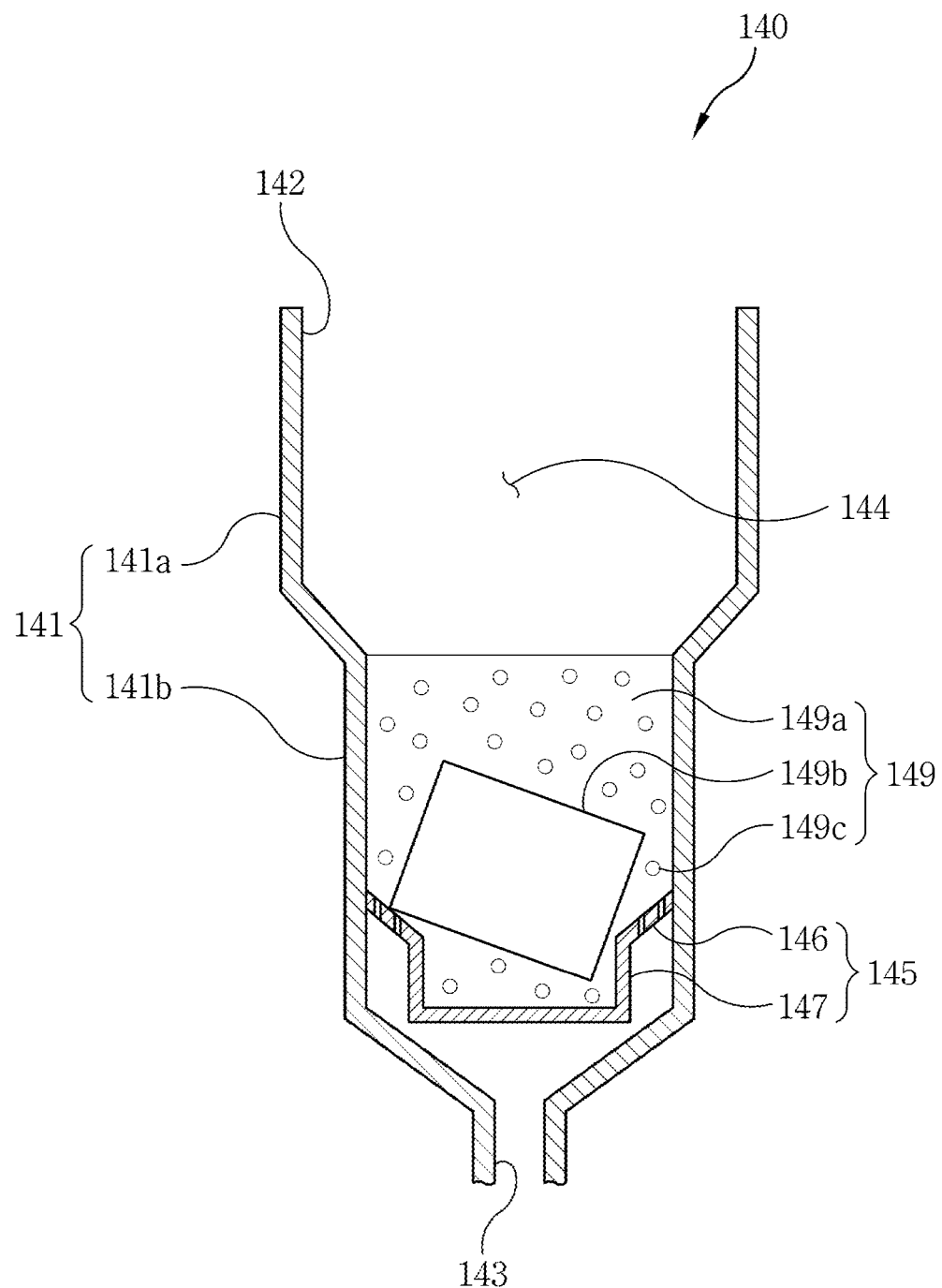
FIG. 11 illustrates a pretreatment chamber shown in FIG. 5.

The cartridge 110 according to the present embodiment will now be described with reference to FIGS. 5 through 11. FIG. 6 is a planar view of the air valve module 133 shown in FIG. 5. FIGS. 7 and 8 are planar views of the liquid valve module 135 shown in FIG. 5. FIGS. 9 and 10 illustrates a state that an electromagnet 174a of the liquid valve actuator 174 is installed in a valve 13 of the liquid valve module 135. FIG. 11 illustrates the pretreatment chamber 140 shown in FIG. 5.

The cartridge 110 includes the chamber module 131, the air valve module 133, and the liquid valve module 137 as described above.

The chamber module 131 may include the pretreatment chamber 140, the separation chamber 151, the cleaning chamber 153, the elution chamber 157, the reaction chamber 155, the nucleic acid amplification reagent chamber 159, the nucleic acid amplification chamber 161, and the waste chamber 158. The pretreatment chamber 140, the separation chamber 151, the cleaning chamber 153, the reaction chamber 155, and the elution chamber 157 may be sequentially arranged around the pump 137. The waste chamber 158 may be disposed between the other chambers and the pump 137.

The pretreatment chamber 140 contains pretreatment components 149 that includes a pretreatment fluid 149a, a magnet block 149b or cell disruption particles 149c. The pretreatment chamber 140 discharges a primarily purified liquid containing the nucleic acids to the separation chamber 151 after the crushing of the injected sample and the cell disruption.

The pretreatment chamber 140 may include a chamber body 141 and a cup filter 145 disposed in a lower portion of the chamber body 141, and may contain the pretreatment components 149 inside the chamber body 141 on the cup filter 145. The chamber body 141 has an internal space 144 in which the injected sample is crushed and undergoes the homogenization and the cell disruption. The cup filter 145 is defines a lower end of the inner space 144 and filters the primarily purified liquid to selectively pass the nucleic acid flown out of disrupted cells.

The chamber body 141 includes an upper body 141a and a lower body 141b. The upper body 141a has an inlet 142 formed in its upper portion for supplying the pretreatment components 149 and the sample. The lower body 141b extends from a portion of the upper body 141a and has an inner diameter smaller than that of the upper body 141a. The lower body 141b has an outlet 143 through which the primarily purified liquid is discharged. The cup filter 145 is installed on inner wall of the lower body 141b.

The reason why an inner diameter of the upper body 141a is made larger than the inner diameter of the lower body 141b is to facilitate the supply of the pretreatment member 149 and the sample through the inlet 142.

The pretreatment member 149 includes the pretreatment fluid 149a, the magnet block 149b or the cell disruption particles 149c as described above.

Any pretreatment used for molecular diagnostics can be used as the pretreatment fluid 149a in the apparatus according to the present disclosure. When the sample is provided to the pretreatment liquid 149a, 0.01 to 0.1 wt % of the sample may be introduced to 100 wt % of the pretreatment fluid 149a. If the sample is introduced at less than 0.01 wt %, the yield may be too low and inefficient. If the sample is introduced in excess of 0.1 wt %, the homogenization may not be achieved properly. Therefore, it is preferable to adjust the amount of the pretreatment fluid 149a and the sample within the aforementioned range.

The cell disruption particle 149c are made of non-magnetic material, and glass beads, for example, may be used for the cell disruption particle 149c. Besides, the cell disruption particles 149c made of silica, latex, or a polymeric material.

The magnet block 149b moves in the pretreatment fluid 149a by an intermittently applied magnetic force to generate movements of the cell disruption particles 149c, which results in the crushing and the homogenization of the sample. Furthermore, the cell disruption particles 149c which move according to the movement of the magnet block 149b destroy the cells contained in the sample and allow the nucleic acids to flow out of the cells.

The cell disruption particles 149c are larger than pores formed in the cup filter 145 so as not to pass through the cup filter 145 during a first purification process. For example, the size of the cell disruption particles 149c may be 50 m or larger.

The magnet block 149b may have a size suitable for being remained inside the lower body 141b.

The pretreatment components 149 are contained in the internal space 144 of the chamber body 141 located above the cup filter 145. The cup filter 145 includes a filter portion 146 and a cup portion 147. The filter portion 146 extends obliquely downward from a binding position with the inner wall of the chamber body 141 and filters the contents of the pretreatment chamber to selectively pass the primarily purified liquid containing nucleic acids. The cup portion 147 extends from the filter portion 146 allows the residue remaining after the filtering to be precipitated.

The cup portion 147 may be disposed at a central position, in a radial direction, of the internal space 144 of the chamber body 141. The filter portion 146 extends obliquely upward from an upper end of the cup portion 147 and is coupled to the inner wall of the chamber body 141. The filter portion 146 is formed to have a tapered surface, and pores are formed in the tapered surface so as to pass the primarily purified liquid.

Since the filter portion 146 is formed to have the tapered surface which guides the materials towards the cup portion 147, the residue having not passed through the filter portion 146 moves along the tapered surface of the filter portion 146 onto the cup portion 147 to be precipitated. Thus, it is possible to prevent the residue that has not passed through the filter portion 146 to close the pores of the filter portion 146 and delay or block the primary purification in the primary purification process.

Meanwhile, the primarily purified liquid obtained through the primary purification process contains some residue in addition to the nucleic acid. That is, the primarily purified liquid contains the nucleic acid, the pretreatment fluid 149a, and the residue.

The separation chamber 151 receives the primarily purified liquid from the pretreatment chamber 140 and performs a secondary purification using heat. The separation chamber 151 is disposed adjacent to the pretreatment chamber 140 and contains a separation reagent. The separation chamber 151 receives the primarily purified liquid from the pretreatment chamber 140 and performs a thermal phase separation for the primarily purified liquid applied from the first heater 176. The separation chamber 151 discharges a secondarily purified liquid containing the nucleic acids to the reaction chamber 155 after the phase separation.

The separation reagent aggregates proteins when heat is applied. Thus, when the primarily purified liquid is supplied to the separation chamber 151 containing the separation reagent and then heat is applied to the separation chamber 15, the residue containing protein components may aggregate and float up while the secondarily purified liquid sinks down.

The separation chamber 151 discharges some of the secondarily purified liquid located below the aggregated residue to the reaction chamber 155.

The cleaning chamber 153 is disposed between the separation chamber 151 and the reaction chamber 155. The cleaning chamber 153 contains a cleaning liquid required for cleaning of the secondarily purified liquid and supplies the cleaning liquid to the reaction chamber 155 so that a tertiary purification can be performed. For example, the cleaning chamber 153 may include a first cleaning chamber 153a containing a first cleaning liquid and a second cleaning chamber 153b containing a second cleaning liquid. The first cleaning liquid may include ethanol and water. The second cleaning liquid may be ethanol.

The tertiary purification may be performed by a first cleaning step using the first cleaning liquid and a second cleaning step using the second the cleaning liquid. The reason why the cleaning is performed in a plurality of steps is to remove the remaining residue or reagents while leaving only the nucleic acids from the secondarily purified liquid.

The reason for using water together with ethanol as the first cleaning liquid is as follows. When the secondarily purified liquid is supplied to the reaction chamber 155, the nucleic acid contained in the secondarily purified liquid is adhered to magnetic particles contained in the reaction chamber 155. During the nucleic acid adhesion process, some residue may be adhered to the magnetic particles together with the nucleic acid, or some of the nucleic acids may be weakly adhered. Water has a property of separating material adhered to magnetic particles from the magnetic particles. Therefore, by using some water together with ethanol as the first the cleaning liquid, it is possible to separate the residue adhered to the magnetic particles or the nucleic acid adhered by a weak adhesion force.

The nucleic acid may be separated from the secondarily purified liquid by washing again with the second cleaning liquid after washing with the first cleaning liquid. The separated nucleic acid is adhered to the magnetic particles.

The elution chamber 157 is disposed between the reaction chamber 155 and the pretreatment chamber 140 and contains an eluent. The elution chamber 157 provides the reaction chamber 155 with the eluent. Water may be used as the eluent. The eluent separates the nucleic acid adhered to the magnetic particles.

The reaction chamber 155 is disposed between the cleaning chamber 153 and the elution chamber 157 to perform a tertiary purification and the nucleic acid separation or extraction. The reaction chamber 155 contains a binding reagent and magnetic particles.

First, the reaction chamber 155 performs the tertiary purification for the secondarily purified liquid supplied from the separation chamber 151. In other words, when the secondarily purified liquid is supplied from the separation chamber 151 to the reaction chamber 155, the magnetic particles selectively attracts the nucleic acids contained in the secondarily purified liquid, so that the nucleic acids adhere to the magnetic particles. The reaction chamber 155 discharges the secondarily purified liquid along with the binding reagent to the waste chamber 158 while leaving the magnetic particles to which the nucleic acids are adhered. The reaction chamber 155 receives the cleaning liquid from the cleaning chamber 153, cleans the magnetic particles to which the nucleic acids are adhered, and discharges the cleaning fluid to the waste chamber 158. Before discharging the solution in the reaction chamber 155 to the waste chamber 158, the second magnetic field applying unit 175 applies the magnetic field to the reaction chamber 155 to fix the magnetic particles to which the nucleic acids are adhered.

The reaction chamber 155 receives the eluent from the elution chamber 157, separates the nucleic acids from the magnetic particles, and discharges an eluate containing the nucleic acids to the nucleic acid amplification reagent chamber 159. Before the eluate containing the nucleic acids is discharged from the reaction chamber 155 to the nucleic acid amplification reagent chamber 159, the second magnetic field applying unit 175 applies the magnetic force to the reaction chamber 155 to fix the magnetic particles from which the nucleic acids have been separated.

The nucleic acid amplification reagent chamber 159 contains a nucleic acid amplification reagent. The nucleic acid amplification reagent chamber 159 receives the eluate containing the nucleic acids from the reaction chamber 155 to mixes with the nucleic acid amplification reagent and produce a nucleic acid amplification mixture. The nucleic acid amplification reagent chamber 159 discharges the nucleic acid amplification mixture to the nucleic acid amplification chamber 161. The nucleic acid amplification reagent may be prepared in the nucleic acid amplification reagent chamber 159 in a lyophilized form. A plurality of the nucleic acid amplification reagent chambers 159 may be provided in the cartridge. For example, the nucleic acid amplification reagent chamber 159 may include a first through fourth nucleic acid amplification reagent chambers 159a, 159b, 159c and 159d.

The nucleic acid amplification chamber 161 receives the nucleic acid amplification mixture from the nucleic acid amplification reagent chamber 159 and performs a nucleic acid amplification reaction using heat applied from the second heater 179. A plurality of the nucleic acid amplification chambers 161 may be provided in the cartridge. The plurality of nucleic acid amplification chambers 161 constitutes the nucleic acid amplification module 160. For example, the nucleic acid amplification chambers 161 may include a first through fourth nucleic acid amplification chambers 161a, 161b, 161c, and 161d.

The air valve module 133 shown in FIG. 6 selectively applies the air pressure required for the fluid movement between the plurality of chambers. The air valve module 133 includes twelve air valves for selectively applying the air pressure and an air flow path connecting the twelve valves and the pump 137. The twelve valves may be implemented based on solenoid valves.

The air valve module 133 may include a first through a twelfth air valves.

The first air valve 1 selectively applies the air pressure to the pretreatment chamber 140.

The second and the eighth air valves 2 and 8 selectively apply the air pressure to the separation chamber 151.

The third and the ninth air valves 3 and 9 selectively apply the air pressure to the first cleaning chamber 153a.

The fourth and the tenth air valves 4 and 10 selectively apply the air pressure to the second cleaning chamber 153b.

The fifth and the eleventh air valves 5 and 11 selectively apply the air pressure to the reaction chamber 155.

The sixth and the twelfth air valves 6 and 12 selectively apply the air pressure to the elution chamber 157.

The seventh air valve 7 selectively applies the air pressure to the nucleic acid amplification reagent chamber 159.

The liquid valve module 135 shown in FIGS. 7 and 8 opens or closes paths for the fluid movement between the plurality of chambers. The liquid valve module 135 includes twelve liquid valves for opening or closing the paths for the fluid movement between the plurality of chambers, and fluid flow paths for guiding the fluid movement between the plurality of chambers. The twelve valves may be implemented based on solenoid valves.

The liquid valve module 135 may include a thirteenth through a twenty-eighth liquid valves.

The thirteenth liquid valve 13 is installed at the pretreatment chamber 140.

The fourteenth liquid valve 14 is installed at the separation chamber 151.

The fifteenth liquid valve 15 is installed at the first cleaning chamber 153a.

The sixteenth liquid valve 16 is installed at the second cleaning chamber 153b.

The seventeenth liquid valve 17 is installed at the fluid flow path between the reaction chamber 155 and the waste chamber 158.

The eighteenth liquid valve 18 is installed at the reaction chamber 155.

The nineteenth liquid valve 19 is installed at the fluid flow path between the reaction chamber 155 and the nucleic acid amplification reagent chamber 159.

The twentieth liquid valve 20 is installed at the elution chamber 157.

The twenty-first to twenty-eighth valves 21-28 are installed at the plurality of nucleic acid amplification reagent chambers 159a, 159b, 159c, and 159d. There are four nucleic acid amplification reagent chambers 159, and each of four nucleic acid amplification reagent chambers 159 are provided with two liquid valves.

The fluid movement between the plurality of chambers during the nucleic acid extraction process is performed by cooperation of the air valve module 133 and the liquid valve module 135, which will be described in detail below in connection with the nucleic acid extraction method.

The structure of the valve 13 in the liquid valve module 135 and the operation thereof driven by the electromagnet 174a of the liquid valve actuator 174 will now be described with reference to FIGS. 9 and 10. FIGS. 9 and 10 illustrate a state that an electromagnet 174a of the liquid valve actuator 174a is installed in the valve 13 of the liquid valve module 135. The thirteenth valve 13 installed at the pretreatment chamber 140 is illustrated in FIGS. 9 and 10. FIG. 9 shows a state that the thirteenth valve 13 is closed, and FIG. 10 shows a state that the thirteenth valve 13 is open.

Since the liquid valves in the liquid valve module 135 have the same structure as each other, the following description of the liquid valve module 135 will be given in terms of the thirteenth valve 13 with reference to FIGS. 9 and 10.

The thirteenth valve 13 includes a valve structure 411 and a metal plate 421. The valve structure 411, which is made of elastic material, connects or disconnects flow paths 143a and 151a leading to the chambers 140 and 151, respectively. The metal plate 421 is installed beneath the valve structure 411 to move the valve structure 411 up and down according to the magnetic force applied through the liquid valve actuator 174 so as to connects or disconnects the flow paths. That is, the thirteenth valve 13 connects or disconnects the inlet flow path 143a connected to the pretreatment chamber 140 in fluid communications to or from the outlet flow path 151a connected to the separation chamber 151 in fluid communications. The thirteenth valve 13 connects or disconnects the inlet flow path 143a to or from the outlet flow path 151a of the separation chamber 151 by opening or closing the inlet flow path 143a.

The valve structure 411 includes a tubular valve column 413, a valve body 417, and a diaphragm 415. The valve body 417 is spaced apart from an inner wall of the valve column 413 and is positioned at the center of the valve column 413 in the radial direction, and has a valve dome 419 for opening and closing the inlet flow path 143a in its upper portion. The diaphragm 415 connects the valve body 417 to the inner wall of the valve column 413 in such a manner that allows the valve body 417 to move up and down elastically in the valve column 413 so as to open and close the inlet flow path 143a and control the flow of the fluid between the two chambers 140 and 151.

At this time, the valve column 413 supports the valve structure 411 and enables the thirteenth valve 13 to be mounted on the cartridge 110. The valve column 413 supports the valve body 417 via the diaphragm 415 connected to its inner wall.

The valve body 417 is installed inside the valve column 413 in a shape of being suspended by the diaphragm 415. The metal plate 421 is attached to the bottom of the valve body 417. The valve dome 419 disposed in the top of the valve body 417 is normally closed. That is, when no external force such as the magnetic force is not exerted on the valve 13, the valve dome 419 protrudes to the top of the valve column 413 to always close the inlet flow path 143a.

Now, the operation of the thirteenth valve 13 is described in detail as follows.

The inlet flow path 143a and the outlet flow path 151a through which the fluid can flow are installed on the thirteenth valve 13 capable of interrupting the fluid flow, and an electromagnet 174a of the liquid valve actuator 174 capable of changing the state of the thirteenth valve 13 is installed beneath the thirteenth valve 13.

When the fluid (i.e. the primarily purified liquid) is to be transferred from the pretreatment chamber 140 to the separation chamber 151, the fluid flows through the inlet flow path 143a and the outlet flow path 151a. The thirteenth valve 13 capable of interrupting the fluid flow is located between the inlet flow path 143a and the outlet flow path 151a. The thirteenth valve 13 is comprised of the valve structure 411 made of the elastic material and the metal plate 421. The valve structure 411 is positioned in a connecting hollow 423 where the inlet flow path 143a and the outlet flow path 151a can be connected and is in contact with an end of the inlet flow path 143a. Since the valve structure 411 is made of the elastic material, the valve structure 411 may be locally compressed at the contact position with the inlet flow path 143a to block the inlet flow path 143a. At this time, an end of the outlet flow path 151a is exposed to the connecting hollow 423 and thus is separated from the inlet flow path 143a in fluid communications. Thus, the flow path through which the fluid can move from the pretreatment chamber 140 to the separation chamber 151 is blocked by an operation of the thirteenth valve 13 in this case. The thirteenth valve 13 is a normally closed valve because the valve structure 411 made of the elastic material remains the contact with the end of the inlet flow path 143a until an external force is exerted to pull down the valve structure 411.

In order to open the thirteenth valve 13 and allow the flow of the fluid through the flow paths 143a and 151a, the valve structure 411 which is in contact with the inlet flow path 143a should be pulled down. Pulling down of the valve structure 411 takes advantage of a magnetic property of the metal plate 421 installed beneath the valve structure 411.

The electromagnet 174a of the liquid valve actuator 174 is disposed below the metal plate 421 being spaced apart from the metal plate 421 by a certain distance. When power is applied to the liquid valve actuator 174, a strong magnetic field is generated near the top of the electromagnet 174a and pulls the metal plate 421 attached beneath the valve body 417 toward the top of the electromagnet 174a. Thus, in response to the application of power to the electromagnet 174a of the liquid valve actuator 174, the metal plate 421 moves down and sticks to the top of the electromagnet 174a as shown in FIG. 10.

After the metal plate 421 is stuck to the electromagnet 174a, the valve body 417 coupled to the metal plate 421 moves downward with the metal plate 421 to open the inlet flow path 143a. The opened inlet flow path 143a is connected to the outlet flow path 151a in fluid communications through the connecting hollow 423, thereby changing state of the thirteenth valve 13 into the open state that allows the flow of the fluid.

When the metal plate 421 is stuck to the electromagnet 174a, the diaphragm 415 of which outer end is coupled to the inner wall of the valve column 413 is stretched downwards to allow the valve body 417 to move downwards and make the inlet flow path 143a to be opened. That is, the valve dome 419 having an upwardly convex shape and having blocked the inlet flow path 143a before the power is applied to the electromagnet 174a moves downwards to open the inlet flow path 143a.

The thirteenth valve 13 maintains the open state allowing the flow of the fluid as long as the power is applied to the electromagnet 174a. If the applied power is cut off, however, the external force pulling on the metal plate 421 is removed and the valve dome 419 returns to its original position with respect to the valve body 417 by an elastic force resulting from the diaphragm 415. In other words, the valve body 417 moves up to block the inlet flow path 143a.

Preferably, the diaphragm 415 is formed to have a thickness suitable for the valve body 417 to be elastically changed according to turning on or off of the electromagnet 174a. The thicker the diaphragm 415 is, the more force is required to move the valve body 417. Accordingly, it is necessary to expect a range of an impact that the valve body 417 may receive while moving and maintaining the cartridge 110 containing the fluid and to design the diaphragm 415 such that the valve body 417 is open only when a force greater than an expected range of the impact is applied to the valve body 417. Therefore, the diaphragm 415 is made thicker in the case the flow of the fluid is to be blocked by a strong elastic force while the diaphragm 415 can be made thinner in the case that the flow of the fluid can be blocked by a weak elastic force.

Meanwhile, as the thickness of the diaphragm 415 increases, a switching from the closed state to the open state needs a larger force, which requires a more powerful electromagnet 174a. Therefore, it is preferable to manufacture the diaphragm 415 to have an appropriate thickness depending on an environment in which the valve is used. In addition, since the maximum pressure to maintain the closed state depends on an elasticity of the valve structure 411, it is also necessary to choose a material of the valve structure 411 suitable for the pressure range to be used. For example, the diaphragm 415 may be manufactured to have a thickness of 100 to 1,000 μm.

The metal plate 421 attached beneath the valve body 417 to drive the valve body 417 by the electromagnet 174a can be inserted when the valve structure 411 is injection-molded with elastic material. The metal plate 421 may be made of material, such as iron, that can easily stick to the electromagnet 174a. As the metal plate 421 is wider and thicker, the metal plate 421 can easily stick to the electromagnet 174a. In addition, soft iron can be used for the material of the metal plate 421 to minimize a magnetic hysteresis remaining after the electromagnet 174a is turned off.

A nucleic acid analysis method using the nucleic acid extracting cartridge 110 according to an exemplary embodiment will now be described with reference to FIGS. 12-19.

Figure 12:
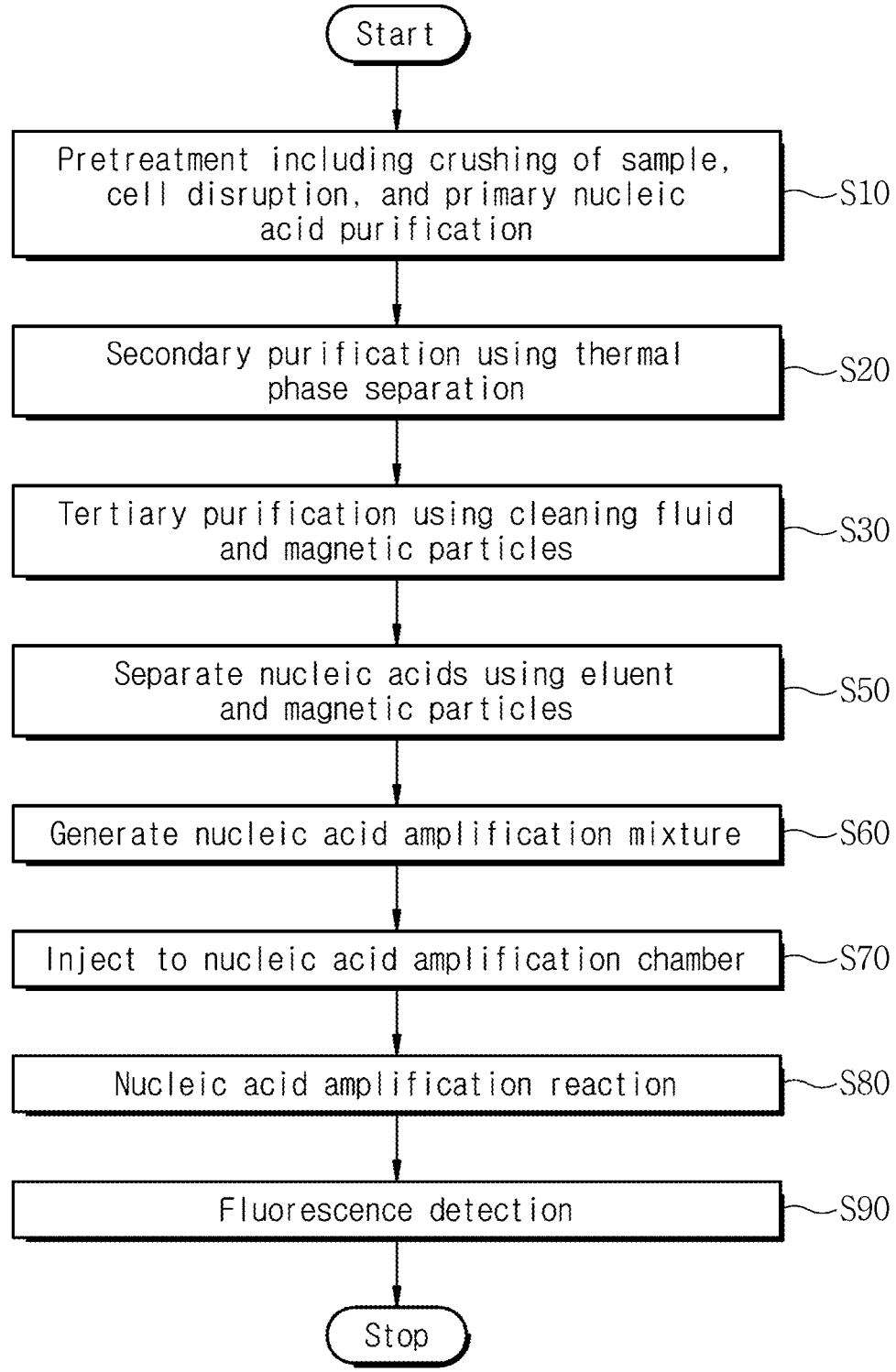
FIG. 12 is a flowchart illustrating a nucleic acid analysis method using a nucleic acid extracting cartridge according to an exemplary embodiment of the present disclosure.

FIG. 12 is a flowchart illustrating the nucleic acid analysis method using the nucleic acid extracting cartridge according to an exemplary embodiment of the present disclosure.

The nucleic acid analysis method according to the present embodiment includes a pretreatment operation S10 including the crushing of the sample, the cell disruption, and the primary nucleic acid purification, a secondary purification operation S20 using thermal phase separation, a tertiary purification operation S30 using the cleaning liquid and the magnetic particles, a nucleic acid separation operation S50 using the eluent and the magnetic particles, a nucleic acid amplification mixture generation operation S60, a nucleic acid amplification chamber injection operation S70, a nucleic acid amplification reaction operation S80, and a fluorescence detection operation S90.

Pretreatment Including Primary Purification

In the operation S10, when the sample is introduced into the pretreatment chamber, the pretreatment process including the crushing of the sample, the cell disruption, and the primary nucleic acid purification is collectively performed in the pretreatment chamber, and the primarily purified liquid is discharged to the separation chamber.

Figure 13:
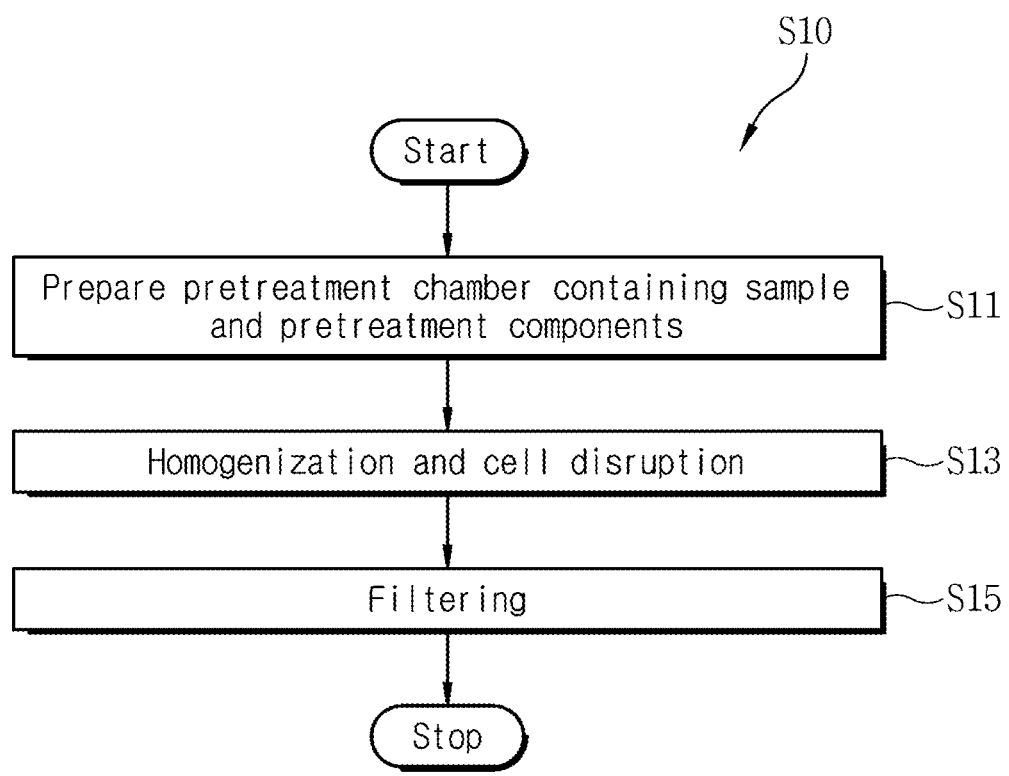
FIG. 13 is a detailed flowchart illustrating a pretreatment operation shown in FIG. 12.

The pretreatment operation S10 will now be described in more detail with reference to FIGS. 13-16. FIG. 13 is a detailed flowchart illustrating the pretreatment operation shown in FIG. 12, and FIGS. 14 to 16 illustrate unit operations of the pretreatment operation shown in FIG. 13 in detail.

Figure 14:
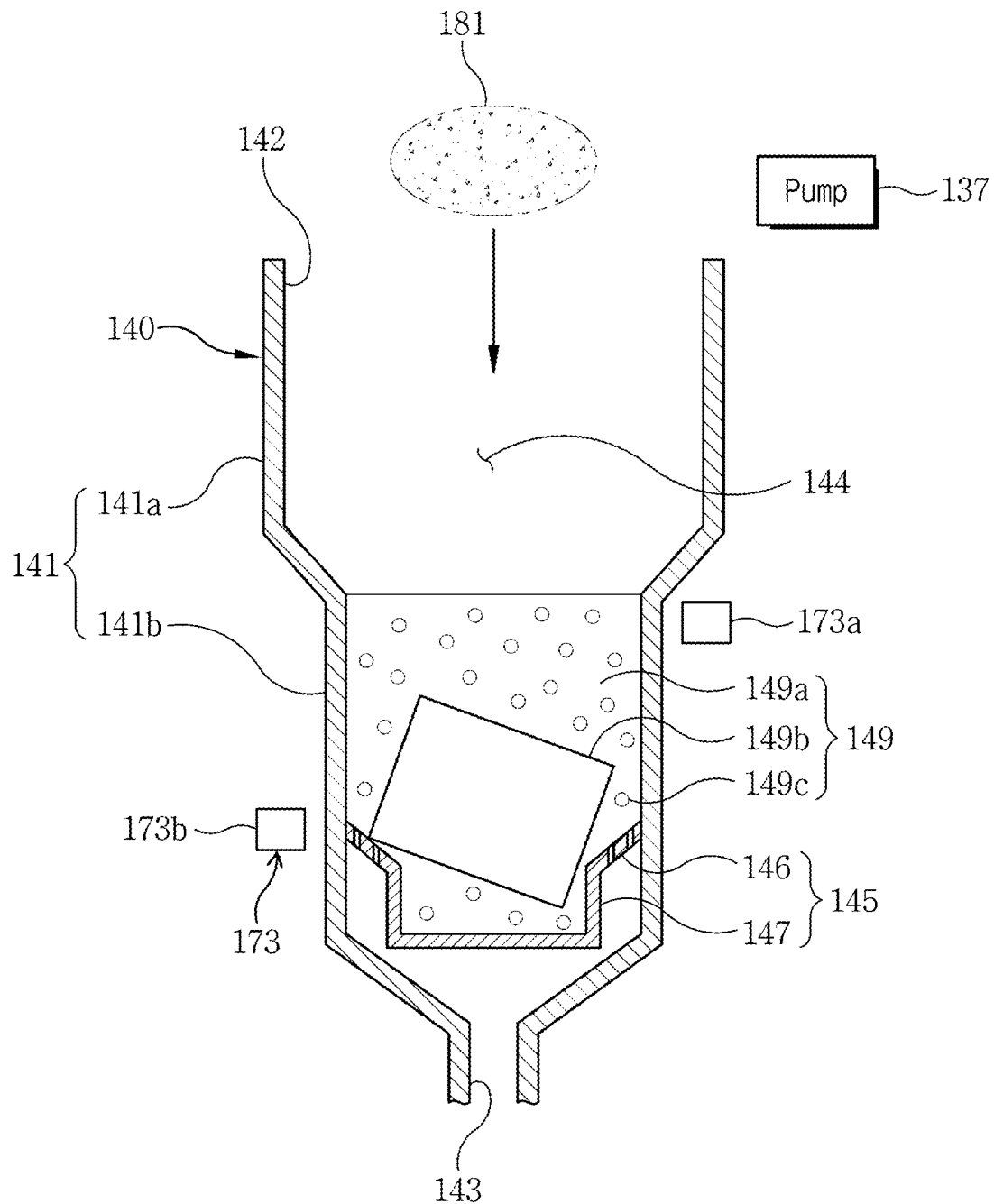
FIGS. 14 to 16 illustrate unit operations of the pretreatment operation shown in FIG. 13 in detail.

First, as shown in FIG. 14, the pretreatment chamber 140 containing the sample 181 and the pretreatment components 149 is prepared in operation S11. For example, the sample 181 may be introduced into the pretreatment components 149 after the pretreatment components 149 are loaded in the pretreatment chamber 140. Alternatively, the pretreatment components 149 may be loaded first and then the sample 181 may be introduced into the pretreatment chamber 140. The sample 181 and the pretreatment components 149 may be introduced simultaneously into the pretreatment chamber 140 as well.

Figure 15:
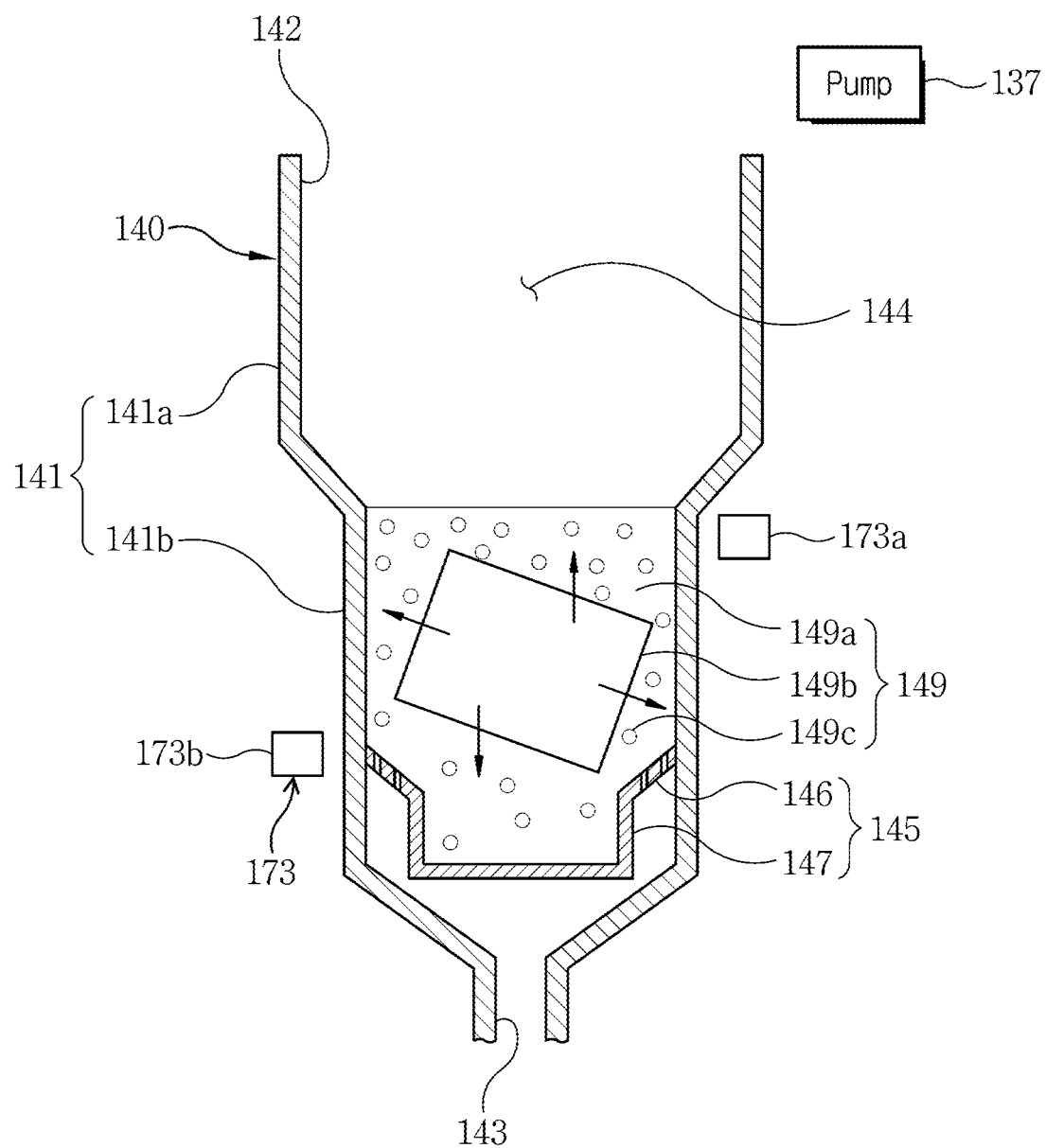

Next, in operation S13, the homogenization of the sample and the cell disruption are performed as shown in FIG. 15. That is, the first magnetic field applying segment 173a and the second magnetic field applying segment 173b intermittently apply the magnetic field to the pretreatment chamber 140 to move the magnet block 149b, so that the sample is crushed and homogenized. At this time, the switching of the magnetic fields generated by the first magnetic field applying segment 173a and the second magnetic field applying segment 173b results in the movement of the magnet block 149b in the pretreatment fluid. The movement of the magnet block 149b brings about random motions of the cell disruption particles 149c, which may destroy the cells contained in the sample and allow the nucleic acids to flow out of the cells.

Meanwhile, the pretreatment chamber may be heated to facilitate the homogenization of the sample and the cell disruption.

Figure 16:
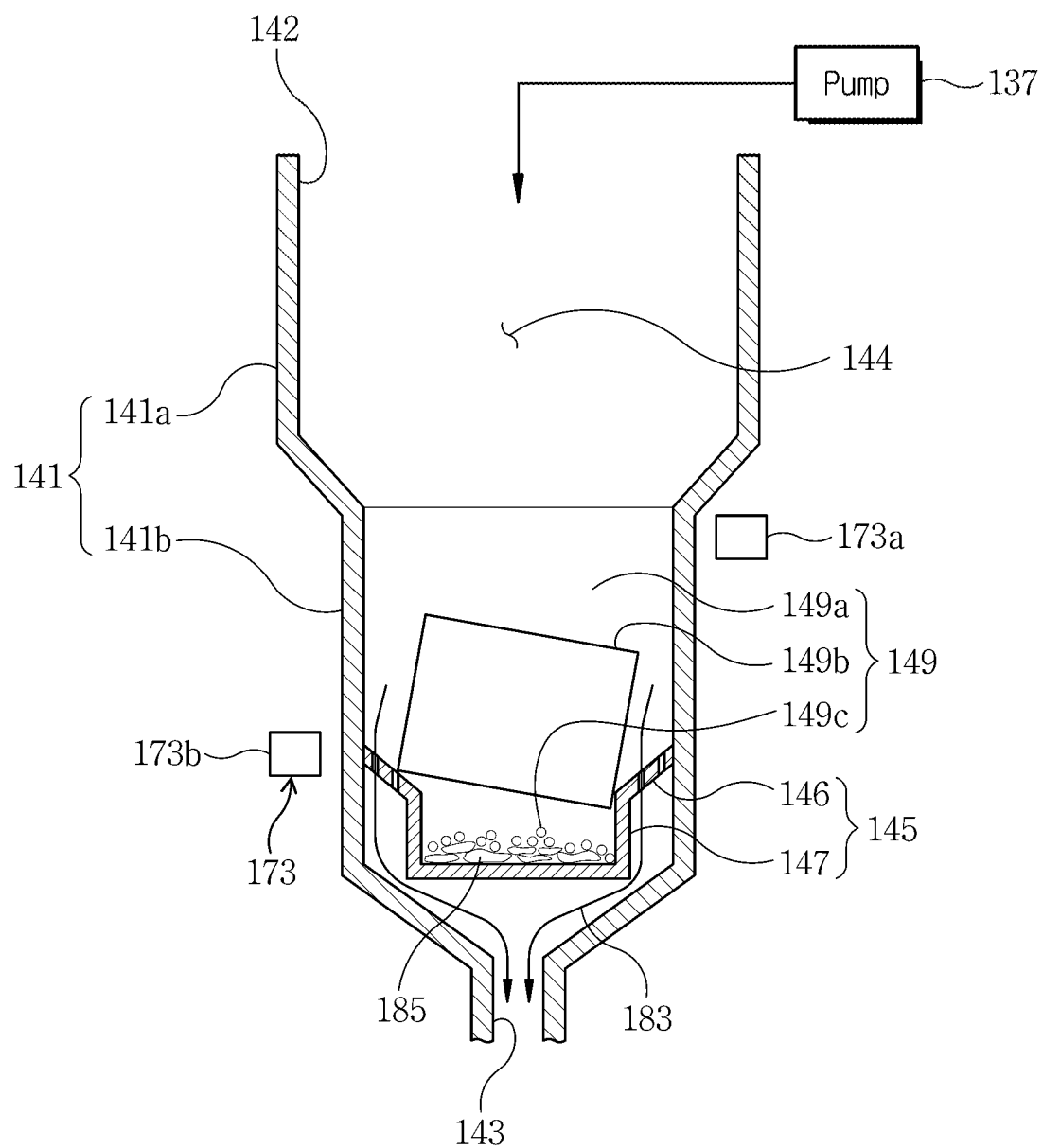

Afterwards, in operation S15, the contents of the pretreatment chamber is filtered and the primarily purified liquid 183 having passed the cup filter 145 is discharged to the separation chamber as shown in FIG. 16. During the primary purification operation, the pressure generated by the pump 137 may be applied to the pretreatment chamber so that the nucleic acids flown out of the cells in the cell disruption is compelled to pass the cup filter 145 disposed in the lower part of the pretreatment chamber 140.

The residue having not passed through the filter portion 146 of the cup filter 145 moves along the tapered surface of the filter portion 146 to be precipitated on the cup portion 147. A reference numeral 185 denotes the precipitate formed of residue having moved to the cup portion 147.

The operations of the air valve module 133 and the liquid valve module 135 for moving the primarily purified liquid 183 from the pretreatment chamber 140 to the separation chamber are described with reference to FIGS. 6 and 7.

First, the first valve 1, the eighth valve 8, and the thirteenth valve 13 are opened sequentially. Next, the pump 137 is operated to apply the pressure to the pretreatment chamber 140 to transfer the primarily purified liquid to the separation chamber 151. When the movement of the primarily purified liquid is completed, the first valve 1, the eighth valve 8, and the thirteenth valve 13 are closed sequentially. Subsequently, the pump 137 is turned off and ventilated.

Secondary Purification

Figure 17:
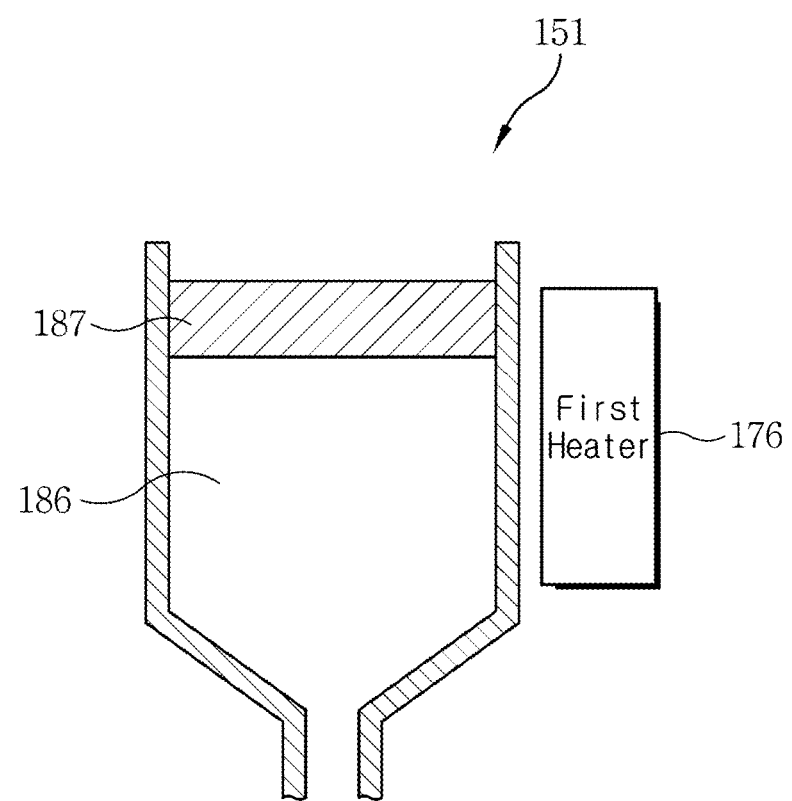
FIG. 17 illustrates a separation chamber suitable for use in a secondary purification operation shown in FIG. 12.

When the primarily purified liquid is introduced to the separation chamber 151, the secondary purification is performed in operation S20 in the separation chamber 151 shown in FIG. 17 using thermal phase separation, and the secondarily purified liquid 186 is discharged to the reaction chamber. FIG. 17 illustrates the separation chamber suitable for use in the secondary purification operation shown in FIG. 12.

At this time, the first heater 176 may apply heat of 50 to 80° C. to the separation chamber 151 for 3 to 30 minutes. The heat applied to the separation chamber 151 causes the residue contained in the primarily purified liquid to aggregate and float up in the form of a floating matter 187 while the secondarily purified liquid 186 which are relatively cleaner is located below the floater 187.

The operations of the air valve module 133 and the liquid valve module 135 for moving the secondarily purified liquid 183 from the separation chamber 151 to the reaction chamber is described with reference to FIGS. 6-8.

First, the second valve 2, the eighteenth valve 18, the eleventh valve 11, and the fourteenth valve 14 are opened sequentially. Next, the pump 137 is operated to apply the pressure to the separation chamber 151 to transfer the secondarily purified liquid to the reaction chamber 155. Subsequently, the second valve 2, the eighteenth valve 18, and the eleventh valve 11 are closed sequentially. The second valve 2, the fourteenth valve 14, and the seventeenth valve 17 are opened, so that the secondarily purified liquid remaining in the separation chamber 151 and the fluid flow path connecting and the separation chamber 151 and the reaction chamber 155 is discharged to the waste chamber 158. Subsequently, the pump 137 is turned off and ventilated. Also, the second valve 2, the fourteenth valve 14, and the seventeenth valve 17 are closed.

Tertiary Purification

When the secondarily purified liquid is introduced to the reaction chamber 155, the tertiary purification using the cleaning liquid and the magnetic particles is performed in operation S30 in the reaction chamber 155. Though the washing according to the tertiary purification can be performed multiple times, it is assumed that the washing is performed twice in the present embodiment.

Figure 18:
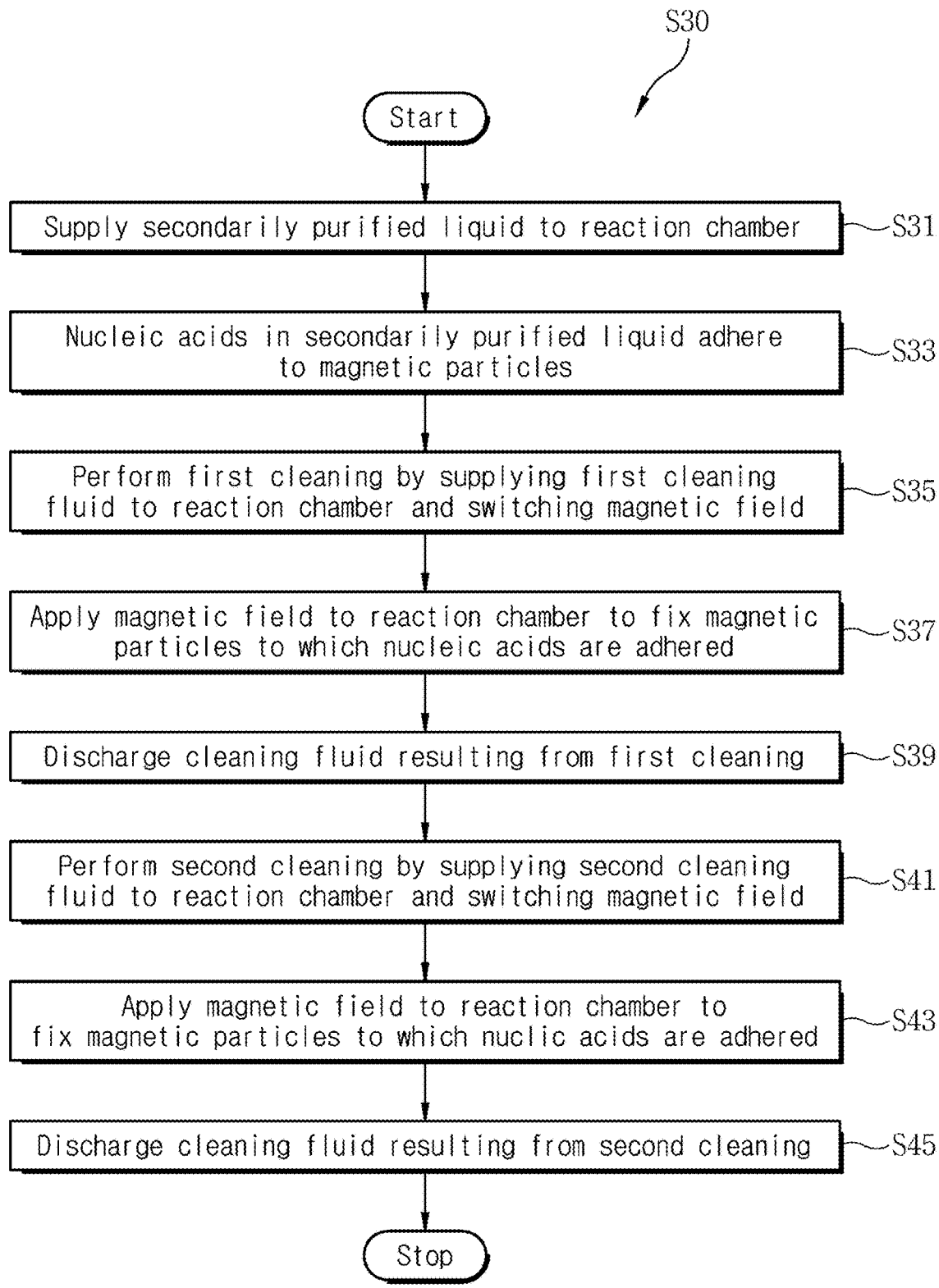
FIG. 18 is a detailed flowchart illustrating a tertiary purification operation shown in FIG. 12.

The tertiary purification operation S30 shown in FIG. 12 will now be described with reference to FIG. 18. FIG. 18 is a detailed flowchart illustrating the tertiary purification operation.

In operation S31, the secondarily purified liquid is supplied from the separation chamber 151 to the reaction chamber 155.

In operation S33, the magnetic particles contained in the reaction chamber 155 selectively attract the nucleic acids contained in the secondarily purified liquid, and the nucleic acids adhere to the magnetic particles. A switching magnetic field may be applied to the reaction chamber 155 to facilitate the attraction of the magnetic particles and the adhesion of the nucleic acids. After the nucleic acid adhesion process, a magnetic field is applied to the reaction chamber 155 to fix the magnetic particles to which the nucleic acids are adhered. The remaining solution except the magnetic particles to which the nucleic acids are adhered may be discharged from the reaction chamber 155 to the waste chamber 158. The application of the magnetic field to the reaction chamber 155 is accomplished by the second magnetic field applying unit 175.

In operations S35 through S45, the reaction chamber 155 is provided with the cleaning liquid from the cleaning chamber 151 to clean the magnetic particles to which the nucleic acids are adhered, and then discharges the waste solution except the magnetic particles to the waste chamber 158. In the present embodiment, the operations S35 through S45 are performed twice as mentioned above.

In operation S35, the first cleaning liquid is added to the reaction chamber 155, and then the magnetic field is switched to perform the first cleaning. In operation S37, the magnetic field is applied to the reaction chamber 155 to fix the magnetic particles with the nucleic acids which have undergone the first cleaning. In operation S39, the cleaning fluid resulting from the first cleaning is discharged from the reaction chamber 155 to the waste chamber 158 to complete the first cleaning.

In operation S41, the second cleaning liquid is added to the reaction chamber 155, and then the magnetic field is switched to perform the second cleaning. In operation S43, the magnetic field is applied to the reaction chamber 155 to fix the magnetic particles with the nucleic acids which have undergone the second cleaning. In operation S45, the cleaning fluid resulting from the second cleaning is discharged from the reaction chamber 155 to the waste chamber 158 to complete the second cleaning.

The operations of the air valve module 133 and the liquid valve module 135 for allowing the nucleic acids to adhere to the magnetic particles in the reaction chamber 155 are described with reference to FIGS. 6-8.

First, the magnetic field generated by the second magnetic field applying unit 175 is switched and applied to the reaction chamber 155 so that the nucleic acids contained in the secondarily purified liquid adhere to the magnetic particles. The magnetic particles wander in the mixture of the secondarily purified liquid and binding reagent because of the switching magnetic field, and the nucleic acids adhere to the magnetic particles.

After the nucleic acids are adhered to the magnetic particles, a steady magnetic field may be applied to the reaction chamber 155 to fix the magnetic particles.

Next, the fifth valve 5, the eighteenth valve 18, and the seventeenth valve 17 are opened and then the pump 137 is operated to discharge the remaining solution in the reaction chamber 155 to the waste chamber 158.

Then, the seventeenth valve 17 is closed and the pump 137 is turned off.

Finally, the fifth valve 5 and the eighteenth valve 18 are sequentially closed to complete the operation S35.

The operations of the air valve module 133 and the liquid valve module 135 during the first cleaning operations of S37 through S39 is described with reference to FIGS. 6-8.

First, the magnetic particles to which the nucleic acids are adhered are fixed by the magnetic field applied by the second magnetic field applying unit 175.

The third valve 3, the eighteenth valve 18, the eleventh valve 11, and the fifteenth valve 15 are opened sequentially. Next, the pump 137 is driven to supply the first cleaning liquid in the first cleaning chamber 153a to the reaction chamber 155.

Next, the fifteenth valve 15, the eleventh valve 11, the eighteenth valve 18, and the third valve 3 are closed sequentially. Subsequently, the pump 137 is turned off and ventilated.

Afterwards, the magnetic field generated by the second magnetic field applying unit 175 is switched and applied to the reaction chamber 155 to clean the magnetic particles to which the nucleic acids are adhered. The magnetic particles wander in the first cleaning liquid because of the switching magnetic field, and the magnetic particles to which the nucleic acids undergo the first cleaning in the first cleaning liquid.

After the first cleaning of the magnetic particles to which the nucleic acids are adhered is completed, a steady magnetic field is applied to the reaction chamber 155 to fix the magnetic particles.

Next, the fifth valve 5, the eighteenth valve 18, and the seventeenth valve 17 are opened and then the pump 137 is operated to discharge the first cleaning liquid remaining in the reaction chamber 155 to the waste chamber 158.

Then, the seventeenth valve 17 is closed and the pump 137 is turned off.

Finally, the fifth valve 5 and the eighteenth valve 18 are sequentially closed to complete the first cleaning.

The operations of the air valve module 133 and the liquid valve module 135 during the second cleaning operations of S41 through S45 is described with reference to FIGS. 6-8. The second cleaning is performed in the same manner as the first cleaning except that the second cleaning liquid contained in the second cleaning chamber 153b is supplied to the reaction chamber 155 instead of the first cleaning liquid contained in the first cleaning chamber 153a.

First, after the first cleaning operation, the magnetic particles to which the nucleic acids are adhered are fixed by the magnetic field applied by the second magnetic field applying unit 175.

The fourth valve 4, the eighteenth valve 18, the eleventh valve 11, and the sixteenth valve 16 are opened sequentially. Next, the pump 137 is driven to supply the second cleaning liquid in the second cleaning chamber 153b to the reaction chamber 155.

Next, the sixteenth valve 16, the eleventh valve 11, the eighteenth valve 18, and the fourth valve 4 are closed sequentially. Subsequently, the pump 137 is turned off and ventilated.

Afterwards, the magnetic field generated by the second magnetic field applying unit 175 is switched and applied to the reaction chamber 155 to clean the magnetic particles to which the nucleic acids are adhered. The magnetic particles wander in the second cleaning liquid because of the switching magnetic field, and the magnetic particles to which the nucleic acids undergo the second cleaning in the second cleaning liquid.

After the second cleaning of the magnetic particles to which the nucleic acids are adhered is completed, a steady magnetic field is applied to the reaction chamber 155 to fix the magnetic particles.

Next, the fifth valve 5, the eighteenth valve 18, and the seventeenth valve 17 are opened and then the pump 137 is operated to discharge the second cleaning liquid remaining in the reaction chamber 155 to the waste chamber 158.

Then, the seventeenth valve 17 is closed and the pump 137 is turned off.

Finally, the fifth valve 5 and the eighteenth valve 18 are sequentially closed to complete the second cleaning.

Nucleic Acid Separation

Referring back to FIG. 12, the separation of the nucleic acids using the eluent and the magnetic particles is performed in the reaction chamber 155 in operation S50. The eluate containing the separated nucleic acids is discharged from the reaction chamber 155 to the nucleic acid amplification reagent chamber 159.

Figure 19:
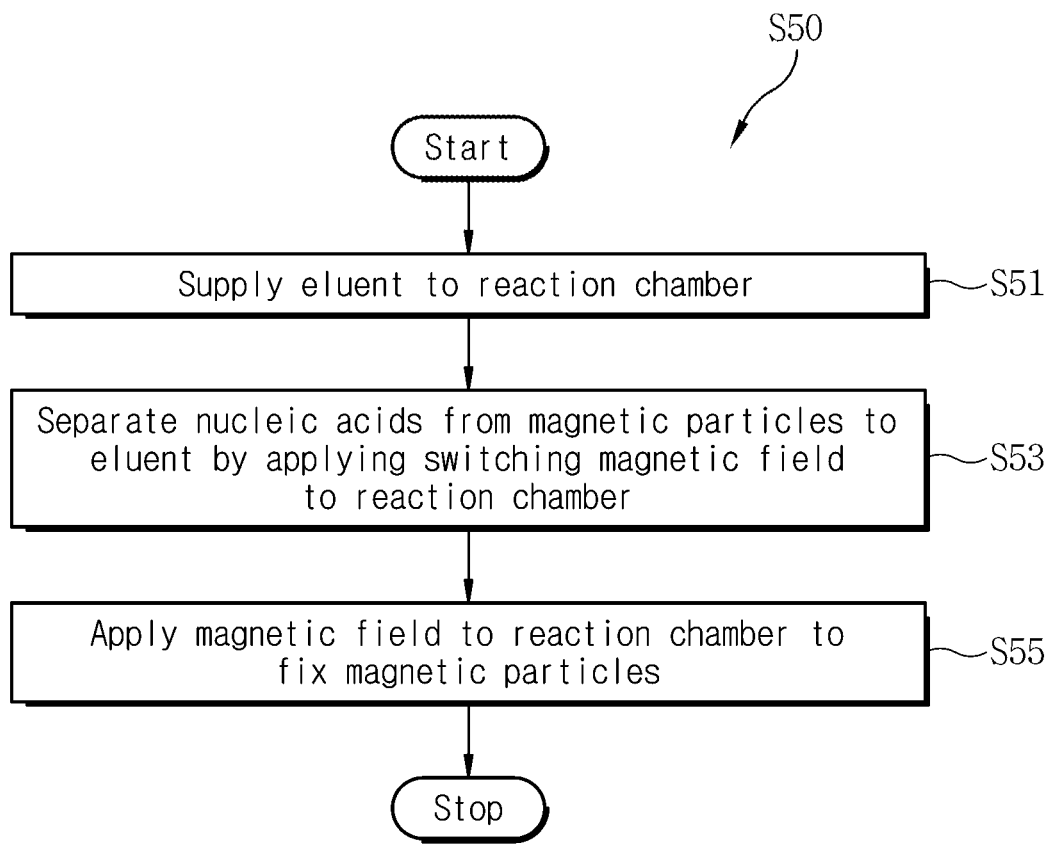
FIG. 19 is a detailed flowchart illustrating a nucleic acid separation operation shown in FIG. 12.

The nucleic acid separation operation S50 will now be described in detail with reference to FIG. 19. FIG. 19 is a detailed flowchart illustrating the nucleic acid separation operation shown in FIG. 12.

First, the eluent is supplied from the elution chamber 157 to the reaction chamber 155 in operation S51.

Subsequently, in operation S53, the magnetic field generated by the second magnetic field applying unit 175 is switched and applied to the reaction chamber 155, so that the nucleic acids are separated from the magnetic particles. The magnetic particles wander in the eluent because of the switching magnetic field, and the nucleic acids can be separated from the magnetic particles.

After the nucleic acids are separated from the magnetic particles, the magnetic field is applied to the reaction chamber 155 to fix the magnetic particles in operation S55. At this time, the nucleic acids separated from the magnetic particles are dispersed in the eluate.

The operations of the air valve module 133 and the liquid valve module 135 for the nucleic acid separation operation of S50 is described with reference to FIGS. 6-8.

First, after the second cleaning operation, the magnetic particles to which the nucleic acids are adhered are fixed by the magnetic field applied by the second magnetic field applying unit 175.

Then, the sixth valve 6, the eighteenth valve 18, the eleventh valve 11, and the twentieth valve 20 are opened sequentially.

Next, the pump 137 is driven to supply the eluent in the elution chamber 157 to the reaction chamber 55.

Next, the twentieth valve 20, the eleventh valve 11, the eighteenth valve 18, and the sixth valve 6 are closed sequentially. Subsequently, the pump 137 is turned off and ventilated.

Afterwards, the magnetic field generated by the second magnetic field applying unit 175 is switched and applied to the reaction chamber 155, so that the nucleic acids are separated from the magnetic particles into the eluent.

After the separation of the nucleic acids is completed, a magnetic field is applied to the reaction chamber 155 to fix the magnetic particles.

Formation of Nucleic Acid Amplification Mixture

Referring back to FIG. 12, the eluate containing the nucleic acids is transferred from the reaction chamber 155 to the nucleic acid amplification reagent chamber 159 in operation S60, so that the eluate is mixed with the nucleic acid amplification reagent in the nucleic acid amplification reagent chamber 159 to form the nucleic acid amplification mixture.

The operations of the air valve module 133 and the liquid valve module 135 for generating the nucleic acid amplification mixture in the operation S60 is described with reference to FIGS. 6-8.

First, after the separation of the nucleic acids, the magnetic particles are fixed in the reaction chamber 155 by the magnetic field applied by the second magnetic field applying unit 175.

Next, the fifth valve 5, the eighteenth valve 18, and the nineteenth valve 19 are opened sequentially. Subsequently, the twenty-fifth through twenty-eighth valves 25-28 are opened.

Then, the twenty-first through twenty-fourth valves 21-24 are sequentially turned on and off, so that the eluate containing the nucleic acids is provided to the first through fourth nucleic acid amplification reagent chambers 159a-159d and the nucleic acid amplification mixture is generated.

That is, the eluate containing the nucleic acids is provided to the first nucleic acid amplification reagent chambers 159a by opening the twenty-fourth valve 24 and operating the pump 137. When the first nucleic acid amplification reagent chamber 159a is filled with the eluate containing the nucleic acids, the pump 137 is turned off and the twenty-fourth valve 24 and the twenty-eighth valve 28 are closed. The filling of the eluate containing the nucleic acids in the first nucleic acid amplification reagent chamber 159a may be detected by using an infrared sensor.

Next, the eluate containing the nucleic acids is provided to the second nucleic acid amplification reagent chambers 159b by opening the twenty-third valve 23 and operating the pump 137. When the second nucleic acid amplification reagent chamber 159b is filled with the eluate containing the nucleic acids, the pump 137 is turned off and the twenty-third valve 23 and the twenty-seventh valve 27 are closed.

Next, the eluate containing the nucleic acids is provided to the third nucleic acid amplification reagent chambers 159c by opening the twenty-second valve 22 and operating the pump 137. When the third nucleic acid amplification reagent chamber 159c is filled with the eluate containing the nucleic acids, the pump 137 is turned off and the twenty-second valve 22 and the twenty-sixth valve 26 are closed.

Next, the eluate containing the nucleic acids is provided to the fourth nucleic acid amplification reagent chambers 159d by opening the twenty-first valve 21 and operating the pump 137. When the fourth nucleic acid amplification reagent chamber 159d is filled with the eluate containing the nucleic acids, the pump 137 is turned off and the twenty-first valve 21 and the twenty-fifth valve 25 are closed.

The nucleic acids supplied to the first through fourth nucleic acid amplification reagent chambers 159a, 159b, 159c, and 159d are mixed with the nucleic acid amplification reagent to form the nucleic acid amplification mixture.

Injection to Nucleic Acid Amplification Chamber

Referring back to FIG. 12, in operation S70, the nucleic acid amplification chamber 161 receives the nucleic acid amplification mixture from the nucleic acid amplification reagent chamber 159.

The operations of the air valve module 133 and the liquid valve module 135 for injecting the nucleic acid amplification mixture to the nucleic acid amplification chamber 161 in the operation S70 is described with reference to FIGS. 6-8.

First, the seventh valve 7 is opened, and then the pump 137 is turned on.

Next, the twenty-fourth valve 24 and the twenty-eighth valve 28 are opened to supply the nucleic acid amplification mixture in the first nucleic acid amplification reagent chamber 159a to the first nucleic acid amplification chamber 161a until the nucleic acid amplification mixture fills the first nucleic acid amplification chamber 161a. The filling the nucleic acid amplification mixture in the first nucleic acid amplification chamber 161a may be detected by using an infrared sensor.

Similarly, the nucleic acid amplification mixture in the second through fourth nucleic acid amplification reagent chambers 159b, 159c and 159d are supplied to and fill the second through fourth nucleic acid amplification chambers 161b, 161c and 161d, respectively.

That is, the nucleic acid amplification mixture in the second nucleic acid amplification reagent chamber 159b is supplied to and fills the second nucleic acid amplification chamber 161b by opening the twenty-third valve 23 and the twenty-seventh valve 27.

Next, the nucleic acid amplification mixture in the third nucleic acid amplification reagent chamber 159c is supplied to and fills the third nucleic acid amplification chamber 161c by opening the twenty-second valve 22 and the twenty-sixth valve 26.

Next, the nucleic acid amplification mixture in the fourth nucleic acid amplification reagent chamber 159d is supplied to and fills the fourth nucleic acid amplification chamber 161d by opening the twenty-first valve 21 and the twenty-fifth valve 25.

By turning off the pump 137, the filling of the first through fourth nucleic acid amplification chambers 161a, 161b, 161c, and 161d in the nucleic acid amplification module 160 with the nucleic acid amplification mixture is completed.

Nucleic Acid Amplification Reaction

In operation S80, the nucleic acid amplification reaction is performed using heat applied to the nucleic acid amplification chamber 161. The heat is applied by the second heater 179 to the nucleic acid amplification chamber 161.

Fluorescence Detection

In operation S90, the fluorescence detection unit 197 detects the nucleic acids by optically detecting the fluorescence of a plurality of wavelength bands emitted from the nucleic acid amplification chamber 161 after the nucleic acid amplification.

The fluorescence detection unit 197 and the fluorescence detection method using the detection unit according to the present embodiment will be now described with reference to FIGS. 20-34. In the present embodiment, the nucleic acid amplification module 160 on the cartridge includes a plurality of nucleic acid amplification chambers 161. Since the cartridge 110 is mounted on the stage 192 as shown in FIG. 3, the plurality of nucleic acid amplification chambers 161 are arranged in a vertical direction as shown in FIG. 5. However, an example in which the plurality of the nucleic acid amplification chambers 161 are arranged in a horizontal direction is described for convenience of description.

Figure 20:
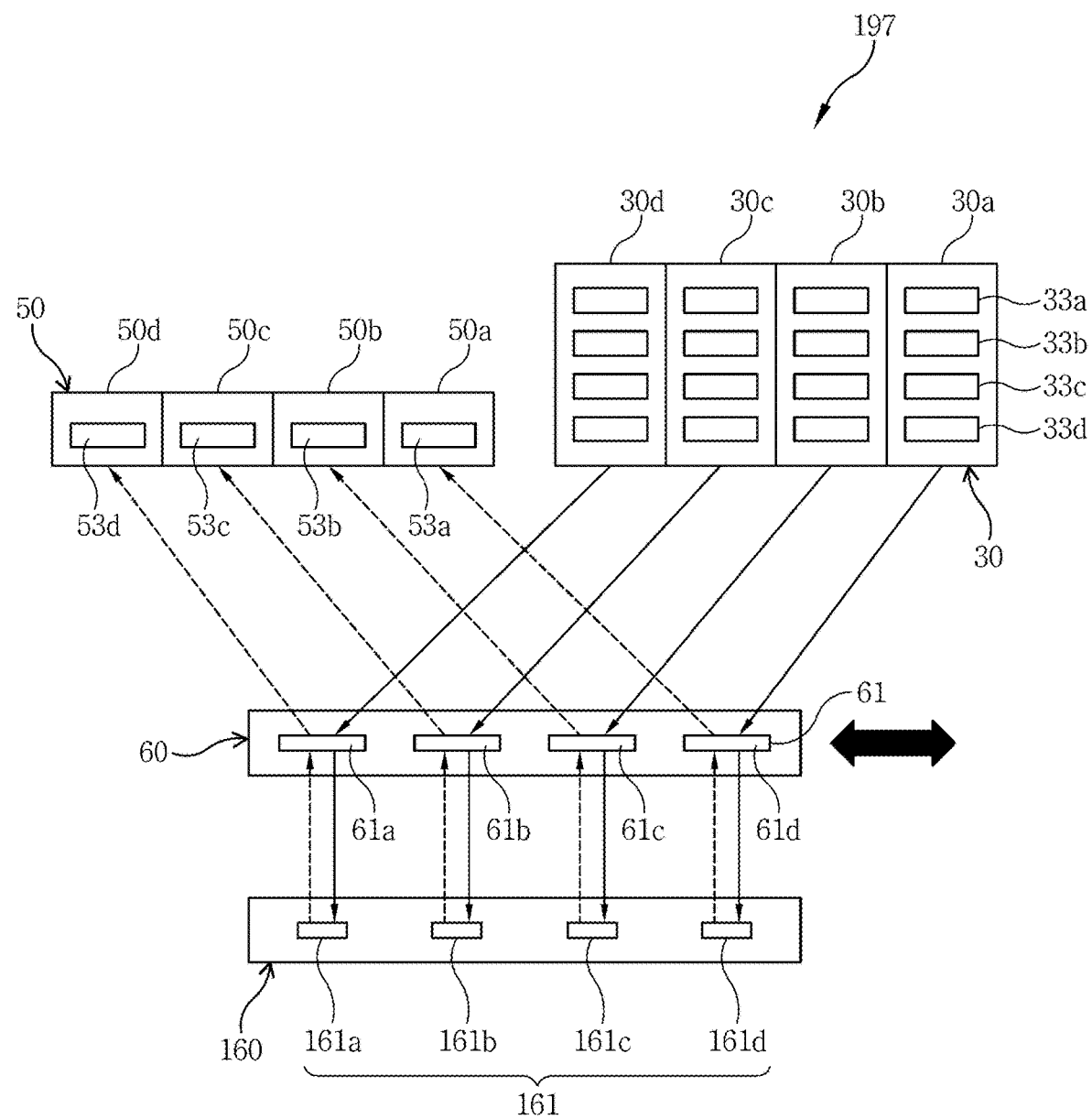
FIG. 20 is a block diagram of a fluorescence detection unit shown in FIG. 4.

FIG. 20 is a block diagram of the fluorescence detection unit 197 shown in FIG. 4.

Referring to FIG. 20, the fluorescence detection unit 197 according to the present embodiment optically detects the fluorescence signal corresponding to the fluorescence of a plurality of wavelengths emitted from the plurality of nucleic acid amplification chambers 161a-161d in which the nucleic acid amplification reaction is simultaneously performed.

The fluorescence detection unit 197 according to this embodiment includes the plurality of light emitters 30, the plurality of light receivers 50, and the movable filter 60, and optically detects the fluorescence signal by moving the movable filter 60 with respect to the nucleic acid amplification module 160, the plurality of light emitters 30, and the plurality of light receivers 50 which are fixed. Each of the plurality of light emitters 30 emits light of a plurality of color series to be directed to the plurality of nucleic acid amplification chambers 161a-161d, respectively. Each of the plurality of light receivers 50 are arranged to form a pair with respective one of the plurality of light emitters 30, and includes an optical sensor 53a-53d suitable for receiving the fluorescence emitted from the plurality of nucleic acid amplification chambers 161a-161d to convert into a respective fluorescence signal. The movable filter 60 is placed between an assembly of the plurality of light emitters 30 and the plurality of light receivers 50 and the plurality of nucleic acid amplification chambers 161a-161d. The movable filter 60 is installed to be movable in a direction in which the plurality of nucleic acid amplification chambers 161a-161d are arranged and can be controlled to move to face the plurality of nucleic acid amplification chambers 161a-161d. The movable filter 60 includes a plurality of filter modules 61a-61d which filter the light of a specific wavelength from the light of the plurality of color series incident from the plurality of light emitters 30 to direct filtered lights to the plurality of nucleic acid amplification chambers 161a-161d, and filter the fluorescence of a specific wavelength out of the fluorescence emitted from the plurality of nucleic acid amplification chambers 161a-161d to direct filtered fluorescence to the plurality of light receivers 50.

The plurality of light emitters 30 and the plurality of light receivers 50 may be positioned over the plurality of filter modules 61a-61d of the movable filter 60, and nucleic acid amplification module 160 may be positioned below the plurality of filter modules 61a-61d of the movable filter 60. That is, the plurality of light emitters 30 and the plurality of light receivers 50 may be located on the opposite side of the nucleic acid amplification module 160 with respect to the path of the plurality of filter modules 61a-61d.

The nucleic acid amplification module 160 includes the plurality of nucleic acid amplification chambers 161a-161d.

The plurality of nucleic acid amplification chambers 161a-161d include a first through a fourth nucleic acid amplification chambers 161a, 161b, 161c, and 161d arranged in a row. A plurality of nucleic acid amplification reactions may occur simultaneously by probes or primers in the nucleic acid amplification chambers 161a-161d. When a plurality of nucleic acid amplification reactions occur, the fluorescence of different wavelength bands may be emitted according to the nucleic acid amplification reactions. The movable filter 60 allows to detect the fluorescence of different wavelength bands in the present embodiment.

Each of the plurality of light emitters 30 include a plurality of light sources 33a-33d that output light of the plurality of color series. The plurality of light emitters 30 include a first through a fourth light emitters 30a-30d. The plurality of light sources 33a-33d may be arranged in a direction perpendicular to a direction in which the plurality of nucleic acid amplification chambers 161a-161d are arranged.

The plurality of light sources 33a-33d may include a first light source 33a outputting the light of a first color series, a second light source 33b positioned below the first light source 33a and outputting the light of a second color series, a third light source 33c positioned below the second light source 33b and outputting the light of a third color series, and a fourth light source 33d positioned below the third light source 33c and outputting the light of a fourth color series. The lights of the first through fourth color series may be red, yellow, green, and blue, respectively.

The plurality of light receivers 50 include the optical sensors 53a-53d, respectively, and may be disposed adjacent to the plurality of light emitters 30. That is, the plurality of light receivers 50 may include a first light receiver 50a corresponding to the first light emitter 30a, a second light receiver 50b corresponding to the second light emitter 30b, a third light receiver 50c corresponding to the third light emitter 30c, and a fourth light receiver 50d corresponding to the fourth light emitter 30d. The first through fourth light receivers 50a-50d may be arranged in the horizontal direction correspondingly to the first through fourth light emitters 30a-30d.

The movable filter 60 filters the light of the first through fourth color series to direct the filtered light to the nucleic acid amplification chambers 161a-161d, and filters the fluorescence of a specific wavelength among the fluorescence emitted from the nucleic acid amplification chambers 161a-161d to direct the filtered the fluorescence to the light receiver 50. The movable filter 60 includes a first filter module 61a processing the light of the first color series, a second filter module 61b processing the light of the second color series, the third filter module 61c processing the light of the third color series, and a fourth filter module 61d processing the light of the fourth color series. The first through fourth filter modules 61a-61d are arranged in the horizontal direction, i.e. along the direction in which the first through fourth nucleic acid amplification chambers 161a-161d are arranged.

The first through fourth filter modules 61a-61d move to face the first through fourth nucleic acid amplification chambers 161a-161d sequentially, while directing the light of the first through fourth wavelength bands filtered from the light received from the light emitter 30 to the first through fourth nucleic acid amplification chambers 161a-161d and directing the fluorescence of the (4-1)-th through (4-4)-th wavelength bands filtered from the fluorescence emitted from the nucleic acid amplification chambers 161a-161d to the first through fourth light receivers 50a-50d.

For example, in case that the movable filter 60 moved such that the first filter module 61a is positioned to face the fourth light emitter 30d, the second filter module 61b is positioned to face the third light emitter 30c, and the third filter module 61c is positioned to face the second light emitter 30b, and the fourth filter module 61d is positioned to face the first light emitter 30a, the fluorescence detection is performed as follows.

The fourth light emitter 30d outputs the light of the first color series generated by the first light source 33a to the first filter module 61a. The third light emitter 30c outputs the light of the second color series generated by the second light source 33b to the second filter module 61b. The second light emitter 30b outputs the light of the third color series generated by the third light source 33c to the third filter module 61c. The first light emitter 30a outputs the light of the fourth color series generated by the fourth light source 33d to the fourth filter module 61d.

The first through fourth filter modules 61a-61d direct light of the first through fourth wavelength bands filtered from the light of the first through fourth color series to the fourth through the first nucleic acid amplification chambers 161d, 161c, 161b, and 161a, respectively.

Then, the first through fourth filter modules 61a-61d filters the fluorescence of the (4-4)-th through (4-1)-th wavelength bands from the fluorescence emitted from the nucleic acid amplification chambers 161a-161d to direct the filtered fluorescence to the fourth through the first light receivers 50d-50a, respectively.

The configuration of the fluorescence detection unit 197 according to the present embodiment will now be described in more detail with reference to FIGS. 21-27.

Figure 21:
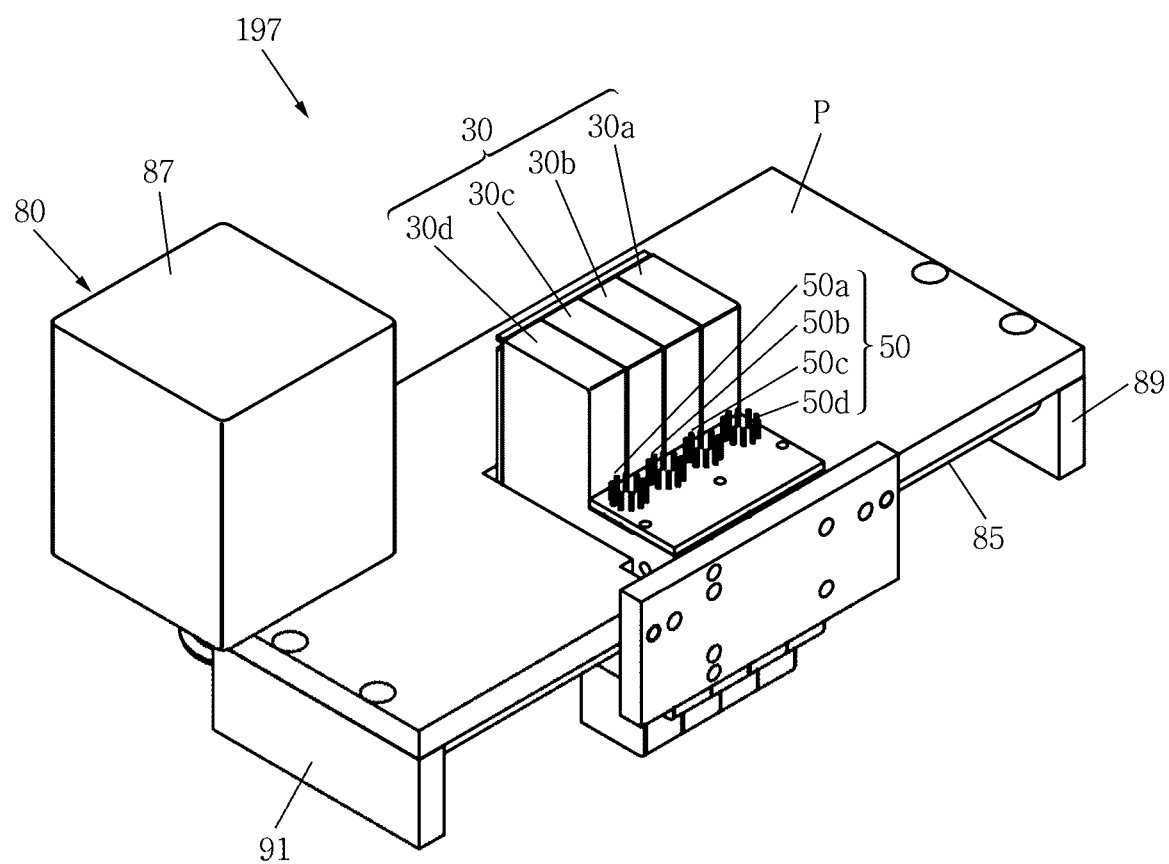
FIG. 21 is a perspective view of the fluorescence detection unit of FIG. 20.
Figure 22:
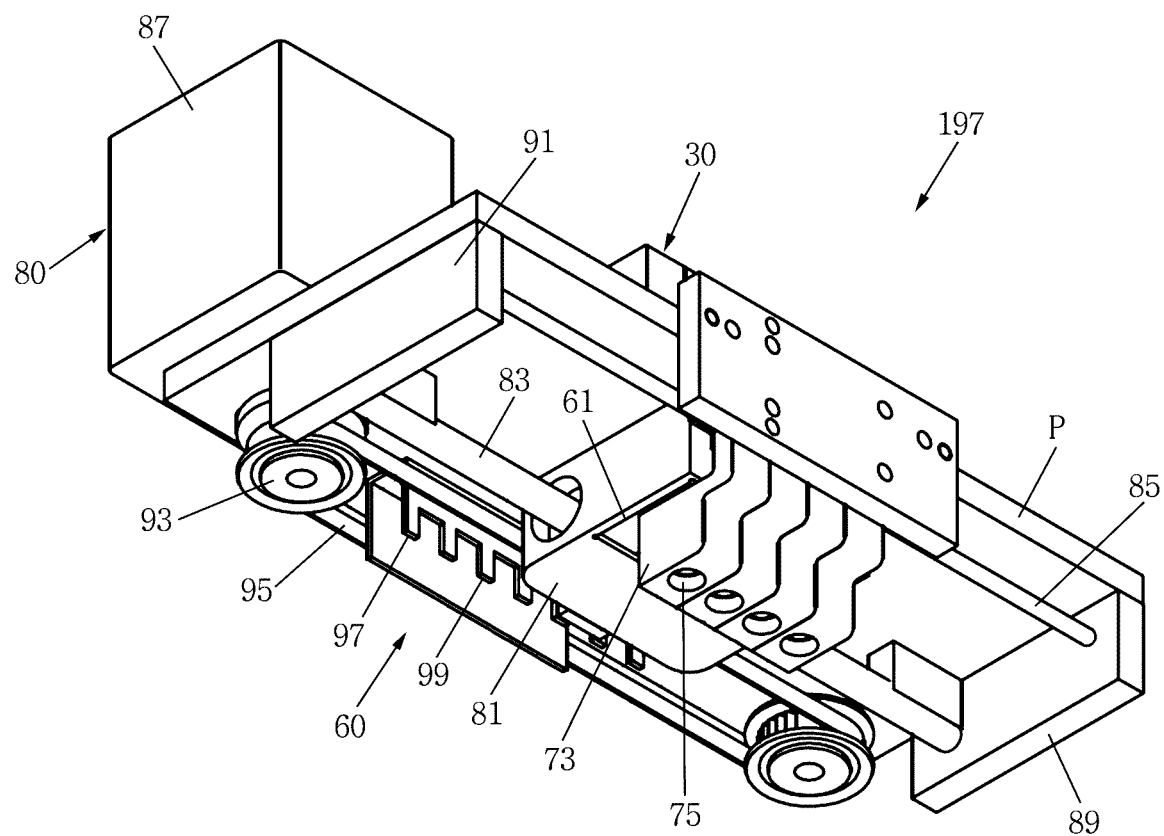
FIG. 22 is a bottom perspective view of the fluorescence detection unit of FIG. 21.
Figure 23:
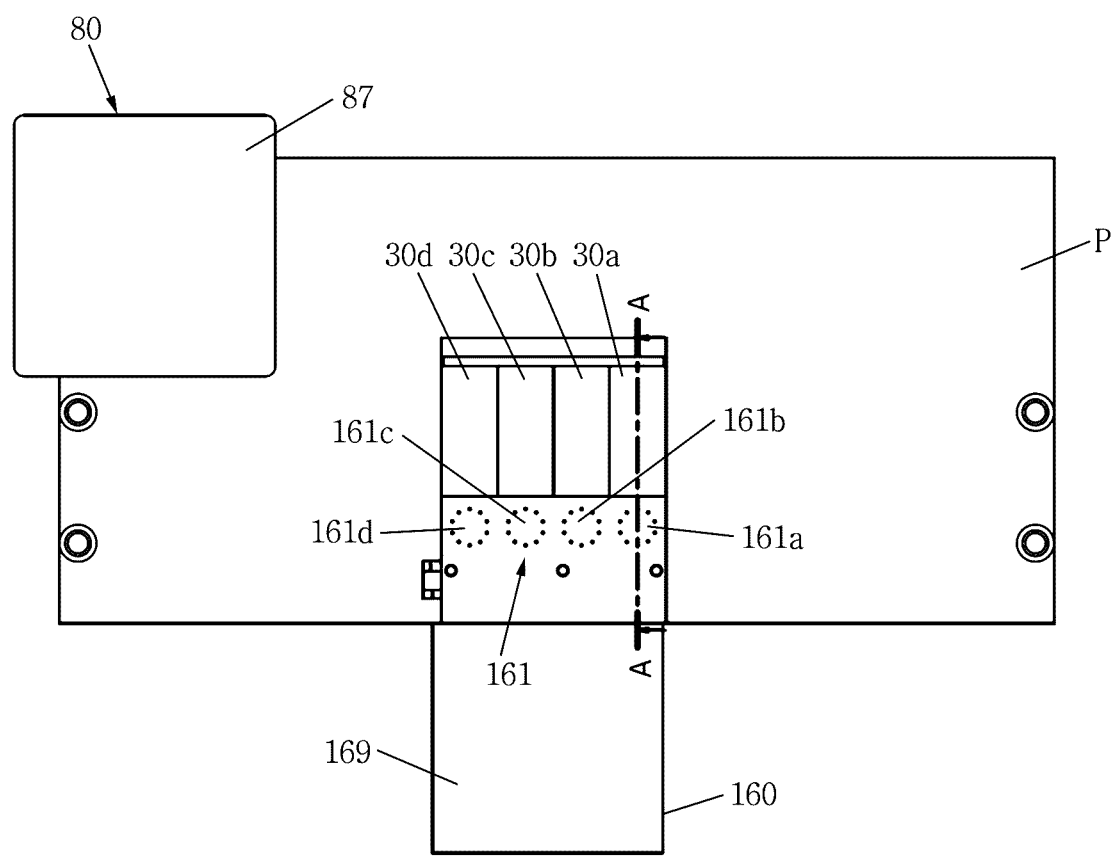
FIG. 23 is a planar view of the fluorescence detection unit of FIG. 21.
Figure 24:
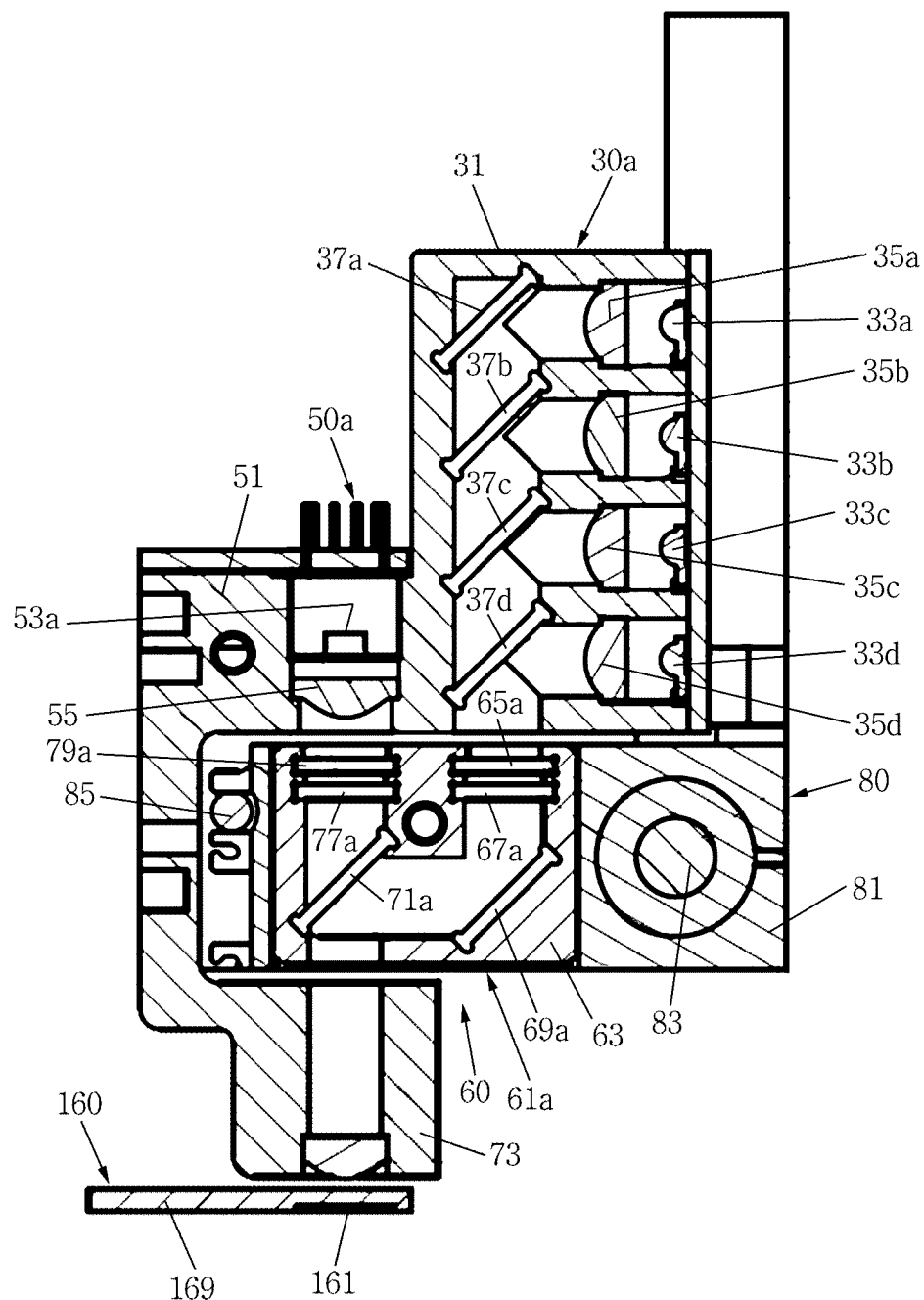
FIG. 24 is a cross-sectional view taken along a line A-A of FIG. 23.
Figure 25:
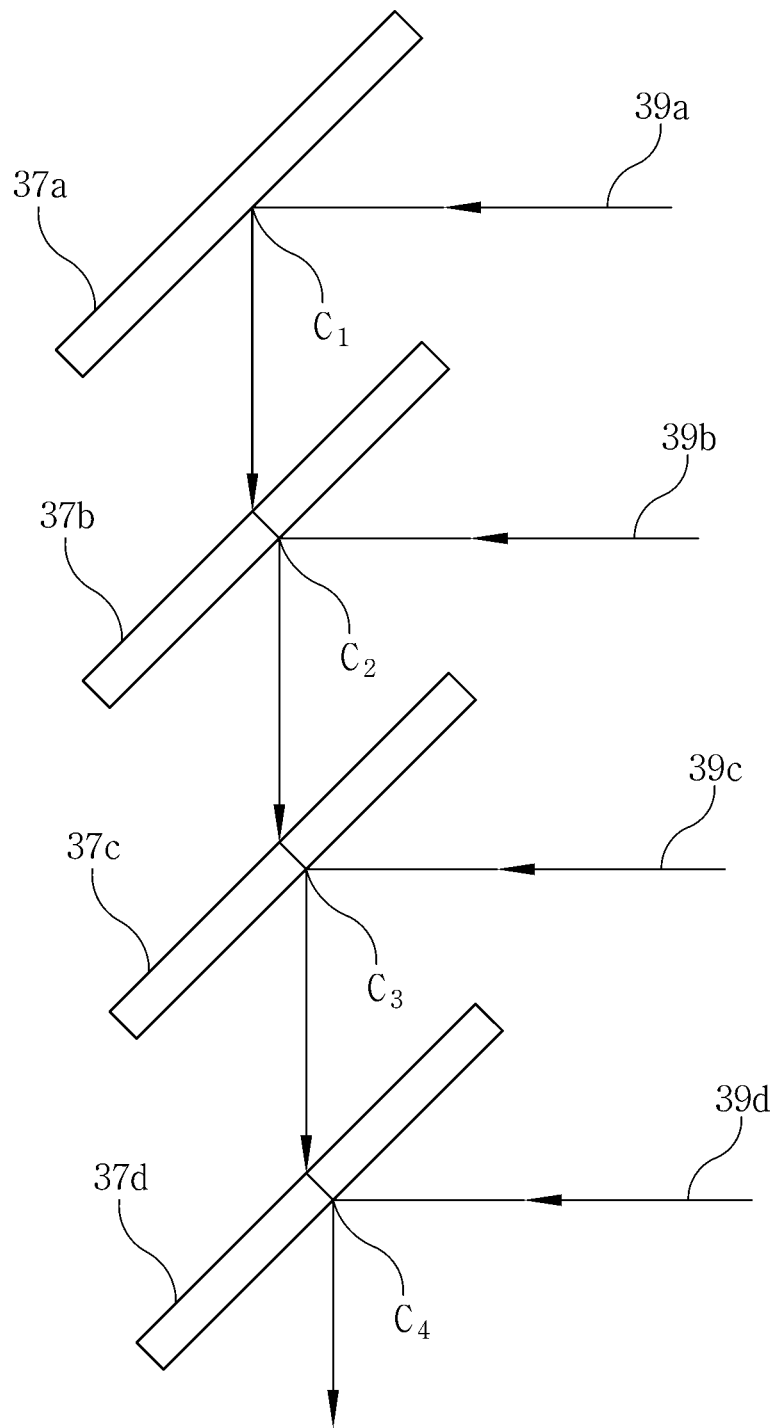
FIG. 25 illustrates an example of optical paths of a light emitted by a light emitter shown in FIG. 23.

FIG. 21 is a perspective view of the fluorescence detection unit 197 of FIG. 20. FIG. 22 is a bottom perspective view of the fluorescence detection unit 197. FIG. 23 is a planar view of the fluorescence detection unit 197. FIG. 24 is a cross-sectional view taken along a line A-A of FIG. 23. FIG. 25 illustrates an example of optical paths of a light emitted by a light emitter shown in FIG. 23.

The fluorescence detection unit 197 according to the present embodiment includes the plurality of light emitters 30, the plurality of light receivers 50, and the movable filter 60, and may further include a frame P.

The frame P is a base plate on which the plurality of light emitters 30, the plurality of light receivers 50, and the movable filter 60 are installed as shown in FIGS. 21-23. The nucleic acid amplification module 161 may be disposed under the frame P, for example. The plurality of light emitters 30 and the plurality of light receivers 50 are fixedly mounted on the frame P. The plurality of filter modules 61 of the movable filter 60 may be installed under the frame P to be movable between the assembly of the plurality of light emitters 30 and the plurality of light receivers 50 and the nucleic acid amplification module 160.

The nucleic acid amplification module 160 includes a module body 169 and the plurality of nucleic acid amplification chambers 161a-161d arranged in a line on the module body 169.

The plurality of light emitters 30 include the first through fourth light emitters 30a-30d. Since the first through fourth light emitters 30a-30d have the same structure as each other, the plurality of light emitters 30 will be described in a viewpoint of the first light emitter 30a with reference to FIG. 24.

The first light emitter 30a includes the plurality of light sources 33a-33d, a plurality of mirrors 37a-37d, a plurality of focusing lenses 35a-35d, and a light emitter body 31. The plurality of light sources 33a-33d include the first through fourth light sources 33a-33d. The plurality of mirrors 37a-37d include the first through fourth mirrors 37a-37d. The plurality of focusing lenses 35a-35d include the first through fourth focusing lenses 35a-35d provided to correspond to the first through fourth light sources 33a-33d, respectively.

The plurality of light sources 33a-33d, the plurality of mirrors 37a-37d, and the plurality of focusing lenses 35a-35d are installed in the light emitter body 31, and light passages are formed through the light emitter body 31 to allow the light of the first through fourth colors to output from the first light emitter 30a. The light passages include a first through fourth individual passages elongated horizontally to be parallel to directions of the light of the first through fourth colors output by the first through fourth light sources 33a-33d, respectively, and disposed vertically and a main passage elongated vertically to connect the first through fourth individual passages.

The plurality of light sources 33a-33d include the first through fourth light sources 33a-33d which output the light of the first through fourth color series. The first light source 33a is installed at one end of the first individual passage to emit the light of the first color series. The second light source 33b is positioned below the first light source 33a and installed at one end of the second individual passage to emit the light of the second color series. The third light source 33c is positioned below the second light source 33b and installed at one end of the third individual passage to emit the light of the third color series. The fourth light source 33d is positioned below the third light source 33c and installed at one end of the fourth individual passage to emit the light of the fourth color series.

The plurality of focusing lenses 35a-35d include the first through fourth focusing lenses 35a-35d positioned in front of the first through fourth light sources 33a-33d, respectively, as shown in FIG. 24. The first through fourth focusing lenses 35a-35d focus the light of the first through fourth colors output by the first through fourth light sources 33a-33d, so that the focused lights are directed to corresponding mirrors 37a-37d, respectively. The first through fourth focusing lenses 35a-35d are installed in the first to fourth individual passages, respectively.

Each of the plurality of mirrors 37a-37d reflects the light output by a corresponding light source while passing the lights output by the other light sources as shown in FIG. 24. The mirror 37a disposed at the top of the plurality of mirrors 37a-37d may be a total reflection mirror, and the other mirrors 37b-37d may be dichroic mirrors. These multiple of mirrors 37a-37d include the first through fourth mirrors 37a-37d and are installed in the main passage.

The first mirror 37a is installed in front of the first light source 33a, i.e. at a position where the light of the first color series is output from the first light source 33a, and reflects the light of the first color series output by the first light source 33a downward along the main passage.

The second mirror 37b is located below the first mirror 37a and installed in front of the second light source 33b, i.e. at a position where the light of the second color series is output from the second light source 33b. The second mirror 37b passes the light of the first color series reflected by the first mirror 37a while reflecting the light of the second color series output by the second light source 33b downward along the main passage.

The third mirror 37c is located below the second mirror 37b and installed in front of the third light source 33c, i.e. at a position where the light of the third color series is output from the third light source 33c. The third mirror 37c passes the lights of the first and second color series reflected by the first and second mirrors 37a and 37b while reflecting the light of the third color series output by the third light source 33c downward along the main passage.

The fourth mirror 37d is located below the third mirror 37c and installed in front of the fourth light source 33d, i.e. at a position where the light of the fourth color series is output from the fourth light source 33d. The fourth mirror 37d passes the lights of the first through third color series reflected by the first through third second mirrors 37a-37c while reflecting the light of the fourth color series output by the fourth light source 33d downward along the main passage.

The light of the first through fourth color series reflected by or passed the first through fourth mirrors 37a-37d enters the first through fourth filter modules 61a-61d, respectively. The first through fourth mirrors 37a-37d may be installed at 45 degrees with respect to a horizontal plane to reflect the lights incident in the horizontal direction downwards.

A total reflection mirror may be used as the first mirror 37a and dichroic mirrors may be used as the second through fourth mirrors 37b-37d as mentioned above.

Meanwhile, the first through fourth mirrors 37a-37d have a first through fourth central spots C1-C4 reflecting or passing the lights as shown in FIG. 25. A center of light passing through each of the second through fourth mirrors 37b-37d is deviated from that before the light enters the mirror because of a refraction of light arising from the thickness of the dichroic mirror. As a result, in case that the second through fourth mirrors 37b, 37c, and 37d are disposed vertical at the same position in the horizontal direction, the positions of the first through fourth central spots C1 to C4 may become different from each other.

Therefore, it is desirable to dispose the first through fourth mirrors 37a-37d, in consideration of the refractive indices and the thicknesses of the second through fourth mirrors 37b-37d, such that the light of the first through fourth colors are reflected by or passes the first through fourth mirrors 37a-37d at the central spots C1-C4 of the first through fourth mirrors 37a-37d. That is, the first through fourth mirrors 37a-37d are disposed such that the central spots C1-C4 of the first through fourth mirrors 37a-37d are aligned.

For example, the first through fourth mirrors 37a-37d may be disposed such that the third central spot C3, the second central spot C2, and the first central spot C1 are located farther sequentially in an ascending order from the fourth central spot C4 in the horizontal direction. The light of the first color series output by the first light source 33a is reflected by the first mirror 37a and then passes through the second through fourth mirrors 37b-37d and then are incident on the first through fourth filter modules 61a-61d. Thus, the second through fourth mirrors 37b-37d are disposed as follows based on the refractive indices and the thicknesses of the second through fourth mirrors 37b-37d. In this example, the thicknesses of the second through fourth mirrors 37b-37d are assumed to be 1 millimeter (mm).

The light of the fourth color series 39d which is reflected by the fourth mirror 37d closest to the first through fourth filter modules 61a-61d does not pass through any inclined mirror, and thus the arrangement of the mirrors are described based on the fourth central spot C4.

Since the light of the third color series 39c is reflected by the third mirror 37c and passes through the fourth mirror 37d, the third central spot C3 is displaced by about 0.34 mm to the left from the fourth central spot C4.

Since the light of the second color series 39b is reflected by the second mirror 37b and passes through the third and fourth mirrors 37c and 37d, the second central spot C2 is displaced by about 0.68 mm to the left from the fourth central spot C4.

Since the light of the first color series 39a is totally reflected by the first mirror 37a and passes through the second through fourth mirrors 37b-37d, the first central spot C1 is displaced by about 1.01 mm to the left from the fourth central spot C4.

The plurality of light receivers 50 includes a first to fourth light receivers 50a-50d correspondingly to the plurality of light emitters 30. Since the first through fourth light receivers 50a-50d have the same structure as each other, the plurality of light receivers 50 will be described in a viewpoint of the first light receiver 50a with reference to FIG. 24

The first light receiver 50a includes a light receiver body 51, a focusing lens 55, and a first light sensor 53a.

In the light receiver body 51, formed is a light passage through which the fluorescence emitted from the first nucleic acid amplification chamber 161a is received. The focusing lens 55 and the first light sensor 53a are sequentially disposed in the light passage from below.

The focusing lens 55 focuses the fluorescence emitted from the first nucleic acid amplification chamber 161a onto the filter 60. At this time, the light incident on the focusing lens 55 may be filtered by the movable filter 60 before being incident on the focusing lens 55.

The first light sensor 53a converts the fluorescence received through the focusing lens 55 into an electrical fluorescence signal.

Figure 26:
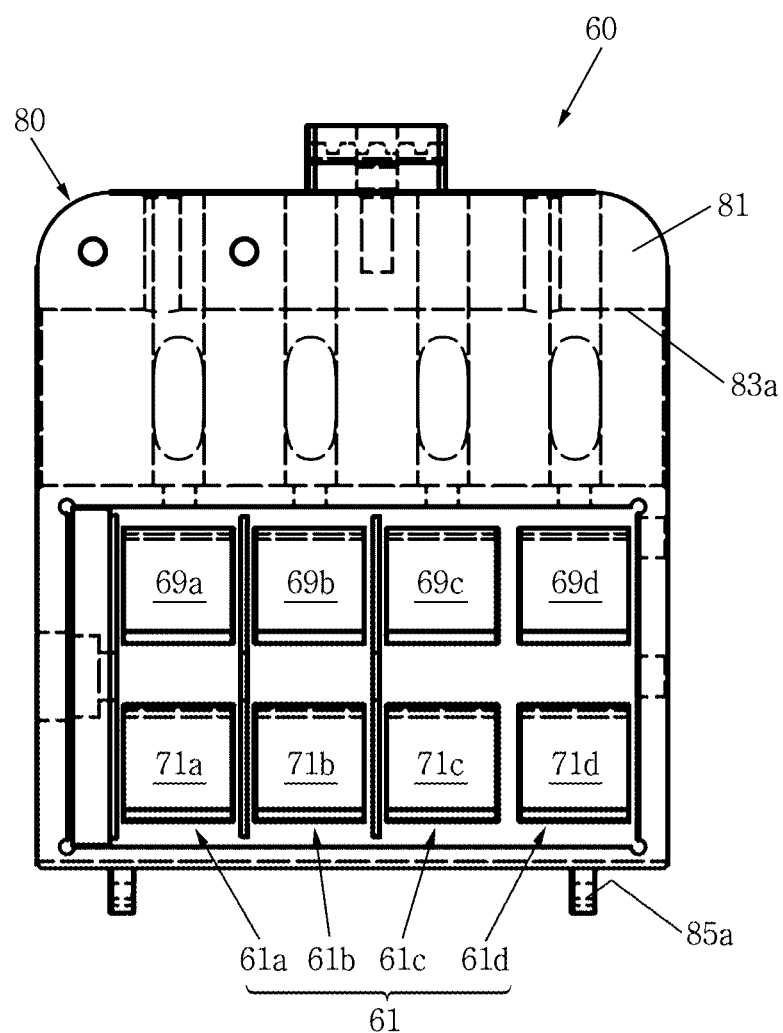
FIG. 26 is a planar view of a filter module of the moving filter shown in FIG. 21.
Figure 27:
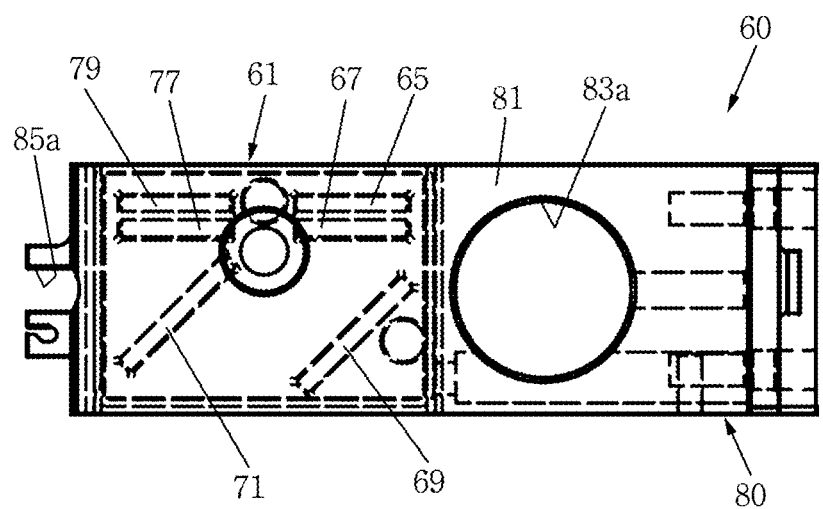
FIG. 27 is a side view of the filter module of the moving filter of FIG. 26.

FIG. 26 is a planar view of the filter modules 61a-61d of the moving filter 60 shown in FIG. 21. FIG. 27 is a side view of the filter modules 61a-61d of the moving filter 60 of FIG. 26.

Referring to FIGS. 24, 26, and 27, the movable filter 60 includes a filter body 61 and a moving member 80. The filter body 61 includes the plurality of filter modules 61a-61d arranged in the horizontal direction to face the plurality of nucleic acid amplification chambers. The moving member 80 is connected to the filter body 61 and can sequentially displace the plurality of filter modules 61a-61d in the horizontal direction to the plurality of nucleic acid amplification chambers.

The plurality of filter modules 61a-61d includes the first through fourth filter modules 61a-61d.

The first filter module 61a filters the light of the first color series output by the plurality of light emitters to selectively pass the light having the first wavelength to the plurality of nucleic acid amplification chambers. Also, the first filter module 61a filters the first fluorescence emitted from the plurality of nucleic acid amplification chambers to selectively pass the light having the (1-1)-th wavelength to the plurality of light receivers.

The second filter module 61b is installed adjacent to the first filter module 61a. The second filter module 61b filters the light of the second color series output by the plurality of light emitters to selectively pass the light having the second wavelength to the plurality of nucleic acid amplification chambers. Also, the second filter module 61b filters the second fluorescence emitted from the plurality of nucleic acid amplification chambers to selectively pass the light having the (2-1)-th wavelength to the plurality of light receivers.

The third filter module 61c is installed adjacent to the second filter module 61b. The third filter module 61c filters the light of the third color series output by the plurality of light emitters to selectively pass the light having the third wavelength to the plurality of nucleic acid amplification chambers. Also, the third filter module 61c filters the third fluorescence emitted from the plurality of nucleic acid amplification chambers to selectively pass the light having the (3-1)-th wavelength to the plurality of light receivers.

The fourth filter module 61d is installed adjacent to the third filter module 61c. The fourth filter module 61d filters the light of the fourth color series output by the plurality of light emitters to selectively pass the light having the fourth wavelength to the plurality of nucleic acid amplification chambers. Also, the fourth filter module 61d filters the fourth fluorescence emitted from the plurality of nucleic acid amplification chambers to selectively pass the light having the (4-1)-th wavelength to the plurality of light receivers.

When a certain filter module among the first through fourth filter modules 61a-61d is positioned to face a particular nucleic acid amplification chamber among the first through fourth nucleic acid amplification chambers, the light emitter corresponding to the particular nucleic acid amplification chamber emits the light of a color that is allowed to pass by the certain filter module. In the example of FIG. 20, the certain filter module is the first filter module 61a, and the particular nucleic acid amplification chamber is the first nucleic acid amplification chamber 161a. Also, the light emitter corresponding to the particular nucleic acid amplification chamber is the first light emitter 30a, and thus the first light emitter 30a emits the light of the first color series allowed to pass by the first filter module 61a.

Each of the first through fourth filter modules 61a-61d includes a filter body 63, a first color filter 67, a total reflection mirror 69, a dichroic mirror 71, and a second color filter 77. Each of the first through fourth filter modules 61a-61d may further include a first infrared (IR) stop filter 65 or a second IR stop filter 79.

In the filter body 63, formed is a U-shaped filtering passage in which the first IR stop filter 65, the first color filter 67, the total reflection mirror 69, the dichroic mirror 71, the second color filter 77, and the second IR stop filter 79 is installed. One end of the filtering passage is connected to the main passage of the light emitter body, and the first IR stop filter 65, the first color filter 67, and the total reflection mirror 69 are sequentially installed in the filtering passage from a side of the main passage. The other end of the filtering passage is connected to the light passage of the light receiver body, and the dichroic mirror 71, the second color filter 77, and the second IR stop filter 79 are installed in the filtering passage. The total reflection mirror 69 and the dichroic mirror 71 are installed at 45 degrees with respect to the horizontal plane to be parallel to each other.

The first IR stop filter 65 filters the light emitted by the light emitter to selectively stop infrared component.

The first color filter 67 filters the light of a particular color series having passed the first IR stop filter 65 to selectively pass the light having a particular wavelength. For example, the first filter module 61a includes a (1-1)-th color filter that filters the light of the first color series to selectively pass the light having a particular wavelength. The second filter module includes a (1-2)-th color filter that filters the light of the second color series to selectively pass the light having the particular wavelength. The third filter module includes a (1-3)-th color filter that filters the light of the third color series to selectively pass the light having the particular wavelength. The fourth filter module includes a (1-4)-th color filter that filters the light of the fourth color series to selectively pass the light having the particular wavelength.

The total reflection mirror 69 totally reflects the light having passed the first color filter 67 to the dichroic mirror 71. The total reflection mirror 69 includes a first through fourth total reflection mirrors 69a-69d provided in the first through fourth filter modules 61a-61d, respectively.

The dichroic mirror 71 reflects the light incident from the total reflection mirror 69 to the nucleic acid amplification chamber positioned below and reflects the fluorescence emitted from the nucleic acid amplification chamber to the second color filter 77 located above. The dichroic mirror 71 includes a first through fourth dichroic mirrors 71a-71d provided in the first through fourth filter modules 61a-61d, respectively.

The second color filter 77 filters the fluorescence having passed the dichroic mirror 71 to selectively pass the fluorescence having a particular wavelength. For example, the first filter module 61a includes a (2-1)-th color filter that filters the fluorescence of the first color series to selectively pass the fluorescence having a particular wavelength. The second filter module includes a (2-2)-th color filter that filters the fluorescence of the second color series to selectively passes the light having the particular wavelength. The third filter module includes a (2-3)-th color filter that filters the fluorescence of the third color series to selectively passes the light having the particular wavelength. The fourth filter module includes a (2-4)-th color filter that filters the fluorescence of the fourth color series to selectively passes the light having a particular wavelength.

The second IR stop filter 65 filters the fluorescence having passed the second color filter 77 to selectively stop infrared component and direct the filtered fluorescence to the light receiver located above.

An eyepiece block 73 is provided between the dichroic mirror 71 and the nucleic acid amplification chamber. The eyepiece block 73 is provided with an eyepiece passage which allows the light reflected by the dichroic mirror 71 to propagate to the nucleic acid amplification chamber while allowing the fluorescence emitted from the nucleic acid amplification chamber to propagate toward the dichroic mirror 71. In the eyepiece passage, installed is an object lens 75 which focuses the light of a certain wavelength band reflected by the dichroic mirror 71 onto the nucleic acid amplification chamber positioned below.

The eyepiece block 73 is connected to the light receiver body 51. A guide groove is formed at a portion connecting the eyepiece block 73 to the light receiver body 51 to enable the filter body 61 to move in the horizontal direction between the eyepiece block 73 and the light receiver body 51.

The moving member 80 includes a moving body 81 connected to one side of the filter body 61 and a motor 87 for moving the moving body 81.

One side of the filter body 61 to which the moving body 81 is connected is opposite to the side where the guide groove is formed. The moving body 81 is connected to the main guide shaft 83 to stably move the filter body 61 in the horizontal direction by the motor 87. An auxiliary guide shaft 85 is connected to an external surface of the filter body 61 on the opposite side to which the main guide shaft 83 is connected. The main guide shaft 83 and the auxiliary guide shaft 85 are parallel to each other. The main guide shaft 83 and the auxiliary guide shaft 85 are fixedly installed between a first support plate 89 and a second support plate 91 provided below the frame P. The moving body 81 has a through hole 83a into which the main guide shaft 83 is inserted. The outer surface of the filter body 61 is provided with a support groove 85a through which the auxiliary guide shaft 85 is inserted to enable the movement of the auxiliary guide shaft 85.

Thus, the filter body 61 can stably move in the horizontal direction, in a state of being connected to the moving body 81, while being guided by the main guide shaft 83 and the auxiliary guide shaft 85.

The motor 87 is mounted on of the frame P, and the drive shaft of the motor 87 is connected to one of a pair of pulleys 93 mounted beneath the frame P. The pair of pulleys 93 are connected to each other by a belt 95. The moving body 81 is connected to the belt 95. Accordingly, the rotational torque of the motor 87 causes the belt 95 to move through the pair of pulleys 93. The belt portion between the pair of pulleys 93 is subject to a linearly translational movement. The moving body 81 is connected to the belt portion between the pair of pulleys 93. Thus, the moving body 81 connected to the belt 95 is subject to a linearly translational movement in the horizontal direction.

A key plate 97 having a plurality of keys 99 is provided so that the plurality of filter modules can be moved precisely to predetermined positions facing the plurality of nucleic acid amplification chambers when the moving body 81 moves in the horizontal direction by the belt 95. In the present embodiment, the key plate 77 has seven keys 99 in consideration that the fluorescence detection for the nucleic acids is performed for the first to fourth nucleic acid amplification chambers.

The seven keys 99 are formed at positions that may face the plurality of nucleic acid amplification chambers. The spacing between two adjacent keys 99 may correspond to the spacing between two adjacent nucleic acid amplification chambers.

Though an example of controlling the sequential movement of the plurality of filter modules according to the rotation of the motor 87 by using the key plate 97 has been described above, the present disclosure is not limited thereto. In another embodiment, the sequential movement of the plurality of filter modules may be controlled by using the encoder which detects the rotational angle of the motor 87.

The key plate 97 may be installed below the frame P, for example, between the pair of pulleys 93.

The fluorescence detection process for the nucleic acid amplification chambers 161a-161d using the fluorescence detection unit 197 according to the present embodiment will now be described with reference to FIGS. 28-34. FIGS. 28-34 illustrate the fluorescence detection process using the fluorescence detection unit 197.

Referring to FIGS. 28-34, the first through fourth filter modules 61a-61d of the filter body 61 direct the light of the first through fourth colors to the first through fourth nucleic acid amplification chambers 161a-161d and detect the fluorescence emanating from the first through fourth nucleic acid amplification chambers 161a-161d while moving over the first through fourth nucleic acid amplification chambers 161a-161d sequentially.

In order to direct the light of the first through fourth colors to the first through fourth nucleic acid amplification chambers 161a-161d and detect the fluorescence, the first through fourth filter modules 61a-61d moves horizontally in a direction of y-axis in seven steps sequentially.

Figure 28:
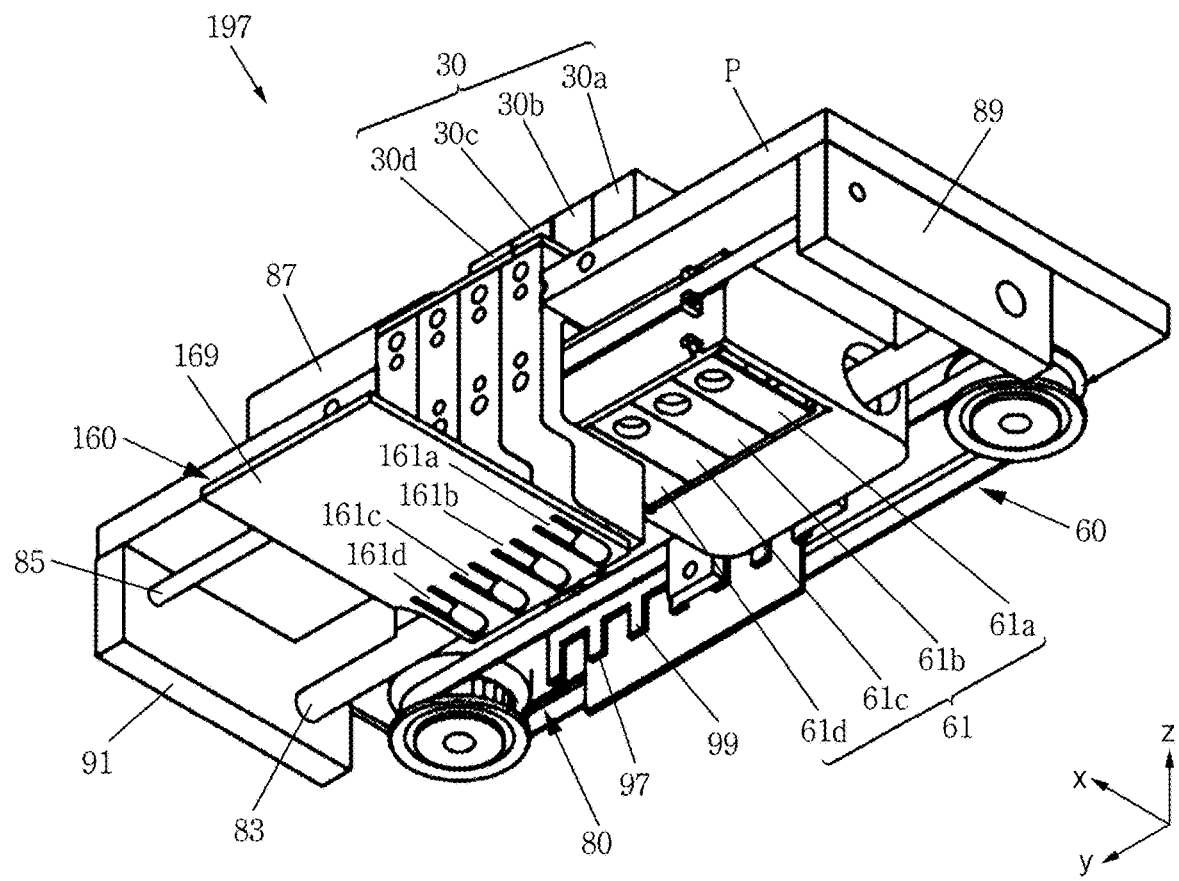
FIGS. 28 through 34 illustrate a fluorescence detection process using the fluorescence detection unit.

First, the filter body 61 is horizontally moved in the direction of y-axis, so that the fourth filter module 61d is positioned over the first nucleic acid amplification chamber 161a as shown in FIG. 28. This case is intended for detecting the fluorescence of the fourth color for the first nucleic acid amplification chamber 161a. The motor 87 is driven to locate the fourth filter module 61d over the first nucleic acid amplification chamber 161a. If the fourth light source of the first light emitter 30a is turned on, the light of the fourth color is directed to the first nucleic acid amplification chamber 161a, and the fluorescence emitted from the first nucleic acid amplification chamber 161a is incident on the light sensor of the first light receiver to be converted into an electrical signal.

Figure 29:
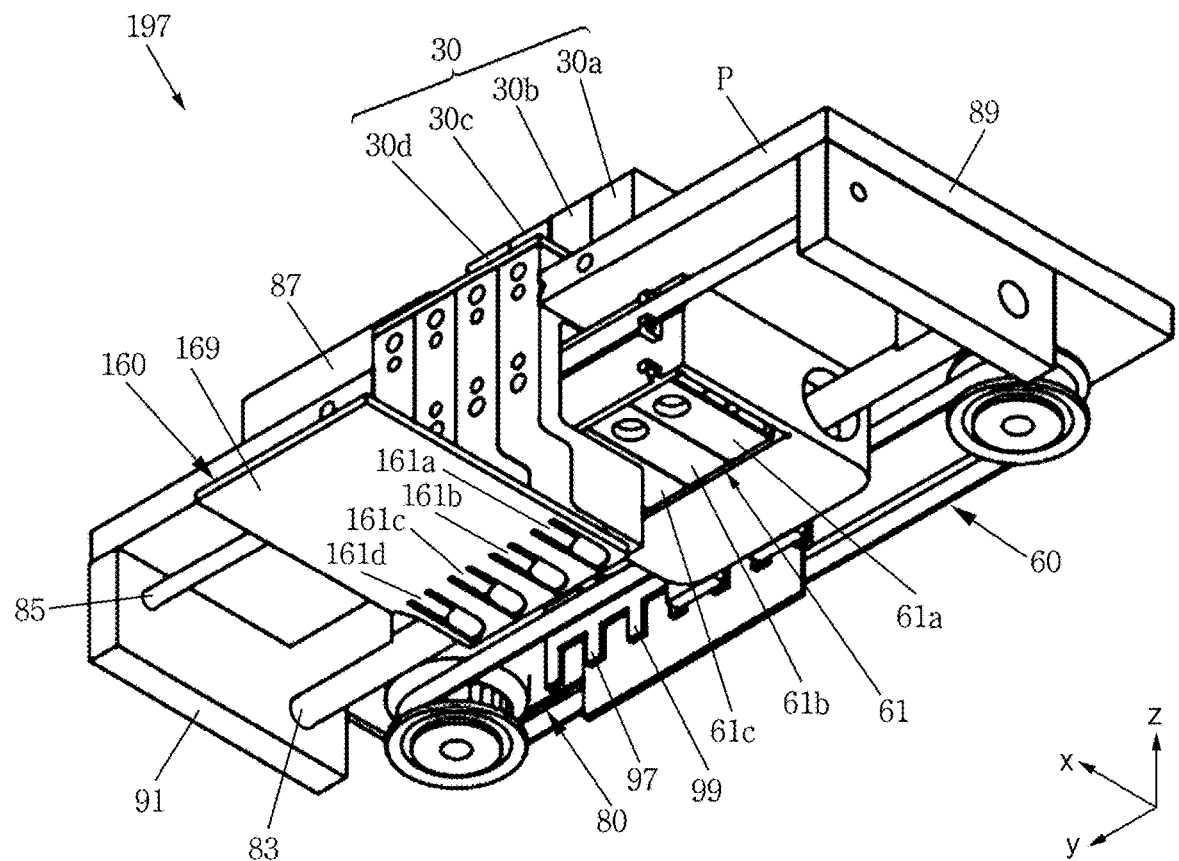

Next, the filter body 61 is horizontally moved in the direction of y-axis, so that the fourth filter module 61d is positioned over the second nucleic acid amplification chamber 161b and the third filter module 61c is positioned over the first nucleic acid amplification chamber 161a as shown in FIG. 29. This case is intended for detecting the fluorescence of the third color for the first nucleic acid amplification chamber 161a and detecting the fluorescence of the fourth color for the second nucleic acid amplification chamber 161b. If the motor 87 is driven to locate the fourth filter module 61d over the second nucleic acid amplification chamber 161b, the third filter module 61c is aligned to the first nucleic acid amplification chamber 161a.

If the fourth light source of the second light emitter 30b is turned on, the light of the fourth color is directed to the second nucleic acid amplification chamber 161b, and the fluorescence emitted from the second nucleic acid amplification chamber 161b is incident on the light sensor of the second light receiver to be converted into an electrical signal.

If the third light source of the first light emitter 30a is turned on, the light of the third color is directed to the first nucleic acid amplification chamber 161a, and the fluorescence emitted from the first nucleic acid amplification chamber 161a is incident on the light sensor of the first light receiver to be converted into an electrical signal.

Figure 30:
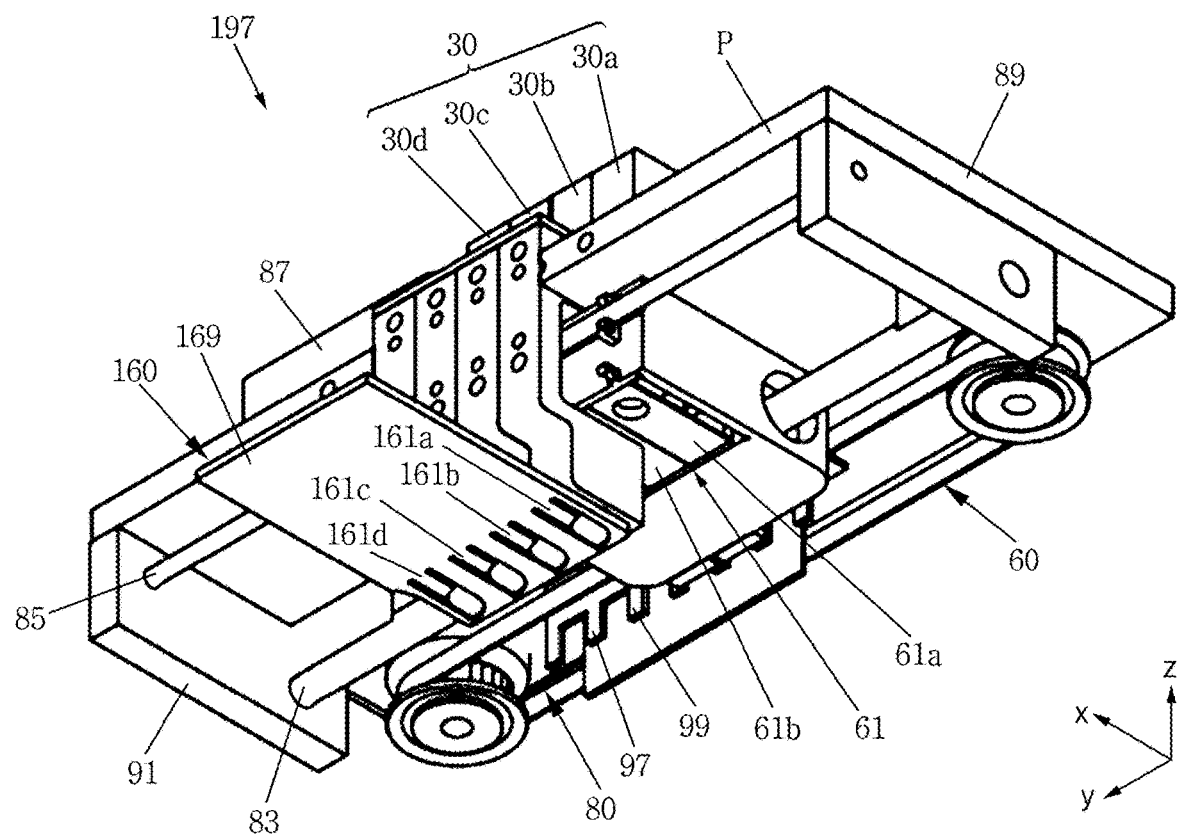

Next, the filter body 61 is horizontally moved in the direction of y-axis further, so that the fourth filter module 61d is positioned over the third nucleic acid amplification chamber 161c, the third filter module 61c is positioned over the second nucleic acid amplification chamber 161b, and the second filter module 61b is positioned over the first nucleic acid amplification chamber 161a as shown in FIG. 30. This case is intended for detecting the fluorescence of the second color for the first nucleic acid amplification chamber 161a, detecting the fluorescence of the third color for the second nucleic acid amplification chamber 161b, and detecting the fluorescence of the fourth color for the third nucleic acid amplification chamber 161c. If the motor 87 is driven to locate the fourth filter module 61d over the third nucleic acid amplification chamber 161c, the third filter module 61c is aligned to the second nucleic acid amplification chamber 161b and the second filter module 61b is aligned to the first nucleic acid amplification chamber 161a.

If the fourth light source of the third light emitter 30c is turned on, the light of the fourth color is directed to the third nucleic acid amplification chamber 161c, and the fluorescence emitted from the third nucleic acid amplification chamber 161c is incident on the light sensor of the third light receiver to be converted into an electrical signal.

If the third light source of the second light emitter 30b is turned on, the light of the third color is directed to the second nucleic acid amplification chamber 161b, and the fluorescence emitted from the second nucleic acid amplification chamber 161b is incident on the light sensor of the second light receiver to be converted into an electrical signal.

If the second light source of the first light emitter 30a is turned on, the light of the second color is directed to the first nucleic acid amplification chamber 161a, and the fluorescence emitted from the first nucleic acid amplification chamber 161a is incident on the light sensor of the first light receiver to be converted into an electrical signal.

Figure 31:
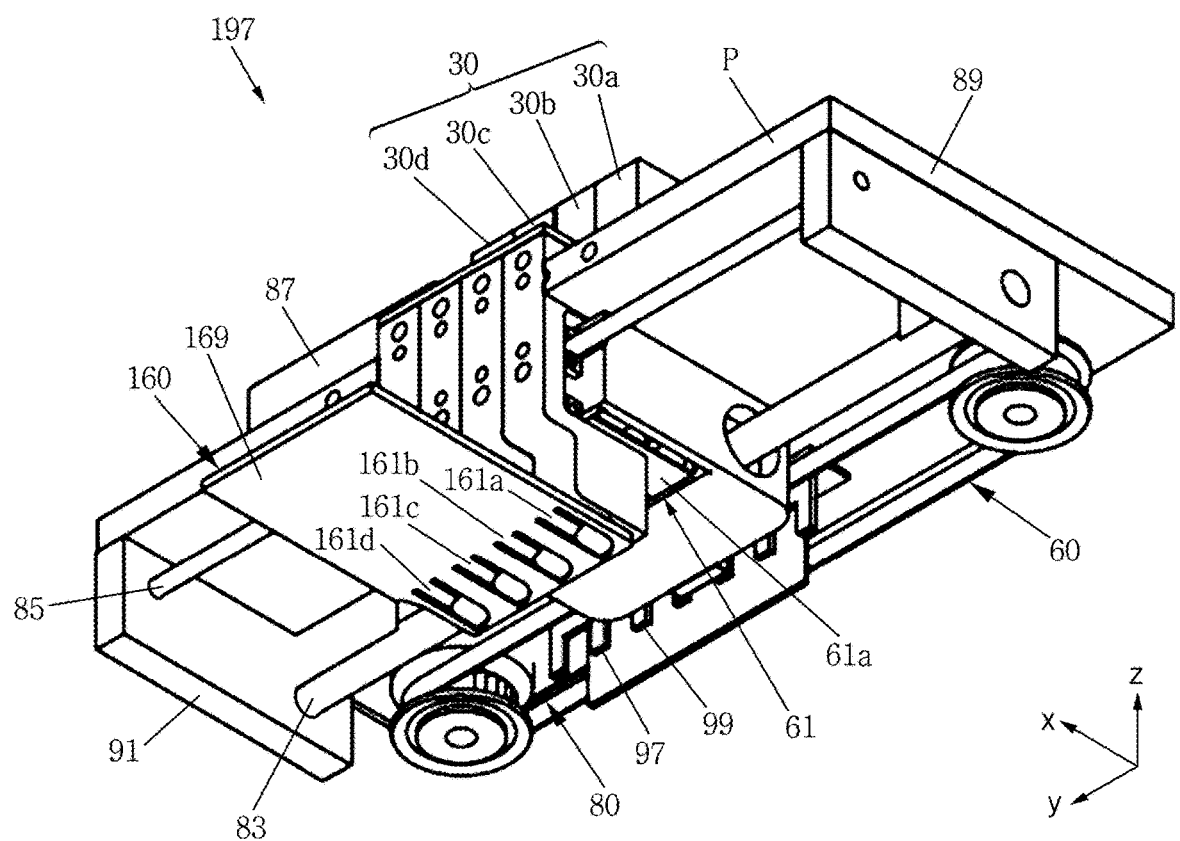

Next, the filter body 61 is horizontally moved in the direction of y-axis further, so that the fourth filter module 61*d* is positioned over the fourth nucleic acid amplification chamber 161*d*, the third filter module 61*c* is positioned over the third nucleic acid amplification chamber 161*c*, the second filter module 61*b* is positioned over the second nucleic acid amplification chamber 161*b*, and the first filter module 61*a* is positioned over the first nucleic acid amplification chamber 161*a* as shown in FIG. 31. This case is intended for detecting the fluorescence of the first color for the first nucleic acid amplification chamber 161*a*, detecting the fluorescence of the second color for the second nucleic acid amplification chamber 161*b*, detecting the fluorescence of the third color for the third nucleic acid amplification chamber 161*c*, and detecting the fluorescence of the fourth color for the fourth nucleic acid amplification chamber 161*d*.

If the motor 87 is driven to locate the fourth filter module 61*d* over the fourth nucleic acid amplification chamber 161*d*, the third filter module 61*c* is aligned to the third nucleic acid amplification chamber 161*c*, the second filter module 61*b* is aligned to the second nucleic acid amplification chamber 161*b*, and the first filter module 61*a* is aligned to the first nucleic acid amplification chamber 161*a*.

If the fourth light source of the fourth light emitter 30*c* is turned on, the light of the fourth color is directed to the fourth nucleic acid amplification chamber 161*d*, and the fluorescence emitted from the fourth nucleic acid amplification chamber 161*d* is incident on the light sensor of the fourth light receiver to be converted into an electrical signal.

If the third light source of the third light emitter 30*c* is turned on, the light of the third color is directed to the third nucleic acid amplification chamber 161*c*, and the fluorescence emitted from the third nucleic acid amplification chamber 161*c* is incident on the light sensor of the third light receiver to be converted into an electrical signal.

If the second light source of the second light emitter 30*b* is turned on, the light of the second color is directed to the second nucleic acid amplification chamber 161*b*, and the fluorescence emitted from the second nucleic acid amplification chamber 161*b* is incident on the light sensor of the second light receiver to be converted into an electrical signal.

If the first light source of the first light emitter 30*a* is turned on, the light of the first color is directed to the first nucleic acid amplification chamber 161*a*, and the fluorescence emitted from the first nucleic acid amplification chamber 161*a* is incident on the light sensor of the first light receiver to be converted into an electrical signal.

Figure 32:
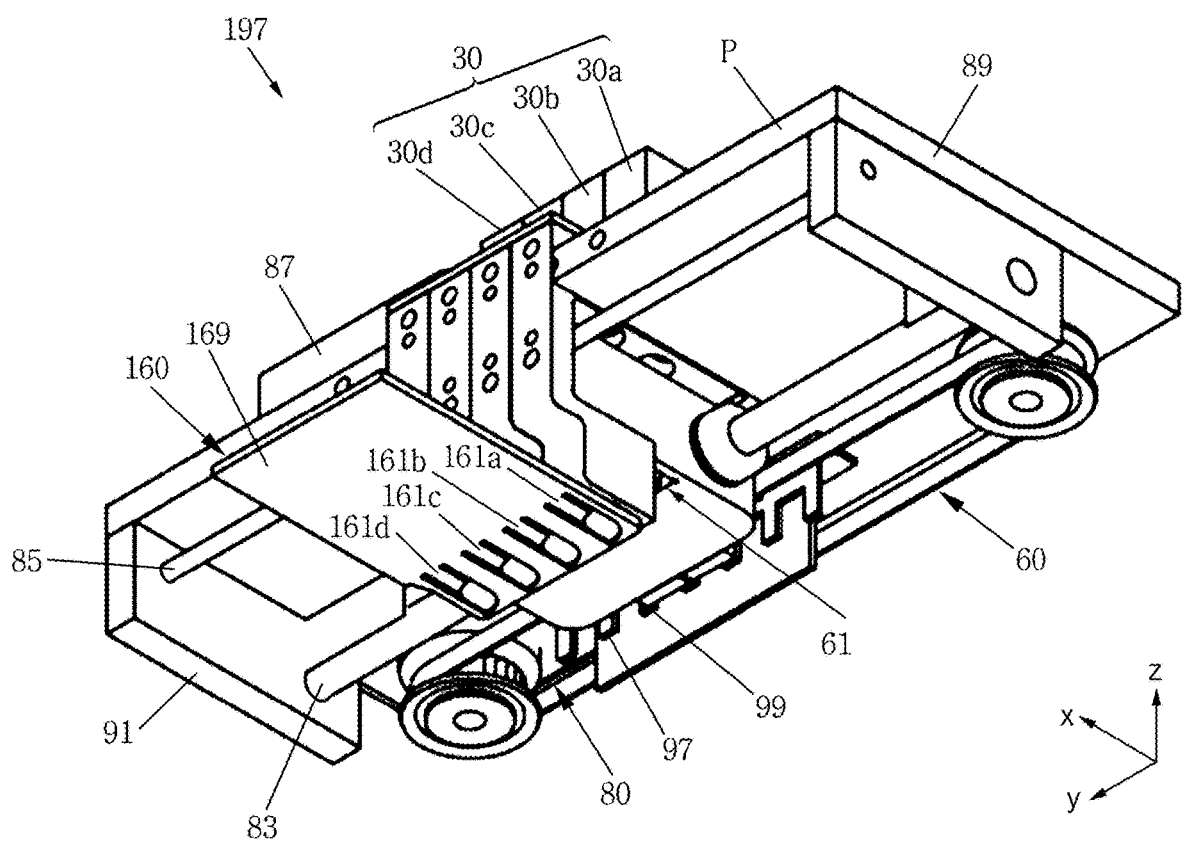

Next, the filter body 61 is horizontally moved in the direction of y-axis further, so that the third filter module 61*c* is positioned over the fourth nucleic acid amplification chamber 161*d*, the second filter module 61*b* is positioned over the third nucleic acid amplification chamber 161*c*, and the first filter module 61*a* is positioned over the second nucleic acid amplification chamber 161*b* as shown in FIG. 32. This case is intended for detecting the fluorescence of the first color for the second nucleic acid amplification chamber 161*b*, detecting the fluorescence of the second color for the third nucleic acid amplification chamber 161*c*, and detecting the fluorescence of the third color for the fourth nucleic acid amplification chamber 161*d*.

If the motor 87 is driven to locate the third filter module 61*c* over the fourth nucleic acid amplification chamber 161*d*, the second filter module 61*b* is aligned to the third nucleic acid amplification chamber 161*c* and the first filter module 61*a* is aligned to the second nucleic acid amplification chamber 161*b*. At this time, the fourth filter module 61*d* moves out of the fourth nucleic acid amplification chamber 161*d*.

If the third light source of the fourth light emitter 30*d* is turned on, the light of the third color is directed to the fourth nucleic acid amplification chamber 161*d*, and the fluorescence emitted from the fourth nucleic acid amplification chamber 161*d* is incident on the light sensor of the fourth light receiver to be converted into an electrical signal.

If the second light source of the third light emitter 30*c* is turned on, the light of the second color is directed to the third nucleic acid amplification chamber 161*c*, and the fluorescence emitted from the third nucleic acid amplification chamber 161*c* is incident on the light sensor of the third light receiver to be converted into an electrical signal.

If the first light source of the second light emitter 30*b* is turned on, the light of the first color is directed to the second nucleic acid amplification chamber 161*b*, and the fluorescence emitted from the second nucleic acid amplification chamber 161*b* is incident on the light sensor of the second light receiver to be converted into an electrical signal.

Figure 33:
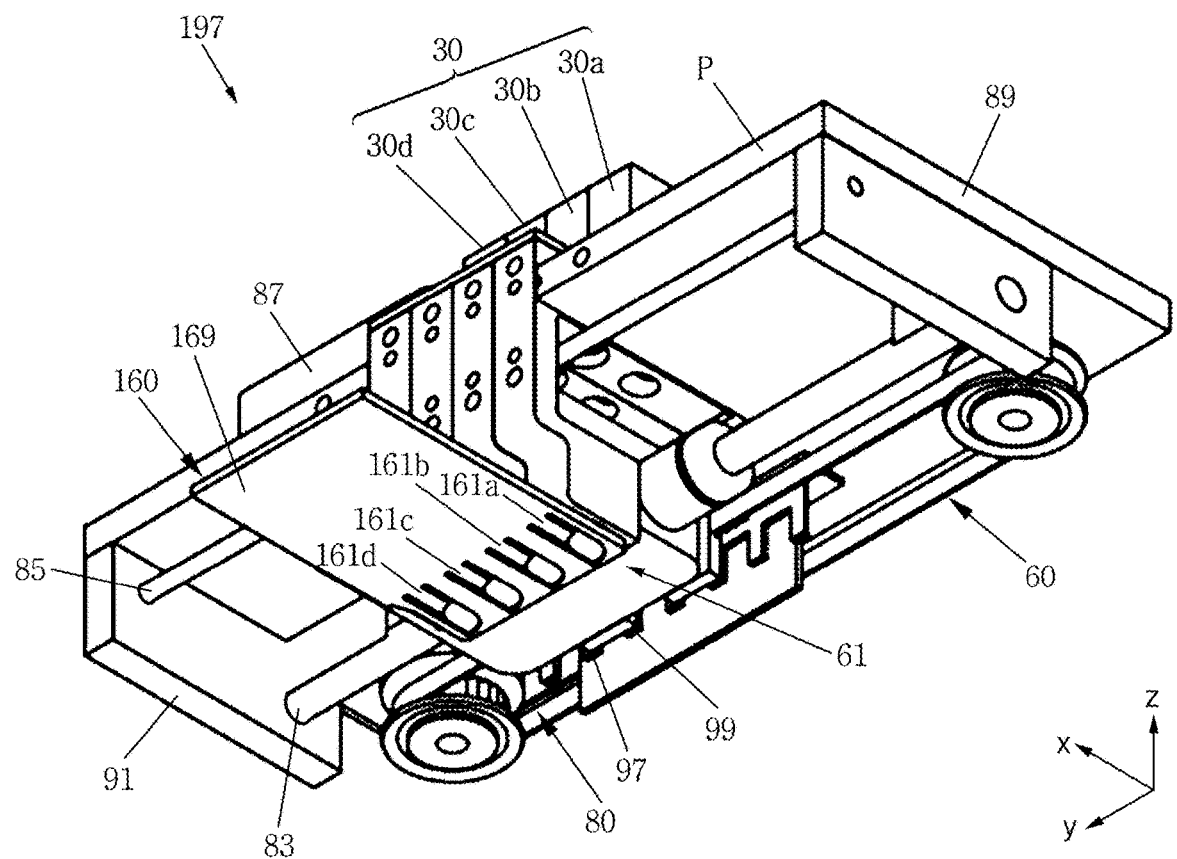

Next, the filter body 61 is horizontally moved in the direction of y-axis further, so that the second filter module 61*b* is positioned over the fourth nucleic acid amplification chamber 161*d* and the first filter module 61*a* is positioned over the third nucleic acid amplification chamber 161*c* as shown in FIG. 33. This case is intended for detecting the fluorescence of the first color for the third nucleic acid amplification chamber 161*c* and detecting the fluorescence of the second color for the fourth nucleic acid amplification chamber 161*d*.

If the motor 87 is driven to locate the second filter module 61*b* over the fourth nucleic acid amplification chamber 161*d*, the first filter module 61*a* is aligned to the third nucleic acid amplification chamber 161*c*. At this time, the fourth filter module 61*d* and the third filter module 61*c* move out of the fourth nucleic acid amplification chamber 161*d*.

If the second light source of the fourth light emitter 30*d* is turned on, the light of the second color is directed to the fourth nucleic acid amplification chamber 161*d*, and the fluorescence emitted from the fourth nucleic acid amplification chamber 161*d* is incident on the light sensor of the fourth light receiver to be converted into an electrical signal.

If the first light source of the third light emitter 30*c* is turned on, the light of the first color is directed to the third nucleic acid amplification chamber 161*c*, and the fluorescence emitted from the third nucleic acid amplification chamber 161*c* is incident on the light sensor of the third light receiver to be converted into an electrical signal.

Figure 34:
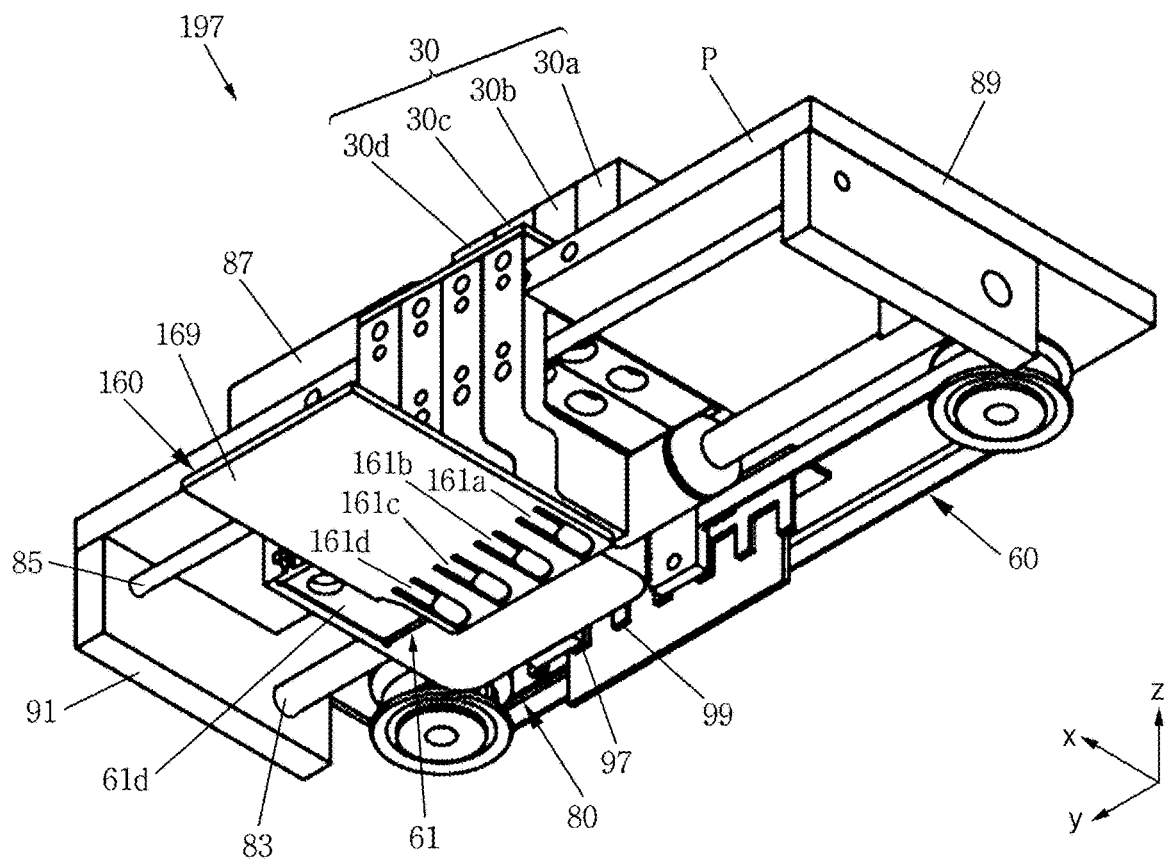

Next, the filter body 61 is horizontally moved in the direction of y-axis further, so that the first filter module 61*a* is positioned over the fourth nucleic acid amplification chamber 161*d* as shown in FIG. 34. This case is intended for detecting the fluorescence of the first color for the fourth nucleic acid amplification chamber 161*d*.

The motor 87 is driven to locate the first filter module 61*a* over the fourth nucleic acid amplification chamber 161*d*. At this time, the second through fourth filter module 61*b*-61*d* move out of the fourth nucleic acid amplification chamber 161*d*.

If the first light source of the fourth light emitter 30*d* is turned on, the light of the first color is directed to the fourth nucleic acid amplification chamber 161*d*, and the fluorescence emitted from the fourth nucleic acid amplification chamber 161*d* is incident on the light sensor of the fourth light receiver to be converted into an electrical signal.

Table 1 summarizes the fluorescence signals for the light of the first through fourth colors in the cases illustrated in FIGS. 28-34. In Table 1, the first through fourth colors may represent the first through fourth color series, respectively.

TABLE 1

| | Filter Body Movement Sequence | | | | | | |
|---|---|---|---|---|---|---|---|
| | First | Second | Third | Fourth | Fifth | Sixth | Seventh |
| First nucleic acid chamber | fourth color | third color | second color | first color | | | |
| Second nucleic acid chamber | | fourth color | third color | second color | first color | | |
| Third nucleic acid chamber | | | fourth color | third color | second color | first color | |
| Fourth nucleic acid chamber | | | | fourth color | third color | second color | first color |

As described above, the fluorescence detector according to the present embodiment optically detects the fluorescence of a plurality of wavelength bands after the amplification of nucleic acids while moving only the moving filter with respect to the nucleic acid amplification module, the light emitter, and the light receiver all of which are fixedly arranged. Thus, the device according to the present disclosure has high driving stability compared with a conventional system in which the whole optical system is moved/

In case of using only a small volume of reaction reagent by utilizing the microfluidic technology, the alignment of the nucleic acid amplification chamber and the optical axis is important. The present disclosure, however, allows to detect the fluorescence of the plurality of wavelength bands more precisely from the nucleic acid amplification chamber since the nucleic acid amplification chamber and the light receiver is fixed and only the moving filter is subject to the linear movement.

In case of using an optical system capable of detecting the fluorescence of the first through fourth color series for the first to fourth nucleic acid amplification chambers as in the exemplary embodiment, sixteen independent reactions can be measured in a single nucleic acid amplification module as shown in Table 1.

While the present specification contains a number of specific implementation details, it should be understood that they are not to be construed as limitations on the scope of any disclosure or claims, but to be construed as a description of features that may be specific to a particular embodiment of a particular disclosure. Certain features described with respect to contexts of independent embodiments may be implemented in combination in a single embodiment. Conversely, various features described in the context of a single embodiment may also be implemented in other embodiments either individually or in any suitable sub-combination. Further, although some features may be described to operate in a particular combination and may be initially depicted as so claimed, one or more features from the claimed combination may in some cases be excluded from the combination, and a claimed combination may be replaced by a sub-combination or a variant of the sub-combination.

Similarly, although the operations are depicted in the drawings in a particular order, it should not be understood that such operations need to be performed in that particular order or sequential order to achieve the desired result or all the depicted operations should be performed.

INDUSTRIAL APPLICABILITY

The present disclosure relates to a nucleic acid analysis apparatus using a cartridge and applicable to a molecular diagnostic POCT equipment. The nucleic acid analysis apparatus according to the present disclosure can be used in applications such as a diagnosis of disease using the nucleic acid extraction, the nucleic acid amplification, and the fluorescence detection techniques.

The cartridge according to the present disclosure, which is a disposable cartridge employing a microfluidic system for single use only, includes a pretreatment chamber and collectively performs the nucleic acid extraction through the crushing of the injected sample, the cell disruption, and the purification as well as the nucleic acid amplification.

The nucleic acid analysis apparatus according to the present disclosure can integratively perform the nucleic acid test through the nucleic acid extraction and amplification using the cartridge. Since the fluorescence detector is installed before the nucleic acid amplification chamber in which nucleic acid amplification is performed after the nucleic acid extraction on the cartridge, the nucleic acids can be detected by optically detecting the fluorescence of a plurality of wavelength bands after the nucleic acid amplification is performed.

The present disclosure is industrially applicable since it actually can be implemented obviously and has a sufficiently high possibility of commercialization or sales.

DESCRIPTION OF REFERENCE NUMERALS

30: light emitter, 30a: first light emitter, 30b: second light emitter
30c: third light emitter, 30d: fourth light emitter, 31: light emitter body
33a: first light source, 33b: second light source, 33c: third light source
33d: fourth light source, 35a: first focusing lens
35b: second focusing lens, 35c: third focusing lens
35d: fourth focusing lens, 37a: first mirror
37b: second mirror, 37c: third mirror, 37d: fourth mirror
50: light receiver, 50a: first light receiver
50b: second light receiver, 50c: third light receiver, 50d: fourth light receiver
51: light receiver body, 53a: first light sensor, 53b: second light sensor
53c: third light sensor, 53d: fourth light sensor, 55: focusing lens
57: third IR stop filter, 60: movable filter
61: filter module, 61a: first filter module, 61b: second filter module 61c: third filter module, 61d: fourth filter module, 63: filter body
65: first IR stop filter, 67: first color filter, 69: total reflection mirror
71: dichroic mirror, 73: eyepiece block, 75: objective lens
77: second color filter, 79: second IR stop filter
80: objective lens, 81: moving body, 83: main guide shaft
85: auxiliary guide shaft, 87: motor, 89: first support plate
91: second support plate, 93: pulley, 95: belt
97: key plate, 99: key, 100: nucleic acid analysis apparatus
110: cartridge, 131: chamber module, 133: air valve module
135: liquid valve module, 137: pump, 139: pump hole
140: pretreatment chamber, 141: chamber body, 141a: upper body
141b: lower body, 142: inlet, 143: outlet
144: internal space, 145: cup filter, 146: filter portion
147: cup portion, 149: pretreatment fluid, 149a: pretreatment fluid
149b: magnet block, 149c: cell disruption particles, 151: separation chamber
153: cleaning chamber, 153a: first cleaning chamber, 153b: second cleaning chamber
155: reaction chamber, 157: elution chamber, 158: waste chamber
159: nucleic acid amplification reagent chamber, 160: nucleic acid amplification module, 161: nucleic acid amplification chamber
169: module body, 172: air valve actuator, 173: first magnetic field applying unit
173a: (1-1)-th magnetic field applying segment, 173b: (1-2)-th magnetic field applying segment
174: liquid valve actuator, 174a: electromagnet, 175: second magnetic field applying unit
176: first heater, 177: pump driving unit, 178: control unit
179: second heater, 181: sample, 183: primarily purified liquid
185: precipitate, 186: the secondarily purified liquid, 187: floating matter
191: a stage transport unit, 192: stage, 193: through hole
195: nucleic acid extraction unit, 197: fluorescence detection unit
411: valve structure, 413: valve column, 415: diaphragm
417: valve body, 419: valve dome, 421: metal plate
423: connecting hollow

What is claimed is:

1. A nucleic acid analysis device, comprising:
a stage on which a cartridge is mountable, wherein the cartridge comprises a plurality of chambers for extracting nucleic acids from a sample including a pretreatment chamber in which the sample is crushed and subject to homogenization, cell disruption, and purification;
a nucleic acid extraction unit performing a nucleic acid extraction and a nucleic acid amplification through crushing of the sample, the cell disruption, and the nucleic acid purification by applying a magnetic field to the cartridge, the nucleic acid extraction unit comprising:
a pump driving unit for applying a pressure required for fluid movements between chambers of the cartridge; and
a control unit controlling the stage and the nucleic acid extraction unit so that the nucleic acid extraction and the nucleic acid amplification through the crushing of the sample, the cell disruption, and the nucleic acid purification are collectively performed.

2. The nucleic acid analysis device of claim 1, wherein the nucleic acid extraction unit intermittently applies the magnetic field to the pretreatment chamber to move a magnet block contained in the pretreatment chamber and facilitate the crushing and the cell disruption for the sample injected to the pretreatment chamber and the nucleic acid extraction unit applies the magnetic field to a reaction chamber to fix or release magnetic particles contained in the reaction chamber and facilitate cleaning and the nucleic acid extraction.

3. The nucleic acid analysis device of claim 1, wherein the nucleic acid extraction unit comprises:
a first heater installed outside a separation chamber in the cartridge for applying heat to the separation chamber to facilitate a thermal phase separation for a primarily purified liquid supplied from the pretreatment chamber in the cartridge; and
a second heater installed outside a nucleic acid amplification chamber in the cartridge for applying heat to the nucleic acid amplification chamber to facilitate a nucleic acid amplification reaction.

4. The nucleic acid analysis device of claim 3, wherein the chamber further comprises:
a pump driven by the pump driving unit to apply air pressure to an air valve module.

5. The nucleic acid analysis device of claim 4, wherein the nucleic acid extraction unit further comprises:
a valve actuating unit comprising an air valve actuator for opening and closing valves in the air valve module, and a liquid valve actuator for opening and closing valves in the liquid valve module.

6. The nucleic acid analysis device of claim 5, wherein each of the valves in the liquid valve module comprises:
a valve structure made of elastic material and connecting or disconnecting flow paths leading to respective chambers to be connected; and
a metal plate installed below the valve structure to move the valve structure up and down according to the magnetic field applied through the liquid valve actuator to connect or disconnect the flow paths.

7. The nucleic acid analysis device of claim 6, wherein the valve structure comprises:
a tubular valve column;
a valve body positioned at a center of the valve column in a radial direction being spaced apart from an inner wall of the valve column, having a valve dome for opening and closing a flow path in its upper portion and having a metal plate attached to its bottom; and
a diaphragm connecting the valve body to the inner wall of the valve column and allowing the valve body to move up and down elastically.

8. The nucleic acid analysis device of claim 5, further comprising:
a fluorescence detection unit optically detecting fluorescence of a plurality of wavelength bands after the nucleic acids are amplified on the cartridge,
wherein the control unit controls operations of the stage, the nucleic acid extraction unit, and the fluorescence detection unit so that the nucleic acid extraction, the nucleic acid amplification, and the fluorescence detection are collectively performed through the crushing of the sample, the cell disruption, and the purification.

9. The nucleic acid analysis device of claim 8, wherein the fluorescence detection unit comprises:
a plurality of light emitters arranged to be parallel to the plurality of nucleic acid amplification chambers disposed in a horizontal direction on the cartridge to output lights of a plurality of color series to be emitted to the plurality of nucleic acid amplification chambers, respectively;

a plurality of light receivers, each being arranged to form a pair with a respective one of the plurality of light emitters including an optical sensor suitable for receiving the fluorescence emitted from a corresponding one of the plurality of nucleic acid amplification chambers to convert into a fluorescence signal; and a movable filter placed between an assembly of the plurality of light emitters and the plurality of light receivers and the plurality of nucleic acid amplification chambers and installed to be movable in a direction in which the plurality of nucleic acid amplification chambers are arranged to be capable of moving to face the plurality of nucleic acid amplification chambers, and comprising a plurality of filter modules which selectively passes lights of a specific wavelength from the lights of the plurality of color series incident from the plurality of light emitters to direct filtered lights to the plurality of nucleic acid amplification chambers and selectively passes the fluorescence of a specific wavelength out of the fluorescence emitted from the plurality of nucleic acid amplification chambers to direct filtered fluorescence to the plurality of light receivers.

10. The nucleic acid analysis device of claim 8, further comprising:

a stage transport unit for loading or unloading the stage to and from a work area in which the pump driving unit, the heater, the valve actuating unit, and the fluorescence detection unit are installed.

11. The nucleic acid analysis device of claim 10, wherein the stage is formed to have a through hole at a portion where the cartridge is mounted, wherein the pump driving unit and the liquid valve actuator are coupled to the cartridge mounted on the stage through the through hole.

12. The nucleic acid analysis device of claim 10, wherein the stage transfer unit separates the stage from the work area when the cartridge is to be mounted or to be detached from the stage while moving the stage to the work area when the cartridge is mounted on the stage.

13. The nucleic acid analysis device of claim 10, wherein the heater, the pump driving unit, the valve actuating unit, and the fluorescence detection unit are separated from the work area before the stage is loaded into or unloaded from the work area, while being moved and coupled to the work area when the stage is loaded into the work area.

* * * * *